United States Patent
Takahashi

(10) Patent No.: US 8,913,111 B2
(45) Date of Patent: Dec. 16, 2014

(54) IMAGE PROCESSING DEVICE, ELECTRONIC APPARATUS, INFORMATION STORAGE DEVICE, AND IMAGE PROCESSING METHOD

(75) Inventor: Jumpei Takahashi, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/532,163

(22) Filed: Jun. 25, 2012

(65) Prior Publication Data
US 2012/0327205 A1 Dec. 27, 2012

Related U.S. Application Data

(63) Continuation of application No. PCT/JP2010/071963, filed on Dec. 8, 2010.

(30) Foreign Application Priority Data

Dec. 28, 2009 (JP) ................ 2009-296964

(51) Int. Cl.
*A61B 1/04* (2006.01)
*G02B 23/24* (2006.01)
*G06T 5/50* (2006.01)

(52) U.S. Cl.
CPC .......... *A61B 1/04* (2013.01); *G02B 23/2461* (2013.01); *G02B 23/2476* (2013.01); *G06T 5/50* (2013.01); *G06T 2207/20221* (2013.01); *G06T 2207/30101* (2013.01)
USPC ......................................... 348/65

(58) Field of Classification Search
USPC ......................................... 348/65
See application file for complete search history.

(56) References Cited

U.S. PATENT DOCUMENTS

| 4,814,859 | A * | 3/1989 | Kimura et al. | 348/30 |
| 5,398,685 | A * | 3/1995 | Wilk et al. | 600/437 |
| 5,540,677 | A * | 7/1996 | Sinofsky | 606/8 |
| 6,516,217 | B1 * | 2/2003 | Tsujita | 600/477 |
| 6,956,602 | B2 * | 10/2005 | Higuchi et al. | 348/65 |

(Continued)

FOREIGN PATENT DOCUMENTS

| CN | 101400294 A | 4/2009 |
| EP | 1 698 271 A1 | 9/2006 |

(Continued)

OTHER PUBLICATIONS

International Search Report dated Mar. 8, 2011 issued in PCT/JP2010/071963.

(Continued)

*Primary Examiner* — Sath V Perungavoor
*Assistant Examiner* — Jeffery Williams
(74) *Attorney, Agent, or Firm* — Scully, Scott, Murphy & Presser, P.C.

(57) ABSTRACT

The image processing device includes a first image acquisition section that acquires a first image that includes an object image including information within a wavelength band of white light, a second image acquisition section that acquires a second image that includes an object image including information within a specific wavelength band, a type determination section that determines a type of the object image in the second image based on a feature quantity of each pixel included in the second image, and a highlight section that performs a highlight process on the first image based on the type of the object image determined by the type determination section.

32 Claims, 34 Drawing Sheets

(56) References Cited

U.S. PATENT DOCUMENTS

| | | |
|---|---|---|
| 7,668,377 B2 * | 2/2010 | Curti et al. .................... 382/224 |
| 2002/0026098 A1 | 2/2002 | Kobayashi |
| 2002/0123666 A1 * | 9/2002 | Matsumoto .................. 600/178 |
| 2002/0131625 A1 * | 9/2002 | Vining et al. ................. 382/128 |
| 2002/0183607 A1 * | 12/2002 | Bauch et al. ................. 600/407 |
| 2003/0071894 A1 | 4/2003 | Higuchi et al. |
| 2003/0176768 A1 | 9/2003 | Gono et al. |
| 2004/0044275 A1 | 3/2004 | Hakamata |
| 2006/0004292 A1 | 1/2006 | Beylin |
| 2006/0198551 A1 | 9/2006 | Abe et al. |
| 2007/0153542 A1 * | 7/2007 | Gono et al. .................. 362/574 |
| 2007/0213593 A1 | 9/2007 | Nakaoka |
| 2008/0090198 A1 | 4/2008 | Liang et al. |
| 2008/0281154 A1 | 11/2008 | Gono et al. |
| 2008/0294105 A1 | 11/2008 | Gono et al. |
| 2009/0040298 A1 | 2/2009 | Yamazaki et al. |
| 2009/0137908 A1 * | 5/2009 | Patwardhan .................. 600/476 |

FOREIGN PATENT DOCUMENTS

| | | |
|---|---|---|
| EP | 1 839 558 A1 | 10/2007 |
| EP | 1 994 878 A1 | 11/2008 |
| JP | 08-224209 | 9/1996 |
| JP | 2000-115553 | 4/2000 |
| JP | 2001-017379 | 1/2001 |
| JP | 2001-1017379 | 1/2001 |
| JP | 2002-034893 | 2/2002 |
| JP | 2003-093338 | 4/2003 |
| JP | 2004-024497 | 1/2004 |
| JP | 2004024497 A * | 1/2004 |
| JP | 2004-112772 | 4/2004 |
| JP | 3560671 B2 * | 9/2004 |
| JP | 2005-198794 | 7/2005 |
| JP | 2005-342234 | 12/2005 |
| JP | 2006-068113 | 3/2006 |
| JP | 2006-166940 | 6/2006 |
| JP | 2006-192065 | 7/2006 |
| JP | 2006-239203 | 9/2006 |
| JP | 2007-229053 | 9/2007 |
| WO | WO 2007/119297 A1 | 10/2007 |

OTHER PUBLICATIONS

US 6,692,429, 02/2004, Imaizumi, et al. (withdrawn).
European Extended Supplementary Search Report dated Feb. 27, 2014 from related European Application No. 10 84 0854.3.
Chinese Office Action dated Apr. 3, 2014 from related Chinese Application No. 201080059610.9, together with an English language translation.

* cited by examiner

FIG. 8

| G2(0,0) | B2(1,0) | G2(2,0) | B2(3,0) | G2(4,0) | B2(5,0) |
|---------|---------|---------|---------|---------|---------|
| B2(0,1) | G2(1,1) | B2(2,1) | G2(3,1) | B2(4,1) | G2(5,1) |
| G2(0,2) | B2(1,2) | G2(2,2) | B2(3,2) | G2(4,2) | B2(5,2) |
| B2(0,3) | G2(1,3) | B2(2,3) | G2(3,3) | B2(4,3) | G2(5,3) |

MULTIPLE RESOLUTION-TRANSFORMED IMAGE

ENDOSCOPIC IMAGE
(LUMINANCE SIGNAL)

ENDOSCOPIC IMAGE
(AFTER MULTIPLE RESOLUTION TRANSFORMATION)

IMAGE PROCESSING DEVICE, ELECTRONIC APPARATUS, INFORMATION STORAGE DEVICE, AND IMAGE PROCESSING METHOD

CROSS REFERENCE TO RELATED APPLICATION

This application is a continuation of International Patent Application No. PCT/JP2010/071963, having an international filing date of Dec. 8, 2010, which designated the United States, the entirety of which is incorporated herein by reference. Japanese Patent Application No. 2009-296964 filed on Dec. 28, 2009 is also incorporated herein by reference in its entirety.

BACKGROUND

The present invention relates to an image processing device, an electronic apparatus, an information storage device, an image processing method, and the like.

A frame-sequential endoscope system has been widely used. The frame-sequential endoscope system sequentially applies three colors of light (R1, G1, and B1) to tissue in a body cavity using a rotary filter, and allows the user to perform diagnosis using an image (normal light image) generated from reflected light images. An endoscope system has been proposed that sequentially applies two types of narrow-band light (G2 and B2) that differs in characteristics from the three colors of light to tissue in a body cavity, and allows the user to perform diagnosis using a narrow-band light image generated from reflected light images (see JP-A-2006-68113, for example). An endoscope system has also been proposed that applies narrow-band excitation light to tissue in a body cavity, and allows the user to perform diagnosis using a fluorescent image generated by acquiring intrinsic fluorescence produced by the tissue or fluorescence produced by a fluorescent agent due to the excitation light (see JP-A-2007-229053, for example).

When performing diagnosis using an endoscope system that acquires a narrow-band light image (e.g., JP-A-2006-68113), a lesion area (e.g., epidermoid cancer) that is difficult to observe in a normal light image is visualized as a brown area differing from a normal area. Therefore, a lesion area can be easily found using such an endoscope system.

When performing diagnosis using an endoscope system that acquires a fluorescent image (e.g., JP-A-2007-229053), only a lesion area (e.g., tumor) produces fluorescence by utilizing a fluorescent agent that is specifically accumulated in such a lesion area. Therefore, a lesion area can be easily found using such an endoscope system.

SUMMARY

According to one aspect of the invention, there is provided an image processing device comprising:

a first image acquisition section that acquires a first image that includes an object image including information within a wavelength band of white light;

a second image acquisition section that acquires a second image that includes an object image including information within a specific wavelength band;

a type determination section that determines a type of the object image in the second image based on a feature quantity of each pixel included in the second image; and a highlight section that performs a highlight process on the first image based on the type of the object image determined by the type determination section.

According to another aspect of the invention, there is provided an electronic apparatus comprising:

the image processing device.

According to another aspect of the invention, there is provided an image processing device comprising:

a first image acquisition section that acquires a first image that includes an object image including information within a wavelength band of white light;

a second image acquisition section that acquires a second image that includes an object image including information within a specific wavelength band; and a highlight section that performs a highlight process on the first image based on a type of the second image acquired by the second image acquisition section.

According to another aspect of the invention, there is provided an information storage device storing a program that causes a computer to function as:

a first image acquisition section that acquires a first image that includes an object image including information within a wavelength band of white light;

a second image acquisition section that acquires a second image that includes an object image including information within a specific wavelength band;

a type determination section that determines a type of the object image in the second image based on a feature quantity of each pixel included in the second image; and a highlight section that performs a highlight process on the first image based on the type of the object image determined by the type determination section.

According to another aspect of the invention, there is provided an information storage device storing a program that causes a computer to function as:

a first image acquisition section that acquires a first image that includes an object image including information within a wavelength band of white light;

a second image acquisition section that acquires a second image that includes an object image including information within a specific wavelength band; and a highlight section that performs a highlight process on the first image based on a type of the second image acquired by the second image acquisition section.

According to another aspect of the invention, there is provided an image processing method comprising:

acquiring a first image that includes an object image including information within a wavelength band of white light;

acquiring a second image that includes an object image including information within a specific wavelength band;

determining a type of the object image in the second image based on a feature quantity of each pixel included in the second image; and performing a highlight process on the first image based on the determined type of the object image.

According to another aspect of the invention, there is provided an image processing method comprising:

acquiring a first image that includes an object image including information within a wavelength band of white light;

acquiring a second image that includes an object image including information within a specific wavelength band; and performing a highlight process on the first image based on a type of the acquired second image.

BRIEF DESCRIPTION OF THE DRAWINGS

FIG. 8 is a view illustrating color filters g2 and b2.

DESCRIPTION OF EXEMPLARY EMBODIMENTS

Figure 1:
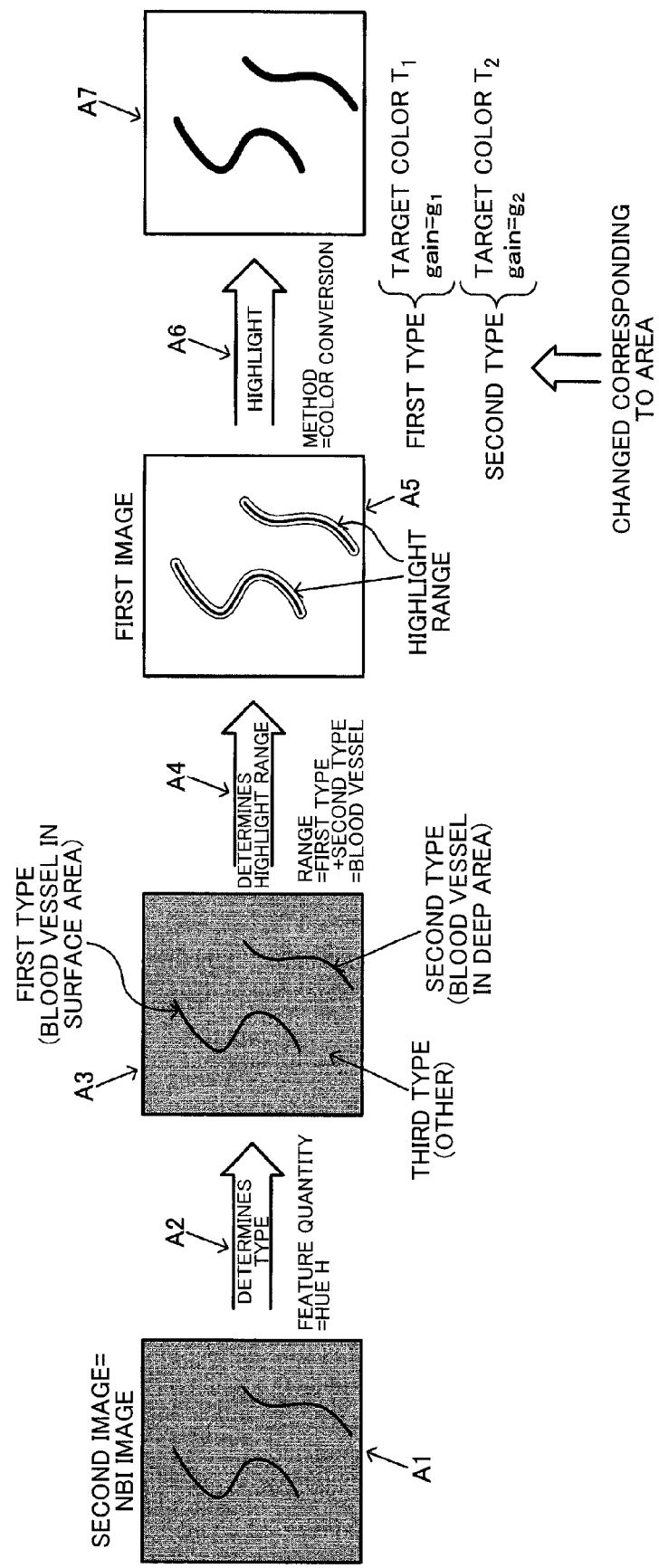
FIG. 1 is a view illustrating a type determination process and a highlight process.

According to one embodiment of the invention, there is provided an image processing device comprising:

a first image acquisition section that acquires a first image that includes an object image including information within a wavelength band of white light;

a second image acquisition section that acquires a second image that includes an object image including information within a specific wavelength band;

a type determination section that determines a type of the object image in the second image based on a feature quantity of each pixel included in the second image; and a highlight section that performs a highlight process on the first image based on the type of the object image determined by the type determination section.

According to above embodiment of the invention, the first image that corresponds to the wavelength band of the white light and the second image that corresponds to the specific wavelength band are acquired. The type of the object image in the second image is determined, and the highlight process is performed on the first image based on the type of the object image. This makes it possible to perform various highlight processes corresponding to the situation.

According to another embodiment of the invention, there is provided an image processing device comprising:

a first image acquisition section that acquires a first image that includes an object image including information within a wavelength band of white light;

a second image acquisition section that acquires a second image that includes an object image including information within a specific wavelength band; and a highlight section that performs a highlight process on the first image based on a type of the second image acquired by the second image acquisition section.

According to above embodiment of the invention, the first image that corresponds to the wavelength band of the white light and the second image that corresponds to the specific wavelength band are acquired, and the highlight process is performed on the first image based on the second image. This makes it possible to perform various highlight processes corresponding to the situation even if the second image may be classified into a plurality of types.

According to another embodiment of the invention, there is provided an electronic apparatus comprising:

the image processing device.

According to another embodiment of the invention, there is provided an information storage device storing a program that causes a computer to function as above sections.

According to another embodiment of the invention, there is provided an image processing method comprising:

acquiring a first image that includes an object image including information within a wavelength band of white light;

acquiring a second image that includes an object image including information within a specific wavelength band;

determining a type of the object image in the second image based on a feature quantity of each pixel included in the second image; and performing a highlight process on the first image based on the determined type of the object image.

According to another embodiment of the invention, there is provided an image processing method comprising:

acquiring a first image that includes an object image including information within a wavelength band of white light;

acquiring a second image that includes an object image including information within a specific wavelength band; and performing a highlight process on the first image based on a type of the acquired second image.

Exemplary embodiments of the invention are described below. Note that the following exemplary embodiments do not in any way limit the scope of the invention laid out in the claims. Note also that all of the elements of the following exemplary embodiments should not necessarily be taken as essential elements of the invention.

1. First Embodiment

An outline of a first embodiment of the invention is described below with reference to FIG. 1.

Several aspects and embodiments of the invention propose a method that changes a highlight process performed on a first image depending on the type of object image within a second image. In the first embodiment, a second image is an NBI (narrow band imaging) image (see A1). The type of an object image in the second image is determined (A2). In the example illustrated in FIG. 1, the hue H is used as a feature quantity for determining the type of the object image. An object image having a hue H of 5 to 35 is determined to be a first type of object image, and an object image having a hue H of 170 to 200 is determined to be a second type of object image (see A3). An object image other than the first type of object image and the second type of object image is determined to be a third type of object image. The first type of object image corresponds to a blood vessel in a surface area, and the second type of object image corresponds to a blood vessel in a deep area. The third type of object image corresponds to an area (e.g., mucous membrane) other than a blood vessel in a surface area and a blood vessel in a deep area.

A highlight range is determined after determining the type of the object image. In the first embodiment, the highlight range corresponds to the first type and the second type (i.e., a blood vessel in a surface area and a blood vessel in a deep area) (A4). Therefore, the first image (normal light image in a narrow sense) is highlighted as indicated by A5.

A highlight process is performed on the highlight range using a given method. In the first embodiment, the highlight process is implemented using a color conversion process (see A6). The color conversion process is performed using expressions (9) and (10). The highlight process corresponding to the type of the object image can be performed by changing the target color and the gain parameter depending on the type (first type or second type) of object image. A normal light image in which the blood vessel is highlighted (see A7) can thus be acquired. Since the first type of object image and the second type of object image differ in target color, a blood vessel in a surface area and a blood vessel in a deep area are displayed in a different color.

The method of performing the highlight process may be changed corresponding to the organ to be observed.

Figure 2:
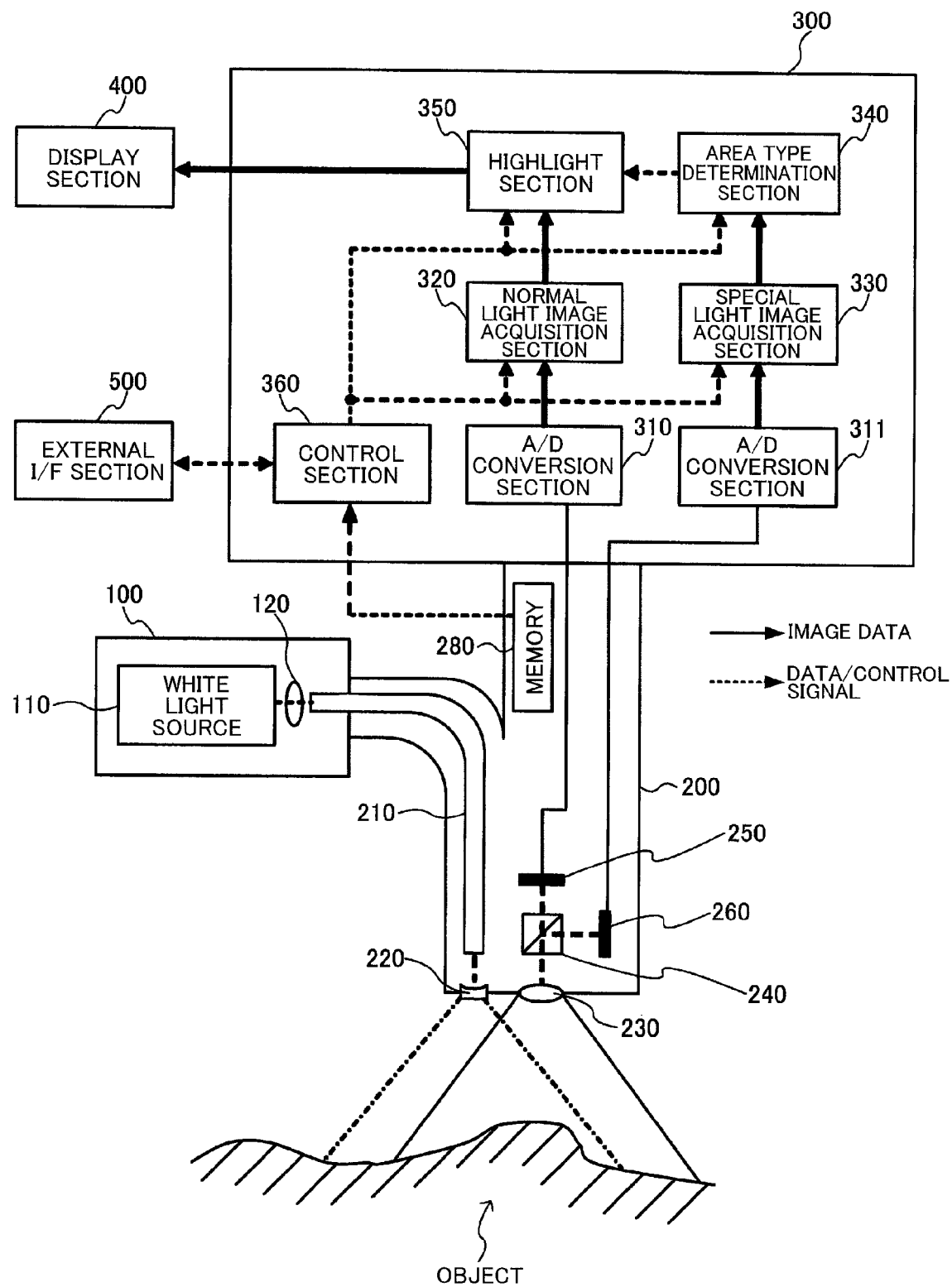
FIG. 2 illustrates a system configuration example according to one embodiment of the invention.

An endoscope system according to the first embodiment is described below with reference to FIG. 2. The endoscope system according to the first embodiment includes a light source section 100, an imaging section 200, an image processing section 300, a display section 400, and an external I/F section 500.

The light source section 100 includes a white light source 110 that emits white light, and a condenser lens 120 that focuses the white light emitted from the white light source 110 on a light guide fiber 210.

The imaging section 200 is formed to be elongated and flexible (i.e., can be curved) so that the imaging section 200 can be inserted into a body cavity or the like.

The imaging section 200 can be removed so that a different imaging section can be used depending on the organ to be observed. The imaging section 200 is normally referred to as "scope" in the field of endoscopy. Specific examples of the scope include an upper gastrointestinal scope, a lower gastrointestinal scope, and the like.

Figure 4:
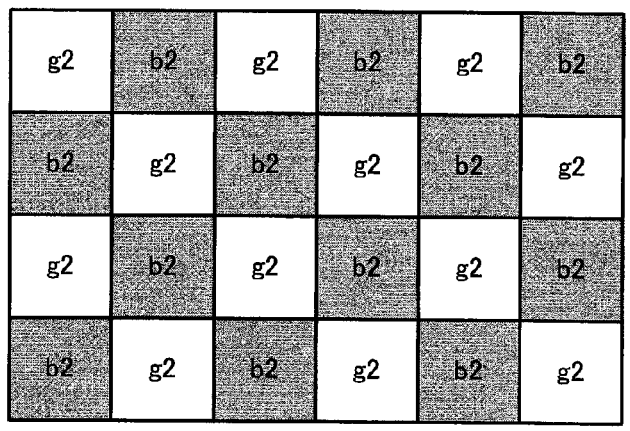
FIG. 4 is a view illustrating color filters g2 and b2.
Figure 5:
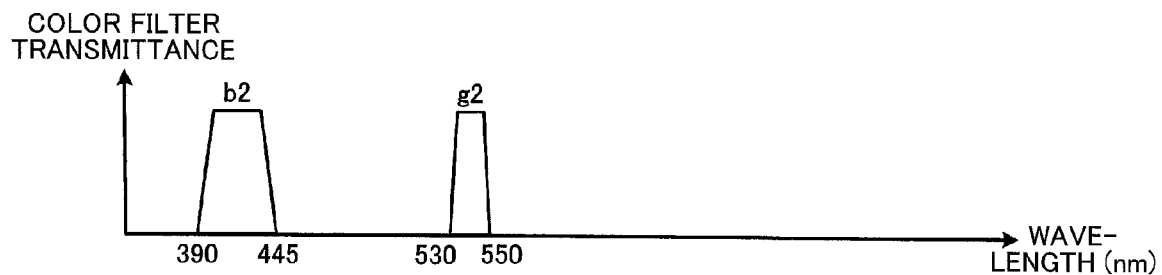
FIG. 5 illustrates the spectral characteristics of color filters g2 and b2.

The imaging section 200 includes the light guide fiber 210 that guides light focused by the light source section 100, an illumination lens 220 that diffuses light that has been guided by the light guide fiber 210, and illuminates an object, an objective lens 230 that focuses light reflected by the object, a half mirror 240 that divides (separates) the focused reflected light into two parts, and a first imaging element 250 and a second imaging element 260 that detect the reflected light divided by the half mirror 240. The first imaging element 250 includes a Bayer color filter array that is used to capture a normal light image. For example, color filters R, G, and B of the first imaging element 250 have the spectral characteristics illustrated in FIG. 3. As illustrated in FIG. 4, the second imaging element 260 has a configuration in which color filters g2 and b2 are disposed in a staggered arrangement, for example. As illustrated in FIG. 5, the color filter b2 allows light within a wavelength band of 390 to 445 nm to pass through, and the color filter g2 allows light within a wavelength band of 530 to 550 nm to pass through, for example.

The imaging section 200 includes a memory 280. The memory 280 stores an identification number specific to each scope. The memory 280 is connected to a control section 360. The control section 360 can specify the scope referring to the identification number stored in the memory 280. The control section 360 can also specify the organ to be observed by specifying the scope.

The image processing section 300 includes AD conversion sections 310 and 311, a normal light image acquisition section 320, a special light image acquisition section 330, an area type determination section 340, a highlight section 350, and the control section 360. The control section 360 is connected to the normal light image acquisition section 320, the special light image acquisition section 330, the area type determination section 340, and the highlight section 350, and controls the normal light image acquisition section 320, the special light image acquisition section 330, the area type determination section 340, and the highlight section 350.

The external I/F section 500 is an interface that allows the user to perform an input operation or the like on the image processing device. The external I/F section 500 includes a power switch (power ON/OFF switch), a shutter button (capture operation start button), a mode (e.g., imaging mode) change button, and the like. The external I/F section 500 outputs input information to the control section 360.

The AD conversion section 310 converts an analog image signal output from the first imaging element 250 into a digital image signal, and outputs the digital image signal. The AD conversion section 311 converts an analog image signal output from the second imaging element 260 into a digital image signal, and outputs the digital image signal.

The normal light image acquisition section 320 acquires a normal light image from the digital image signal output from the AD conversion section 310. The special light image acquisition section 330 acquires a special light image from the digital image signal output from the A/D conversion section 311. The details of the normal light image acquisition section 320 and the special light image acquisition section 330 are described later.

The normal light image acquired by the normal light image acquisition section 320 is output to the highlight section 350. The special light image acquired by the special light image acquisition section 330 is output to the area type determination section 340. The area type determination section 340 determines the type of the object in the special light image, and outputs the determination result to the highlight section 350. The highlight section 350 performs a highlight process on the normal light image corresponding to the determination result output from the area type determination section 340, and outputs the resulting normal light image to the display section 400. The details of the area type determination section 340 and the highlight section 350 are described later.

Figure 6:
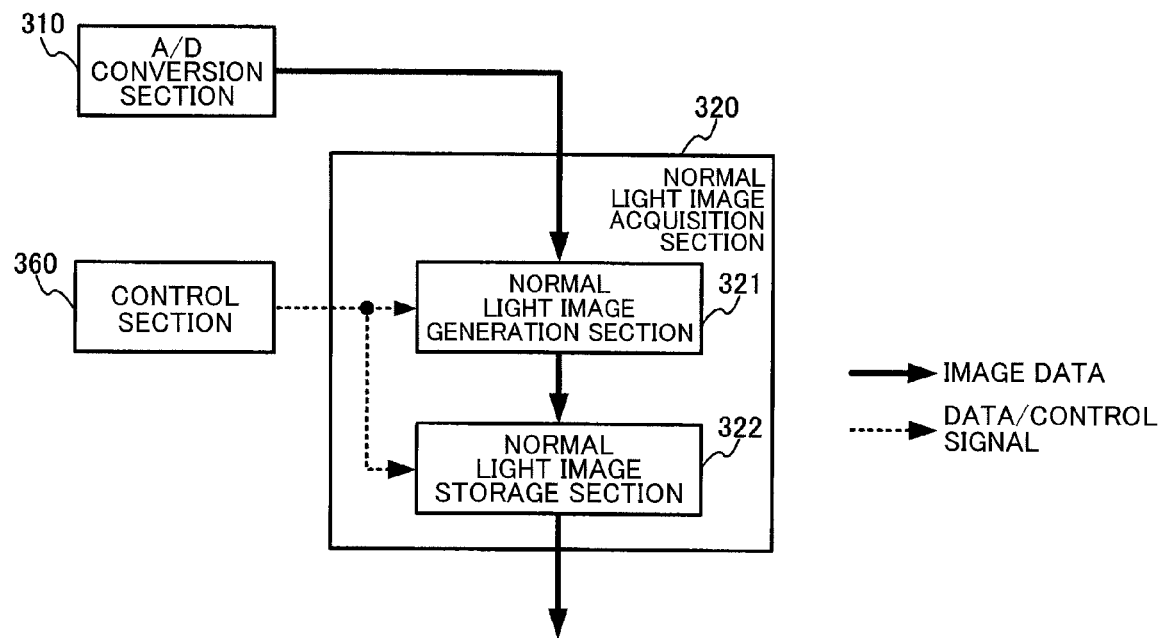
FIG. 6 illustrates a configuration example of a normal light image acquisition section.

The details of the normal light image acquisition section 320 are described below with reference to FIG. 6. The normal light image acquisition section 320 includes a normal light image generation section 321 and a normal light image storage section 322. The normal light image generation section 321 performs image processing on the digital image signal output from the AD conversion section 310 to generate a normal light image. More specifically, the normal light image generation section 321 performs an interpolation process, a white balance process, a color conversion process, a grayscale transformation process, and the like on the digital image signal to generate a normal light image, and outputs the normal light image. The normal light image is an RGB image. The normal light image storage section 322 stores the normal light image output from the normal light image generation section 321 in a memory.

Figure 7:
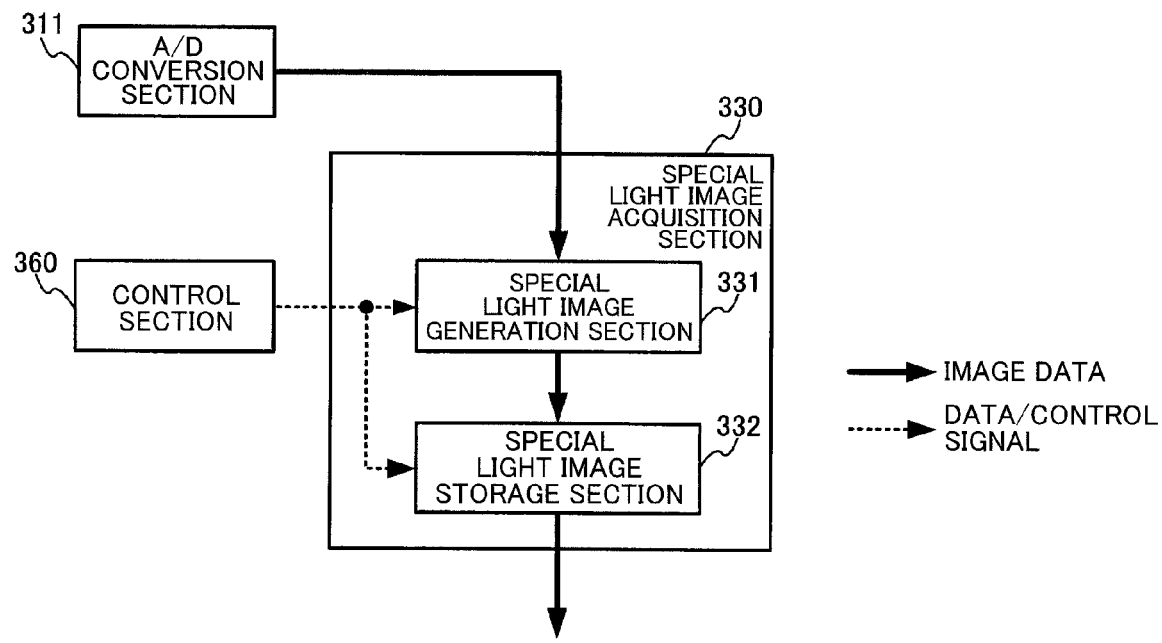
FIG. 7 illustrates a configuration example of a special light image acquisition section.

The details of the special light image acquisition section 330 are described below with reference to FIG. 7. The special light image acquisition section 330 includes a special light image generation section 331 and a special light image storage section 332. The special light image generation section 331 performs image processing on the digital image signal output from the A/D conversion section 311 to generate a special light image. In the first embodiment, the special light image is a narrow-band light image. The narrow-band light image is an RGB image.

The special light image generation section 331 generates the narrow-band light image as described below. The second imaging element 260 has a configuration in which the color filters g2 and b2 are disposed in a staggered arrangement (see FIG. 4). Therefore, digital image signals illustrated in FIG. 8 are input to the special light image generation section 331. Note that G2(x, y) indicates the signal value of the g2 filter, and B2(x, y) indicates the signal value of the b2 filter. x and y are image coordinate values. The special light image generation section 331 performs an interpolation process on the image signals to generate a G2 image in which each pixel has the signal value of the filter g2, and a B2 image in which each pixel has the signal value of the filter b2. The signal value calculated by the interpolation process may be the average value of the signal values of four peripheral pixels. For example, the signal value B2(1, 1) of the filter b2 at the position G2(1, 1) and the pixel value G2(1, 2) of the filter g2 at the position B2(1, 2) illustrated in FIG. 8 are calculated by the following expressions (1) and (2).

$$B2(1,1) = [B2(0, 1) + B2(1, 0) + B2(1, 2) + B2(2, 1)]/4 \quad (1)$$

$$G2(1, 2) = [G2(0, 2) + G2(1, 1) + G2(1, 3) + G2(2, 2)]/4 \quad (2)$$

A color image having R, G, and B signal values is generated from the G2 image and the B2 image generated by the interpolation process. The color image is generated by inputting the signal value G2(x, y) to the R signal at the coordinates (x, y), and inputting the signal value B2(x, y) to the G and B signals at the coordinates (x, y). The special light image generation section 331 performs a white balance process, a grayscale transformation process, and the like on the generated color image to generate a narrow-band light image. The narrow-band light image thus generated is output to the special light image storage section 332. The special light image storage section 332 stores the narrow-band light image output from the special light image generation section 331 in a memory.

Figure 9:
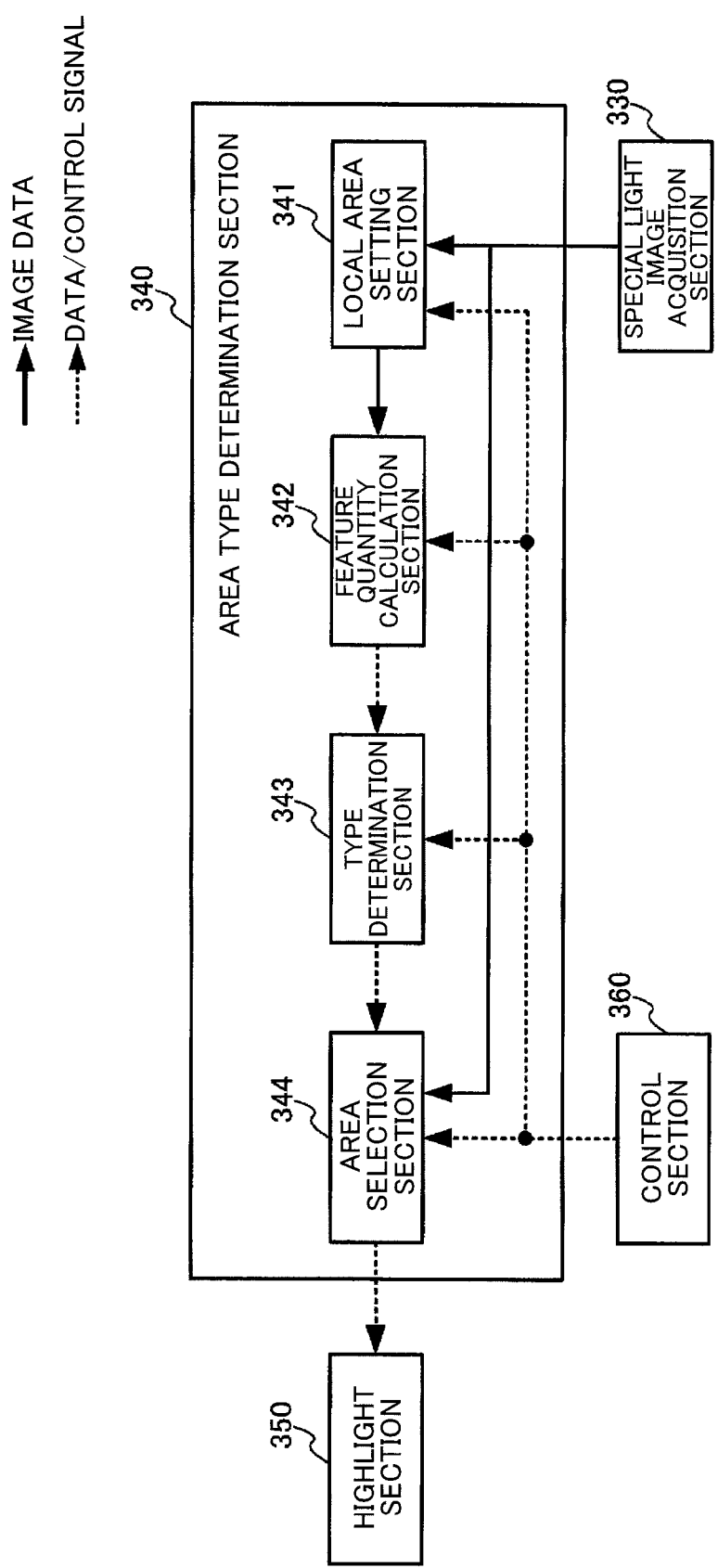
FIG. 9 illustrates a configuration example of an area type determination section.

The details of the area type determination section 340 are described below. FIG. 9 is a block diagram illustrating an example of the configuration of the area type determination section 340 according to the first embodiment. The area type determination section 340 includes a local area setting section 341, a feature quantity calculation section 342, a type determination section 343, and an area selection section 344. The control section 360 is connected to the local area setting section 341, the feature quantity calculation section 342, the type determination section 343, and the area selection section 344, and controls the local area setting section 341, the feature quantity calculation section 342, the type determination section 343, and the area selection section 344.

Figure 10:
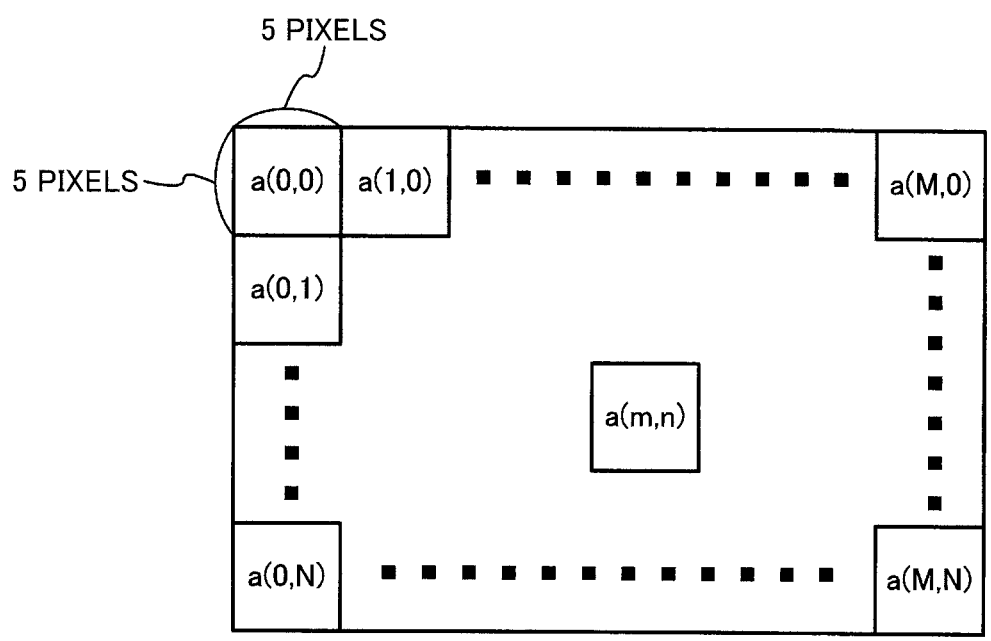
FIG. 10 is a view illustrating a local area setting method.

The local area setting section 341 sets a plurality of local areas within the narrow-band light image output from the special light image acquisition section 330. For example, the local area setting section 341 divides the narrow-band light image into a plurality of rectangular areas, and sets the plurality of rectangular areas as the local areas. For example, the local area setting section 341 sets a 5×5 pixel area as one local area (see FIG. 10). The narrow-band light image includes M×N local areas, and the coordinates of each local area are indicated by (m, n). The local area positioned at the coordinates (m, n) is indicated by a(m, n). The coordinates of the local area positioned at the upper left of the image are indicated by (0, 0). The rightward direction is the positive direction of the coordinate value m, and the downward direction is the positive direction of the coordinate value n. Note that the local area need not necessarily be rectangular. The narrow-band light image may be divided into a plurality of arbitrary polygonal areas, and the plurality of polygonal areas may be set as the local areas. The local areas may be arbitrarily set based on instructions from the user. In the first embodiment, each local area includes a plurality of adjacent pixels in order to reduce the amount of calculations. Note that one pixel may be set as one local area. In this case, the subsequent process is performed in the same manner as in the case where each local area includes a plurality of adjacent pixels.

The feature quantity calculation section 342 calculates the feature quantity of each local area set by the local area setting section 341. A case where hue is used as the feature quantity is described below.

The hue of the local area a(m, n) is indicated by H(m, n). When calculating the hue H(m, n), the average values R_ave, G_ave, and B_ave of the R, G, and B signals in each local area are calculated. The average value R_ave is the average value of the R signal of each pixel included in each local area. The average value G_ave is the average value of the G signal of each pixel included in each local area, and the average value B_ave is the average value of the B signal of each pixel included in each local area. The signal value is indicated by 8 bits (0 to 255). The hue H(m, n) of each local area is calculated by the following expressions (3) to (8) using the average values R_ave, G_ave, and B_ave, for example.

$$\text{Max}=\text{MAX}(R\_ave, G\_ave, B\_ave) \quad (3)$$

The MAX function outputs the maximum argument among a plurality of arguments.

When max is 0:

$$H=0 \quad (4)$$

When max is not 0:

$$d=\text{MAX}(R\_ave, G\_ave, B\_ave)-\text{MIN}(R\_ave, G\_ave, B\_ave) \quad (5)$$

The MIN function outputs the minimum argument among a plurality of arguments.

When the average value R_ave is a maximum among the average values R_ave, G_ave, and B_ave:

$$H=60*(G\_ave-B\_ave)/d \quad (6)$$

When the average value G_ave is a maximum among the average values R_ave, G_ave, and B_ave:

$$H=60*\{2+(B\_ave-R\_ave)\}/d \quad (7)$$

When the average value B_ave is a maximum among the average values R_ave, G_ave, and B_ave:

$$H=60*\{4+(R\_ave-G\_ave)\}/d \quad (8)$$

When the hue H is smaller than 0, 360 is added to the hue H. The hue H is considered to be 0 when the hue H is 360.

The type determination section 343 determines the type of the object in each local area using the hue H calculated for each local area, and outputs the determination result to the area selection section 344.

When light emitted from the light source section 100 is applied to tissue (i.e., object), short-wavelength light is reflected near the surface of the tissue, while long-wavelength light reaches a deep area of the tissue. The color filter b2 used for the imaging element that captures the narrow-band light image allows light within a wavelength band of 390 to 445 nm to pass through, and the color filter g2 used for the imaging element that captures the narrow-band light image allows light within a wavelength band of 530 to 550 nm to pass through. Therefore, short-wavelength light reflected by a surface area (layer) of the tissue passes through the b2 filter, and long-wavelength light reflected by a deep area (layer) of the tissue passes through the g2 filter. Light within the passband of each color filter is easily absorbed by hemoglobin that is abundantly contained in blood. Therefore, a blood vessel in the surface area of the tissue is drawn in the B2 image, and a blood vessel in the deep area of the tissue is drawn in the G2 image.

When generating a color image from the B2 image and the G2 image, the signal value G2(x, y) is input to the R signal at the coordinates (x, y), and the signal value B2(x, y) is input to the G and B signals at the coordinates (x, y). Therefore, the R signal of the narrow-band light image includes information about a blood vessel in the deep area of the tissue, and the G and B signals of the narrow-band light image include information about a blood vessel in the surface area of the tissue.

Therefore, a blood vessel in the surface area of the tissue is drawn in the narrow-band light image as a brown area, and a blood vessel in the deep area of the tissue is drawn in the narrow-band light image as a blue-green area. Specifically, since a blood vessel in the surface area of the tissue and a blood vessel in the deep area of the tissue are drawn to differ in hue, a blood vessel in the surface area of the tissue and a blood vessel in the deep area of the tissue can be discriminated by utilizing the hue H as the feature quantity. For example, an area having a hue H of 5 to 35 may be determined to be a blood vessel in the surface area of the tissue, and an area having a hue H of 170 to 200 may be determined to be a blood vessel in the deep area of the tissue.

The type determination section 343 outputs the coordinates of each local area that has been set by the local area setting section 341 and determined to be a blood vessel in the surface area of the tissue or a blood vessel in the deep area of the tissue, and tag information that indicates the local area type determination result to the area selection section 344. The tag value may be set to "1" when the local area has been determined to be a blood vessel in the surface area of the tissue, and may be set to "2" when the local area has been determined to be a blood vessel in the deep area of the tissue, for example.

The area selection section 344 calculates the position of each pixel included in each local area from the coordinates of the local area a(m, n) that has been determined to be a blood vessel in the surface area of the tissue or a blood vessel in the deep area of the tissue by the type determination section 343, and information about each pixel included in each local area, adds the tag information to the calculated pixel position information, and outputs the pixel position information to the highlight section 350.

The details of the highlight section 350 are described below. The highlight section 350 performs the highlight process on each pixel of the normal light image that corresponds to the pixel position output from the area type determination section 340. The highlight process on a pixel (tag value: 1) that has been determined to be a blood vessel in the surface area of the tissue may be implemented by a color conversion process shown by the following expression (9), and the highlight process on a pixel (tag value: 2) that has been determined to be a blood vessel in the deep area of the tissue may be implemented by a color conversion process shown by the following expression (10), for example.

$$R\_out(x, y)=\text{gain}*R(x, y)+(1-\text{gain})*T\_R1$$

$$G\_out(x, y)=\text{gain}*G(x, y)+(1-\text{gain})*T\_G1$$

$$B\_out(x, y)=\text{gain}*B(x, y)+(1-\text{gain})*T\_B1 \quad (9)$$

$$R\_out(x, y)=\text{gain}*R(x, y)+(1-\text{gain})*T\_R2$$

$$G\_out(x, y)=\text{gain}*G(x, y)+(1-\text{gain})*T\_G2$$

$$B\_out(x, y)=\text{gain}*B(x, y)+(1-\text{gain})*T\_B2 \quad (10)$$

where, R(x, y), G(x, y), and B(x, y) are the RGB signal values at the coordinates (x, y) of the normal light image before the color conversion process, R_out(x, y), G_out(x, y), and B_out(x, y) are the RGB signal values at the coordinates (x, y) of the normal light image after the color conversion process, T_R1, T_G1, and T_B1 are the RGB signal values of the target color of a blood vessel in the surface area of the tissue, and T_R2, T_G2, and T_B2 are the RGB signal values of the target color of a blood vessel in the deep area of the tissue. A blood vessel in the surface area of the tissue and a blood vessel in the deep area of the tissue can be drawn in a different color by setting a different value as the target color. gain is an arbitrary coefficient in the range of 0 to 1.

Note that the target colors T_R1, T_G1, and T_B1 of a blood vessel in the surface area of the tissue, the target colors T_R2, T_G2, and T_B2 of a blood vessel in the deep area of the tissue, and the gain parameter may be set by the user via the external I/F section 500, or different parameters may be set in advance corresponding to the organ to be observed. The control section 360 may specify the organ to be observed referring to the identification number specific to each scope stored in the memory 280, or the user may designate the organ to be observed via the external I/F section 500.

Since a blood vessel in the surface area of the tissue and a blood vessel in the deep area of the tissue are drawn in a different color by performing the above process, a blood vessel in the surface area of the tissue and a blood vessel in the deep area of the tissue can be easily discriminated. This makes it possible to prevent a situation in which a lesion area is missed while reducing the burden on the doctor during diagnosis using the normal light image and the narrow-band light image.

Although an example in which the highlight process is independently performed on an area determined to be a blood vessel in the surface area of the tissue and an area determined to be a blood vessel in the deep area of the tissue has been described above, the invention is not limited thereto. For example, only a blood vessel in the surface area of the tissue or a blood vessel in the deep area of the tissue may be highlighted.

The above configuration may be implemented by assigning a priority to the type of object (e.g., a blood vessel in the surface area of the tissue and a blood vessel in the deep area of the tissue) in advance, and determining the method of performing the highlight process corresponding to the type of object with the highest priority when the area type determination section 340 has detected a plurality of types of object.

For example, when a tumor has been found during diagnosis of the large intestine, information about the blood vessel structure on the surface of the tumor is important for determining whether the tumor is benign or malignant. Therefore, a high priority is assigned to a blood vessel in the surface area of the tissue during diagnosis of the large intestine. This makes it possible to perform the highlight process on only an area determined to be a blood vessel in the surface area of the tissue even when the area type determination section 340 has detected a plurality of types of object. This improves the visibility of a blood vessel in the surface area of the tissue, and prevents a situation in which a lesion area is missed.

A disease such as an esophageal varix may be found during diagnosis of the gullet. Since an esophageal varix is present in a relatively deep area of the tissue, information about a blood vessel in the deep area of the tissue is important for diagnosis. Therefore, a high priority is assigned to a blood vessel in the deep area of the tissue during diagnosis of the gullet. This makes it possible to perform the highlight process on only an area determined to be a blood vessel in the deep area of the tissue. This improves the visibility of a blood vessel in the deep area of the tissue, and is effective for preventing a situation in which an esophageal varix is missed.

The priority may be set by the user via the external I/F section 500, or may be set in advance corresponding to the organ to be observed. The control section 360 may specify the organ to be observed referring to the identification number specific to each scope stored in the memory 280, or the user may designate the organ to be observed via the external I/F section 500.

The highlight process performed by the highlight section 350 may be implemented using an arbitrary luminance conversion process or an arbitrary color conversion process instead of the above color conversion process.

Although an example in which each section included in the image processing section 300 is implemented by hardware has been described above, the configuration is not limited thereto. For example, a CPU may perform the process of each section on an image acquired in advance using an imaging element such as a capsule endoscope. Specifically, the process of each section may be implemented by software by causing the CPU to execute a program. Alternatively, the process of each section may partially be implemented by software.

When separately providing an imaging section, and implementing the process of each section included in the image processing section 300 by software, a known computer system (e.g., work station or personal computer) may be used as the image processing device. A program (image processing program) that implements the process of each section included in the image processing section 300 may be provided in advance, and executed by the CPU of the computer system.

Figure 11:
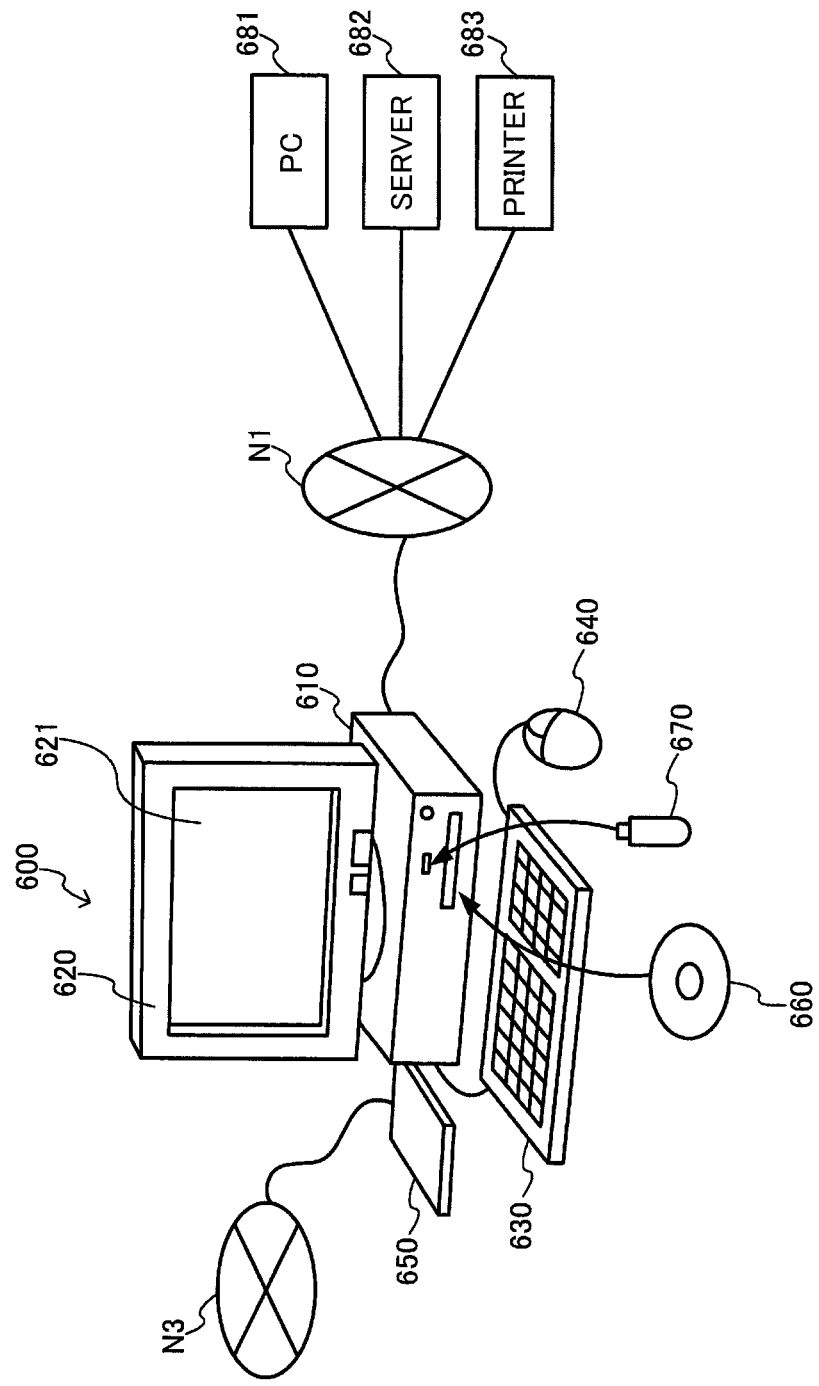
FIG. 11 illustrates a configuration example of a computer used for a software process.
Figure 12:
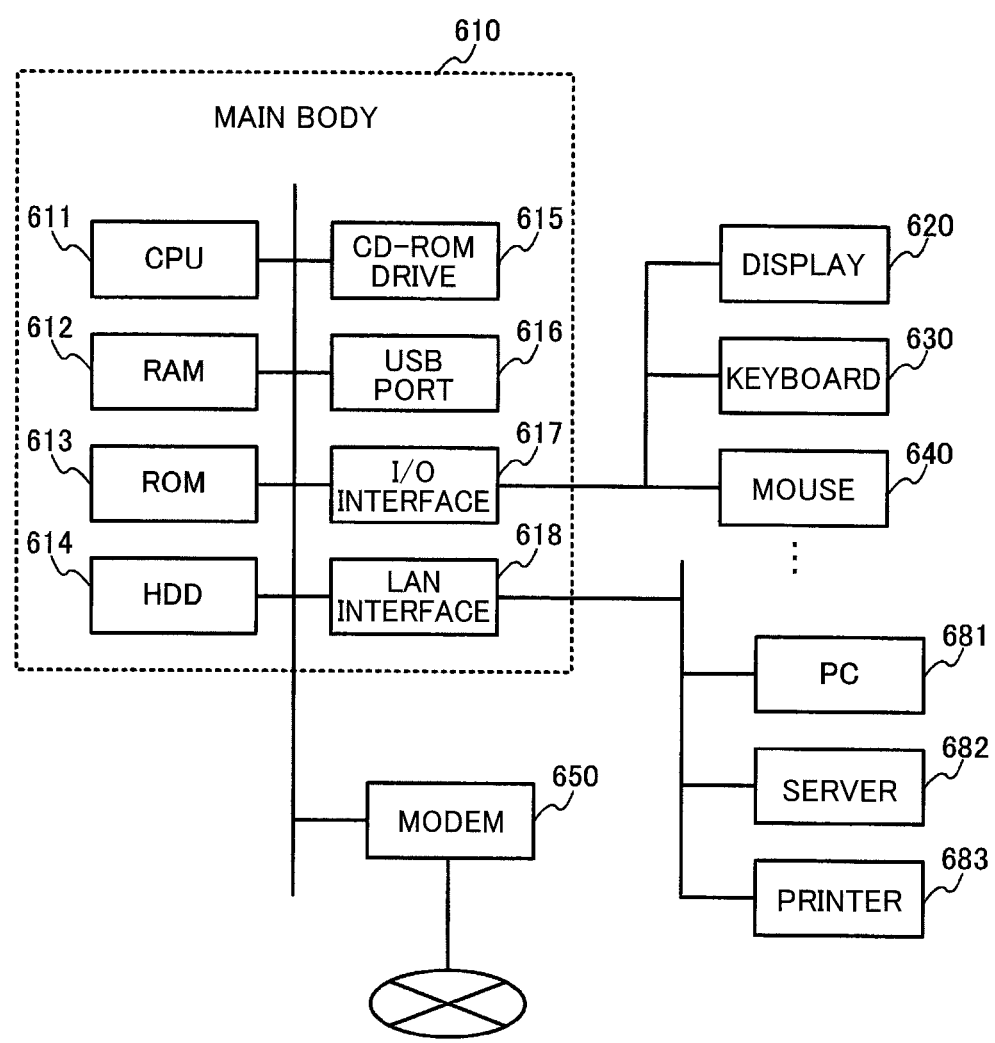
FIG. 12 illustrates a configuration example of a computer used for a software process.

FIG. 11 is a system configuration diagram illustrating the configuration of a computer system 600 according to a modification. FIG. 12 is a block diagram illustrating the configuration of a main body 610 of the computer system 600. As illustrated in FIG. 11, the computer system 600 includes the main body 610, a display 620 that displays information (e.g., image) on a display screen 621 based on instructions from the main body 610, a keyboard 630 that allows the user to input information to the computer system 600, and a mouse 640 that allows the user to designate an arbitrary position on the display screen 621 of the display 620.

As illustrated in FIG. 12, the main body 610 of the computer system 600 includes a CPU 611, a RAM 612, a ROM 613, a hard disk drive (HDD) 614, a CD-ROM drive 615 that receives a CD-ROM 660, a USB port 616 to which a USB memory 670 is removably connected, an I/O interface 617 that connects the display 620, the keyboard 630, and the mouse 640, and a LAN interface 618 that is used to connect to a local area network or a wide area network (LAN/WAN) N1.

The computer system 600 is connected to a modem 650 that is used to connect to a public line N3 (e.g., Internet). The computer system 600 is also connected to personal computer (PC) 681 (i.e., another computer system), a server 682, a printer 683, and the like via the LAN interface 618 and the local area network or the large area network N1.

The computer system 600 implements the functions of the image processing device by reading an image processing program (e.g., an image processing program that implements a process described below with reference to FIGS. 13 and 14) recorded on a given recording medium, and executing the image processing program. The given recording medium may be an arbitrary recording medium that records the image processing program that can be read by the computer system 600, such as the CD-ROM 660, the USB memory 670, a portable physical medium (e.g., MO disk, DVD disk, flexible disk (FD), magnetooptical disk, or IC card), a stationary physical medium (e.g., HDD 614, RAM 612, or ROM 613)

that is provided inside or outside the computer system 600, or a communication medium that temporarily stores a program during transmission (e.g., the public line N3 connected via the modem 650, or the local area network or the wide area network N1 to which the computer system (PC) 681 or the server 682 is connected).

Specifically, the image processing program is recorded on a recording medium (e.g., portable physical medium, stationary physical medium, or communication medium) so that the image processing program can be read by a computer. The computer system 600 implements the functions of the image processing device by reading the image processing program from such a recording medium, and executing the image processing program. Note that the image processing program need not necessarily be executed by the computer system 600. The invention may similarly be applied to the case where the computer system (PC) 681 or the server 682 executes the image processing program, or the computer system (PC) 681 and the server 682 execute the image processing program in cooperation.

A process performed on the normal light image and the narrow-band light image acquired in advance when implementing the process of the area type determination section 340 and the process of the highlight section 350 illustrated in FIG. 2 by software is described below using a flowchart illustrated in FIG. 13.

Specifically, the narrow-band light image is written into the memory (Step 1), and the normal light image acquired at the same time with the narrow-band light image is then written into the memory (Step 2). The type of the object is determined using the narrow-band light image (Step 3). The details of the area type determination step (Step 3 ) are described later. The highlight process is performed on the normal light image corresponding to the determination result, and the image obtained by the highlight process is output as a display image (Step 4). The highlight process is performed using the expressions (9) and (10). The process ends when all of the images have been processed. The process is repeated until all of the images have been processed (Step 5).

Figure 13:
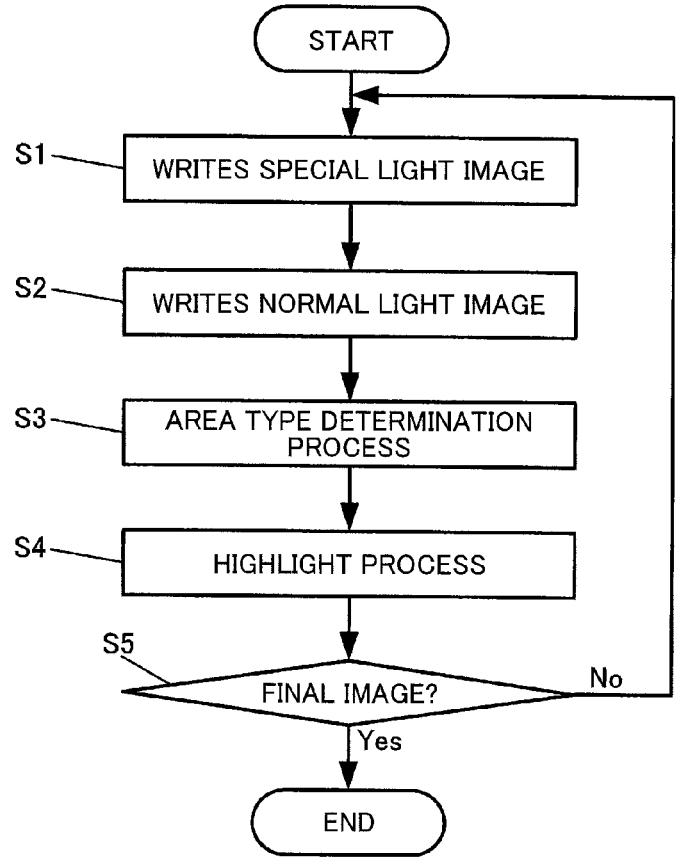
FIG. 13 is a flowchart illustrating a process according to one embodiment of the invention.
Figure 14:
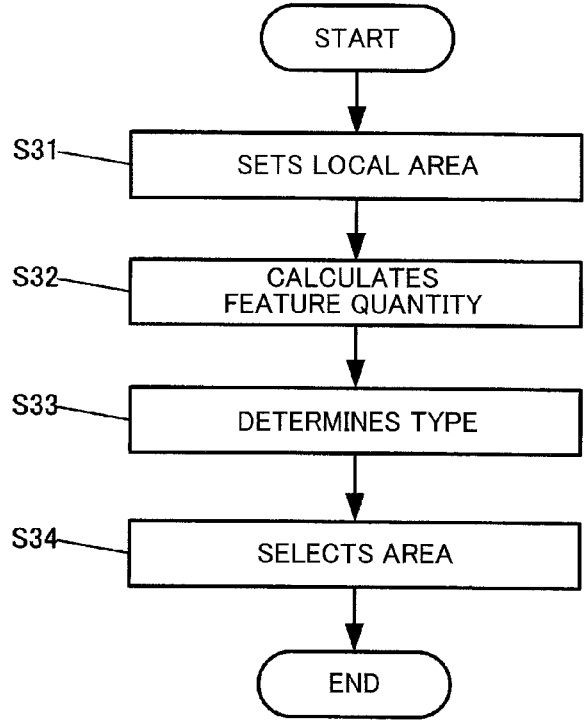
FIG. 14 is a flowchart illustrating an area type determination process.

A specific process of the area type determination step (Step 3) illustrated in FIG. 13 is described below using a flowchart illustrated in FIG. 14. In a local area setting step, a plurality of local areas are set within the narrow-band light image (see FIG. 10) (Step 31). The feature quantity of each local area is calculated (Step 32). For example, the hue H indicated by the expressions (3) to (8) is used as the feature quantity. A type determination process is performed based on the hue H calculated for each local area (Step 33). More specifically, an area having a hue H of 5 to 35 is determined to be a blood vessel in the surface area of the tissue, and an area having a hue H of 170 to 200 is determined to be a blood vessel in the deep area of the tissue. The position of each pixel included in each local area is calculated from the coordinates of the local area a(m, n) that has been determined to be a blood vessel in the surface area of the tissue or a blood vessel in the deep area of the tissue, and information about each pixel included in each local area. The tag information that indicates the determination result is added to the calculated pixel position information, and the resulting pixel position information is output (Step 34).

Since a blood vessel in the surface area of the tissue and a blood vessel in the deep area of the tissue are displayed in a different color by performing the above process, a blood vessel in the surface area of the tissue and a blood vessel in the deep area of the tissue can be easily discriminated. This makes it possible to prevent a situation in which a lesion area is missed while reducing the burden on the doctor during diagnosis using the normal light image and the narrow-band light image.

According to the first embodiment, a first image acquisition section (normal light image acquisition section 320 in a narrow sense) acquires a first image (white light image in a narrow sense) that corresponds to the wavelength band of white light, and a second image acquisition section (special light image acquisition section 330 in a narrow sense) acquires a second image (special light image (e.g., narrow-band image or fluorescent image) in a narrow sense) that corresponds to a specific wavelength band (the wavelength band of narrow-band light or fluorescence in a narrow sense). The type determination section 343 determines the type of an object image in the second image using the feature quantity of each pixel included in the second image. The highlight section 350 performs the highlight process on the first image based on the determination result of the type determination section 343.

The term "type of object image" used herein refers to the type of lesion or the type of blood vessel. For example, the first type of object image is a lesion area, and the second type of object image is a normal area. The first type of object image may be a blood vessel in a surface area, the second type of object image may be a blood vessel in a deep area, and the third type of object image may be an area (e.g., mucous membrane) other than a blood vessel.

The feature quantity of each pixel may be the hue H, edge quantity E, signal value (R, G, and B), or the like. The feature quantity is appropriately selected corresponding to the object (i.e., a target subjected to the highlight process).

The above configuration makes it possible to acquire the normal light image (white light image) and the special light image (e.g., NBI image or fluorescent image), and determine the type of the object image in the special light image. The method of performing the highlight process performed on the normal light image can be changed based on the determined type of the object image. Therefore, it is possible to discriminate a lesion area and a normal area, and perform the highlight process on only the lesion area, for example. It is also possible to discriminate a blood vessel in a surface area and a blood vessel in a deep area, and change the method of performing the highlight process between the blood vessel in the surface area and the blood vessel in the deep area, for example.

The highlight section 350 may change the method of performing the highlight process corresponding to an organ to which the object image belongs.

This makes it possible to change the method of performing the highlight process depending on the organ to be observed. For example, when the first type of object image is a blood vessel in a surface area, the second type of object image is a blood vessel in a deep area, and the third type of object image is an area (e.g., mucous membrane) other than a blood vessel, information about a blood vessel in a surface area of a tumor is important for determining whether the tumor is benign or malignant when observing the large intestine. In this case, a blood vessel in a surface area (i.e., first type of object image) may be preferentially highlighted. For example, the color conversion process performed on the first type of object image may set the target color to a color that is easy to observe as compared with the color conversion process performed on the second type of object image. Alternatively, the highlight process may not be performed on the second type of object image.

Information about a blood vessel in a deep area is important for diagnosing an esophageal varix. Therefore, the second type of object image may be preferentially highlighted when observing the gullet.

At least one of the first image and the second image may be captured by an imaging device provided outside the image processing device. In this case, an organ to which the object image belongs is determined based on information about the imaging device.

This makes it possible to use the information about the imaging device as the organ determination means. The imaging device corresponds to an insertion section (scope) of an endoscope, for example. Specific examples of the insertion section (scope) of the endoscope include an upper gastrointestinal scope, a lower gastrointestinal scope, and the like. Since a specific identification number is assigned to each scope, each scope can be specified by storing the identification number in a memory, for example. Since a different scope is used depending on the organ to be observed, the organ to be observed can be specified by specifying the scope.

A plurality of object images may be present in the second image. In this case, the type determination section 343 determines one type among first to Nth (N is an integer equal to or larger than 2) types to which each of the plurality of object images belongs. The highlight section 350 determines the method of performing the highlight process corresponding to the determination result.

This makes it possible to appropriately determine the type of each of a plurality of object images detected at the same time, and determine the method of performing the highlight process corresponding to the determination result.

More specifically, when two blood vessels and a mucous membrane (background) are observed (see A1 in FIG. 1), three object images are present in total. In this case (N=3), the type determination section 343 determines one type among the first to third types to which each of the three object images belongs. As indicated by A3 in FIG. 1, the left blood vessel that is a blood vessel in a surface area is determined to belong to the first type, the right blood vessel that is a blood vessel in a deep area is determined to belong to the second type, and the mucous membrane is determined to belong to the third type. Although an example in which one object image corresponds to one type has been described above, a person having ordinary skill in the art would readily appreciate that a plurality of object images may correspond to one type, or no object image may correspond to a certain type.

The highlight section 350 determines the method of performing the highlight process corresponding to the type to which each object image belongs. For example, a color conversion process using a different parameter may be performed on the object image that belongs to the first type and the object image that belongs to the second type, and the highlight process may not be performed on the object image that belongs to the third type (see A6 in FIG. 1).

A priority corresponding to each type may be set to each of the first to Nth types. The method of performing the highlight process may be determined based on the priority. The highlight section 350 may set the priority corresponding to an organ to which each object image belongs.

This makes it possible to implement the highlight process based on the priority. The priority may be determined based on an organ to which each object image belongs. Specifically, information about a blood vessel in a surface area is important when observing the large intestine, and information about a blood vessel in a deep area is important when observing the gullet. Therefore, a high priority may be set to the type to which a blood vessel in a surface area belongs (i.e., the first type in the example illustrated in FIG. 1) when observing the large intestine, and a high priority may be set to the type to which a blood vessel in a deep area belongs (i.e., the second type in the example illustrated in FIG. 1) when observing the gullet.

The highlight section 350 may perform the highlight process on an object image that belongs to a type with the highest priority using a highlight method corresponding to the type with the highest priority.

This makes it possible to cause an object image that belongs to the type with the highest priority to relatively stand out by performing the highlight process on only the object image that belongs to the type with the highest priority, and not performing the highlight process on the object image that belongs to another type.

The highlight section 350 may perform the highlight process on an object image that belongs to an ith type among the first to Nth types using an ith highlight method, and may perform the highlight process on an object image that belongs to a jth type among the first to Nth types using a jth highlight method.

This makes it possible to perform the highlight process on object images that respectively belong to two or more types among the first to Nth types using the corresponding highlight method. This is effective when information about a blood vessel in a surface area and information about a blood vessel in a deep area are important for diagnosis, for example.

The second image may be classified into a plurality of types. In this case, the method of performing the highlight process is determined corresponding to the type of the object image and the type of the second image. More specifically, when the second image is an NBI image, and the object image is a blood vessel, the highlight process is performed on a corresponding attention area that is an area corresponding to a blood vessel (see FIG. 1).

The term "corresponding attention area" used herein refers to an area that is selected by the area selection section 344 within the first image, and corresponds to the attention area (i.e., an area including the object image) within the second image.

This makes it possible to determine the method of performing the highlight process taking account of the type of the object image and the type of the second image. For example, a blood vessel may be highlighted when the object image is a blood vessel and the second image is an NBI image (see FIG. 1).

The feature quantity may be an edge quantity, hue, intensity, or the like.

This makes it possible to determine the type of the object image using an arbitrary feature quantity corresponding to the object and the like.

The type of the object image may be at least one type among the type of lesion and the type of blood vessel.

This makes it possible to determine whether or not the object image is a blood vessel, whether a blood vessel is a blood vessel in a surface area or a blood vessel in a deep area, or whether or not the object image is a lesion.

The specific wavelength band may be narrower than the wavelength band of the white light. Specifically, the first image and the second image may be an in vivo image, and the specific wavelength band may be the wavelength band of light absorbed by hemoglobin in blood. More specifically, the specific wavelength band may be 390 to 445 nm or 530 to 550 nm.

This makes it possible to observe the structure of a blood vessel in a surface area and a deep area of tissue. A lesion area (e.g., epidermoid cancer) that cannot be easily observed using normal light can be displayed as a brown area or the like by inputting the resulting signal to a given channel (R, G, or B), so that the lesion area can be reliably detected (i.e., a situation in which the lesion area is missed can be prevented). A wavelength band of 390 to 445 nm or 530 to 550 nm is selected from the viewpoint of absorption by hemoglobin and the ability to reach a surface area or a deep area of tissue. Note that the wavelength band is not limited thereto. For example, the lower limit of the wavelength band may decrease by about 0 to 10%, and the upper limit of the wavelength band may increase by about 0 to 10%, depending on a variation factor (e.g., experimental results for absorption by hemoglobin and the ability to reach a surface area or a deep area of tissue).

The first image and the second image may be an in vivo image. The specific wavelength band included in the in vivo image may be the wavelength band of fluorescence emitted from a fluorescent substance. Specifically, the specific wavelength band may be 490 to 625 nm.

This makes it possible to implement autofluorescence imaging (AFI). Intrinsic fluorescence produced by a fluorescent substance (e.g., collagen) can be observed by applying excitation light (390 to 470 nm). In this case, a lesion area can be highlighted in a color differing from that of a normal mucous membrane, so that the lesion area can be reliably detected, for example. A wavelength band of 490 to 625 nm is the wavelength band of fluorescence produced by a fluorescent substance (e.g., collagen) when excitation light is applied. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for the wavelength band of fluorescence emitted from a fluorescent substance). A pseudo-color image may be generated by simultaneously applying light within a wavelength band (540 to 560 nm) that is absorbed by hemoglobin.

The first image and the second image may be an in vivo image. The specific wavelength band included in the in vivo image may be the wavelength band of infrared light. Specifically, the specific wavelength band may be 790 to 820 nm or 905 to 970 nm.

This makes it possible to implement infrared imaging (IRI). Information about a blood vessel or a blood flow in a deep area of a mucous membrane that is difficult to observe visually, can be highlighted by intravenously injecting indocyanine green (ICG) (infrared marker) that easily absorbs infrared light, and applying infrared light within the above wavelength band, so that the depth of gastric cancer invasion or the therapeutic strategy can be determined, for example. An infrared marker exhibits maximum absorption in a wavelength band of 790 to 820 nm, and exhibits minimum absorption in a wavelength band of 905 to 970 nm. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by the infrared marker).

The first embodiment may also be applied to an electronic apparatus that includes an image processing device (image processing section).

For example, the image processing device according to the first embodiment may be provided in various types of electronic apparatus (i.e., an apparatus that operates using a power source (e.g., voltage or current)), such as an endoscope, a digital camera, a digital video camera, and a personal computer.

The first embodiment may also be applied to a program that causes a computer to function as a first image acquisition section, a second image acquisition section, the type determination section 343, and the highlight section 350. The first image acquisition section acquires a first image that is an image that includes an object image including information within the wavelength band of white light, and the second image acquisition section acquires a second image that is an image that includes an object image including information within the specific wavelength band. The type determination section 343 determines the type of an object image based on the feature quantity of each pixel included in the second image. The highlight section 350 performs the highlight process on the first image based on the type of the object image determined by the area type determination section 340.

This makes it possible to store image data in advance (e.g., capsule endoscope), and process the stored image data by software using a computer system (e.g., PC).

The first embodiment may also be applied to a program that causes a computer to function as a first image acquisition section, a second image acquisition section, and the highlight section 350. The first image acquisition section acquires a first image that is an image that includes an object image including information within the wavelength band of the white light, and the second image acquisition section acquires a second image that is an image that includes an object image including information within the specific wavelength band. The highlight section 350 performs the highlight process on the first image based on the type of the second image.

This makes it possible to store image data in advance (e.g., capsule endoscope), and process the stored image data by software using a computer system (e.g., PC). This makes it possible to perform the highlight process based on the type of the second image instead of the type of the object image.

The first embodiment may also be applied to an image processing method including acquiring a first image that is an image that includes an object image including information within the wavelength band of the white light, acquiring a second image that is an image that includes an object image including information within the specific wavelength band, determining the type of an object image based on the feature quantity of each pixel included in the second image, and performing the highlight process on the first image based on the type of the object image.

This makes it possible to implement an image processing method that can implement the process according to the first embodiment.

The first embodiment may also be applied to an image processing method including acquiring a first image that is an image that includes an object image including information within the wavelength band of the white light, acquiring a second image that is an image that includes an object image including information within the specific wavelength band, and performing the highlight process on the first image based on the type of the second image.

This makes it possible to implement an image processing method that can implement the process according to the first embodiment. In particular, it is possible to perform the highlight process based on the type of the second image instead of the type of the object image.

The first embodiment may also be also be applied to a computer program product that stores a program code that implements each section (e.g., first image acquisition section, second image acquisition section, area type determination section, and highlight section) according to the first embodiment.

The program code implements a first image acquisition section that acquires a first image that is an image that includes an object image including information within the wavelength band of the white light, a second image acquisition section that acquires a second image that is an image that includes an object image including information within the specific wavelength band, an area type determination section that determines the type of an object image in the second image based on the feature quantity of each pixel included in the second image, and a highlight section that performs the highlight process on a signal included in the first image based on the type of the object image determined by the area type determination section.

The term "computer program product" refers to an information storage medium, a device, an instrument, a system, or the like that stores a program code, such as an information storage medium (e.g., optical disk medium (e.g., DVD), hard disk medium, and memory medium) that stores a program code, a computer that stores a program code, or an Internet system (e.g., a system including a server and a client terminal), for example. In this case, each element and each process according to the first embodiment are implemented by corresponding modules, and a program code that includes these modules is recorded in the computer program product.

2. Second Embodiment

Figure 15:
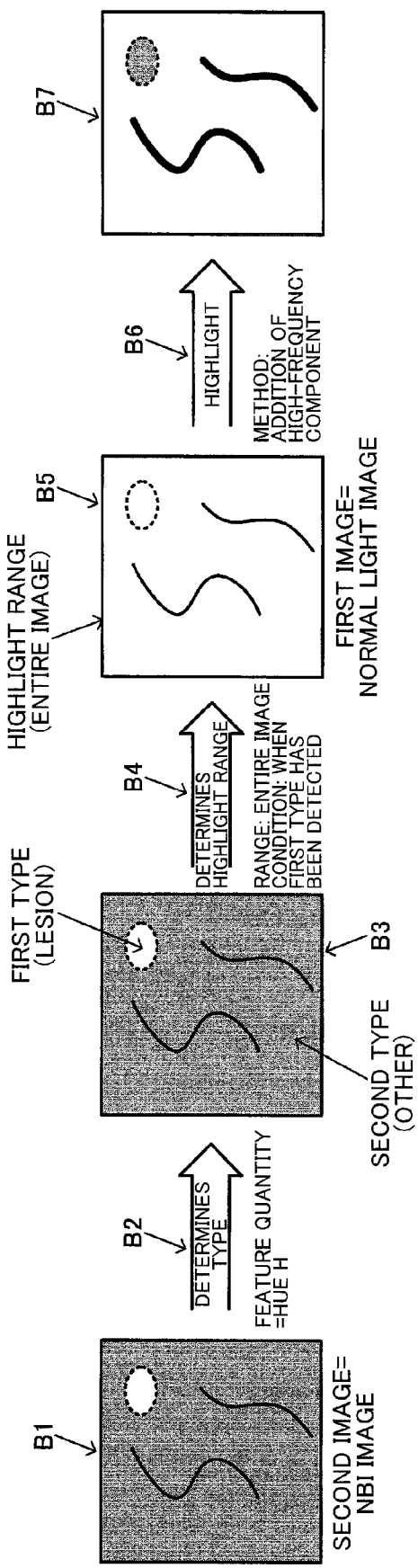
FIG. 15 is another view illustrating a type determination process and a highlight process.

An outline of a second embodiment is described below with reference to FIG. 15. An object of the second embodiment is to determine the type of an object image in the second image, and perform the highlight process on the first image corresponding to the type of object image in the same manner as in the first embodiment.

In the second embodiment, the second image is an NBI image (see B1). The type of an object image in the second image is determined (B2). In the example illustrated in FIG. 15, the hue H is used as the feature quantity for determining the type of the object image. An object image having a hue H of 5 to 35 and having a size equal to or larger than a given threshold value is determined to be a first type of object image, and an object image other than the first type of object image is determined to be a second type of object image. The first type of object image corresponds to a lesion area, and the second type of object image corresponds to an area (normal area) other than a lesion area.

A highlight range is determined after determining the type of the object image. In the second embodiment, the highlight process is performed on the entire first image on condition that the first type of object image (lesion area) has been detected (B4). Therefore, a range indicated by B5 is highlighted in the first image. The highlight process is not performed when the first type of object image has not been detected.

The highlight process is performed on the highlight range using a given method. In the second embodiment, the highlight process is implemented by adding a high-frequency component. More specifically, the highlight process is implemented using a wavelet transform or the like (B6). The highlight process corresponding to the type of object image can be performed by changing the highlight process depending on whether or not the first type of object image has been detected. A normal light image in which the blood vessel and the lesion area are highlighted (see B7) can thus be acquired. Note that the addition of a high-frequency component corresponds to highlighting the blood vessel. Since blood vessels are densely present in a lesion area, the lesion area is also highlighted.

An endoscope system according to the second embodiment is described below. FIG. 2 illustrates the configuration of the endoscope system according to the second embodiment. The process other than the process of the area type determination section 340 and the process of the highlight section 350 is performed in the same manner as in the first embodiment.

A specific configuration of the area type determination section 340 according to the second embodiment is described below. The area type determination section 340 according to the second embodiment is basically configured in the same manner as the area type determination section 340 illustrated in FIG. 9. An element identical with that of the area type determination section 340 illustrated in FIG. 9 is indicated by an identical name and an identical reference number. The following description focuses on the differences from the area type determination section 340 illustrated in FIG. 9.

Figure 16:
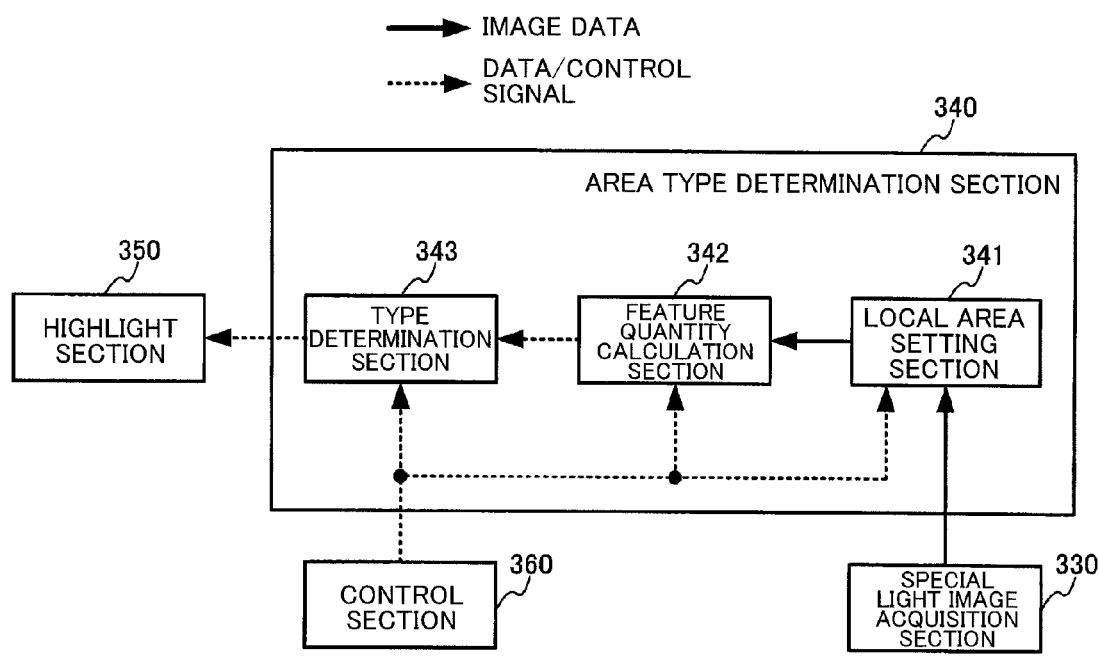
FIG. 16 illustrates another configuration example of an area type determination section.

FIG. 16 is a block diagram illustrating an example of the configuration of the area type determination section 340 according to the second embodiment. The area type determination section 340 includes a local area setting section 341, a feature quantity calculation section 342, and a type determination section 343. The narrow-band light image output from the special light image acquisition section 330 is input to the local area setting section 341. The control section 360 is connected to the local area setting section 341, the feature quantity calculation section 342, and the type determination section 343, and controls the local area setting section 341, the feature quantity calculation section 342, and the type determination section 343. The type determination section 343 is connected to the highlight section 350. The process of the local area setting section 341 and the process of the feature quantity calculation section 342 are the same as those described in connection with the first embodiment.

The type determination section 343 determines whether or not each local area is likely to be a lesion using the hue H of each local area calculated by the feature quantity calculation section 342, and outputs the determination result to the highlight section 350. In the narrow-band light image used in the second embodiment, a lesion area (e.g., epidermoid cancer) is visualized (drawn) as a brown area. Therefore, whether or not each local area is likely to be a lesion can be determined using the hue H as the feature quantity. More specifically, an area having a hue H of 5 to 35 may be determined to be an area that is likely to be a lesion.

The type determination section 343 outputs flag information to the highlight section 350, the flag information indicating whether or not an area that is likely to be a lesion is present in the narrow-band light image. For example, the flag information may be set to "1" when the number of local areas that are likely to be a lesion is equal to or larger than a given number, and may be set to "0" when an area that is likely to be a lesion is not present.

Note that the local area set by the local area setting section 341 is not limited to a 5×5 pixel rectangular area (refer to the first embodiment). In the second embodiment, a relatively large area (e.g., 16×16 pixel area) may be set as the local area. This is because blood vessels are densely present in a lesion area as compared with a normal area. Specifically, a small area (e.g., 5×5 pixel area) may have a hue H of 5 to 35 even if blood vessels are not densely present (e.g., even if one blood vessel is present). Therefore, it is necessary to determine whether or not an area in the image is a lesion based on whether or not areas that are likely to be a lesion are densely present. Specifically, it is necessary to set an appropriate threshold value, and determine whether or not an area that is likely to be a lesion has a size equal to or larger than the threshold value.

On the other hand, when setting a relatively large area (e.g., 16×16 pixel area) as the local area, the local area can include a number of blood vessels. Therefore, only a local area in which blood vessels are densely present has a hue H of 5 to 35. This makes it possible to determine that an area in the image is a lesion when one area in the image is likely to be a lesion.

Figure 17:
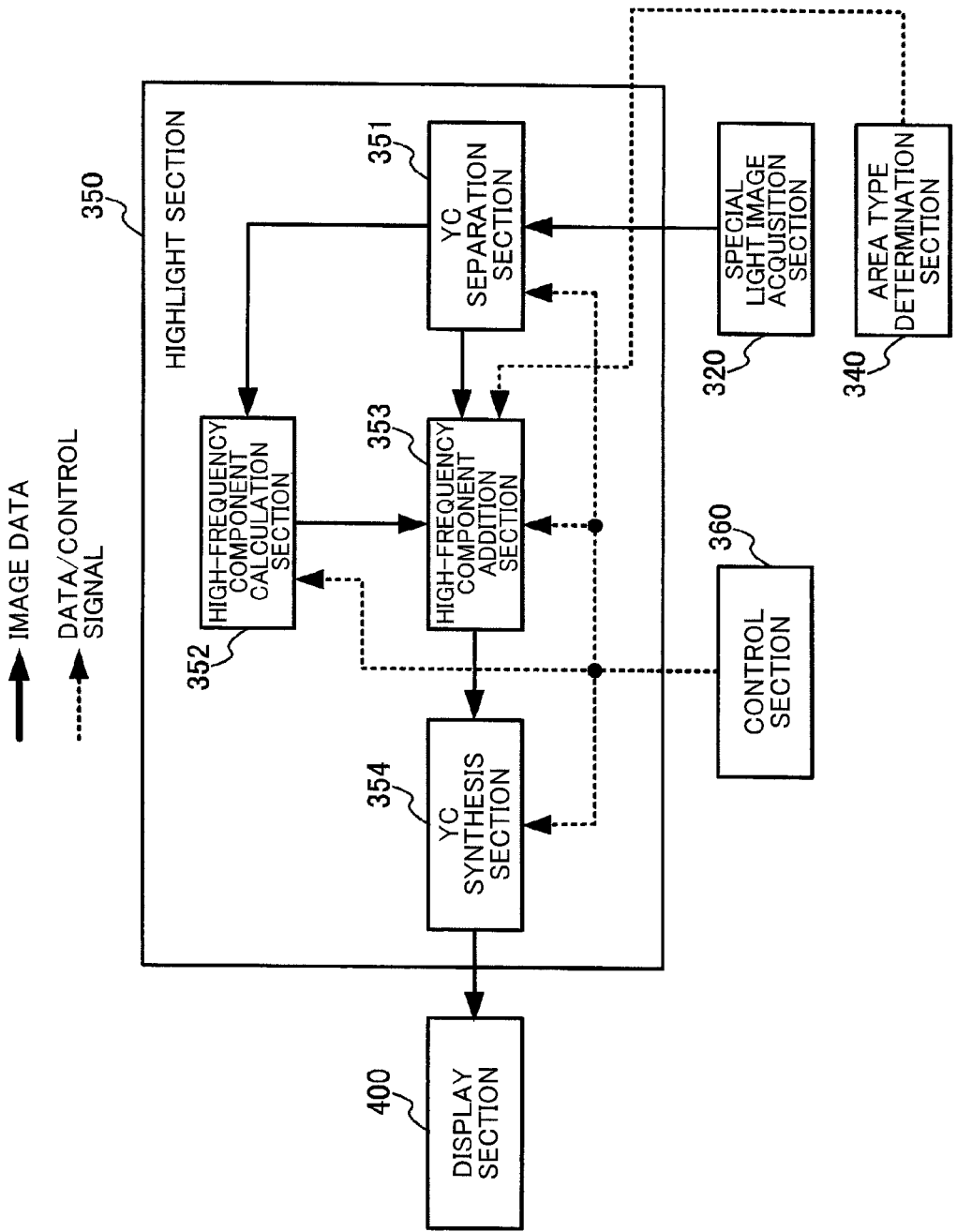
FIG. 17 illustrates a configuration example of a highlight section.

The configuration of the highlight section 350 is described below. FIG. 17 is a block diagram illustrating an example of the configuration of the highlight section 350 according to the second embodiment. The highlight section 350 includes a YC separation section 351, a high-frequency component calculation section 352, a high-frequency component addition section 353, and a YC synthesis section 354. The normal light image output from the normal light image acquisition section 320 is input to the YC separation section 351. The flag information output from the area type determination section 340 is input to the high-frequency component addition section 353. The control section 360 is connected to the YC separation section 351, the high-frequency component calculation section 352, the high-frequency component addition section 353, and the YC synthesis section 354, and controls the YC separation section 351, the high-frequency component calculation section 352, the high-frequency component addition section 353, and the YC synthesis section 354. The YC synthesis section 354 is connected to the display section 400.

The YC separation section 351 converts the normal light image input from the normal light image acquisition section 320 into luminance/color difference signals using a known YC separation process. The normal light image may be converted into the luminance/color difference signals using the following expression (11), for example. Note that Y in the expression (11) is the luminance signal of the normal light image, and Cb and Cr in the expression (11) are the color difference signals of the normal light image.

The YC separation section 351 outputs the normal light image converted into the luminance/color difference signals to the high-frequency component calculation section 352 and the high-frequency component addition section 353. Note that only the luminance signals are output to the high-frequency component calculation section 352, and the luminance signals and the color difference signals are output to the high-frequency component addition section 353.

$$\begin{bmatrix} Y \\ Cb \\ Cr \end{bmatrix} = \begin{bmatrix} 0.2126 & 0.7152 & 0.0722 \\ -0.1146 & 0.3854 & 0.5000 \\ 0.5000 & -0.4542 & -0.0458 \end{bmatrix} \begin{bmatrix} R \\ G \\ B \end{bmatrix} \quad (11)$$

The high-frequency component calculation section 352 subjects the luminance signals of the normal light image to multiple resolution transformation using a known wavelet transform, extracts a high-frequency component from the luminance signals subjected to multiple resolution transformation, and outputs the high-frequency component to the high-frequency component addition section 353. The process of the high-frequency component calculation section 352 is described later.

The high-frequency component addition section 353 adds the high-frequency component output from the high-frequency component calculation section 352 to the luminance signals of the normal light image output from the YC separation section 351 corresponding to the flag information output from the area type determination section 340, and outputs the resulting normal light image to the YC synthesis section 354.

The YC synthesis section 354 performs a known YC synthesis process on the normal light image output from the high-frequency component addition section 353 to obtain an RGB image, and outputs the RGB image to the display section 400. The YC synthesis process may be implemented using the following expression (12), for example.

$$\begin{bmatrix} R \\ G \\ B \end{bmatrix} = \begin{bmatrix} 1.0000 & 0.0000 & 1.5748 \\ 1.0000 & -0.1873 & -0.4681 \\ 1.0000 & 1.8556 & -0.0458 \end{bmatrix} \begin{bmatrix} Y \\ Cb \\ Cr \end{bmatrix} \quad (12)$$

Figure 18:
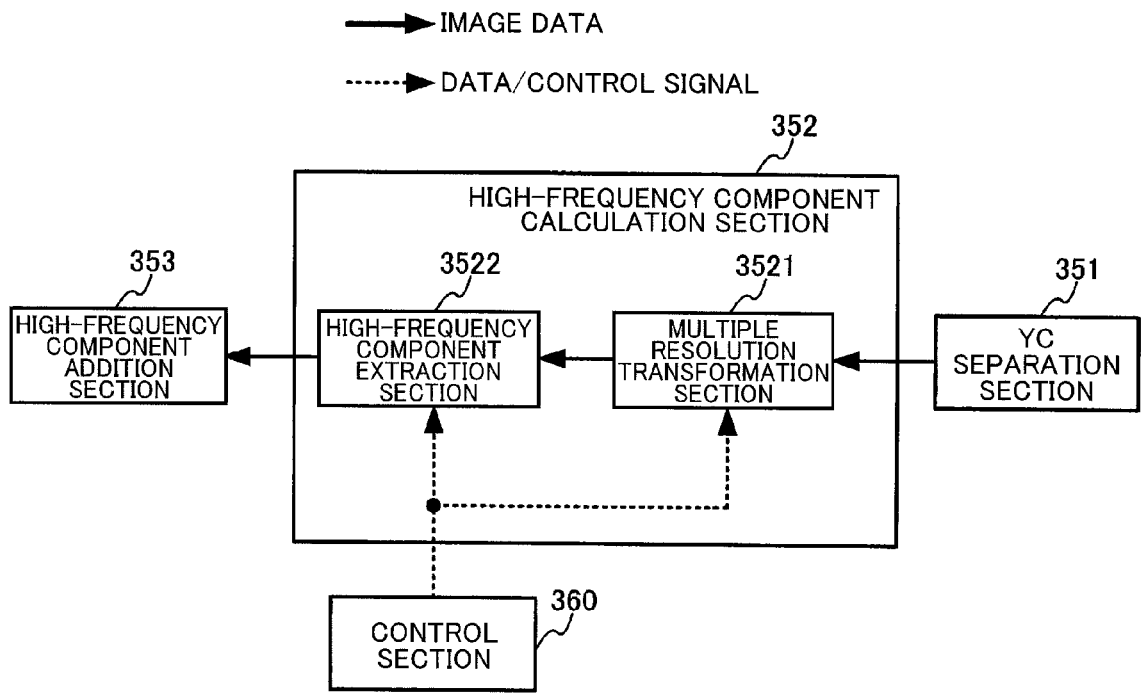
FIG. 18 illustrates a configuration example of a high-frequency component calculation section.

The details of the process of the high-frequency component calculation section 352 are described below. FIG. 18 is a view illustrating an example of the configuration of the high-frequency component calculation section 352 according to the second embodiment. The high-frequency component calculation section 352 includes a multiple resolution transformation section 3521 and a high-frequency component extraction section 3522. The control section 360 is connected to the multiple resolution transformation section 3521 and the high-frequency component extraction section 3522, and controls the multiple resolution transformation section 3521 and the high-frequency component extraction section 3522. The high-frequency component extraction section 3522 is connected to the high-frequency component addition section 353. The normal light image output from the YC separation section 351 is input to the multiple resolution transformation section 3521.

The multiple resolution transformation section 3521 subjects the luminance signals of the normal light image output from the YC separation section 351 to multiple resolution transformation using a known wavelet transform. The image obtained by multiple resolution transformation is referred to as a multiple resolution-transformed image. The wavelet transform is shown by the following expression (13) using the luminance signal Y(x, y) of the normal light image at the coordinates (x, y) and the signal value S(i, j) of the multiple resolution-transformed image at the coordinates (i, j). Note that ImW is the width of the normal light image, and ImH is the height of the normal light image.

$$S(i, j) = \begin{cases} \left( \begin{matrix} Y(2i, 2j) + Y(2i+1, 2j) + \\ Y(2i, 2j+1) + Y(2i+1, 2j+1) \end{matrix} \right) \Big/ 4 & (0 \le i < Im_w/2,\ 0 \le j < Im_H/2) \\[6pt] \left( \begin{matrix} Y(2i - Im_w, 2j) - Y(2i+1 - Im_w, 2j) + \\ Y(2i - Im_w, 2j+1) - Y(2i+1 - Im_w, 2j+1) \end{matrix} \right) \Big/ 4 & (Im_w/2 \le i < Im_w,\ 0 \le j < Im_H/2) \\[6pt] \left( \begin{matrix} Y(2i, 2j - Im_H) + Y(2i+1, 2j - Im_H) - \\ Y(2i, 2j+1 - Im_H) - Y(2i+1, 2j+1 - Im_H) \end{matrix} \right) \Big/ 4 & (0 \le i < Im_w/2,\ Im_H/2 \le j < Im_H) \\[6pt] \left( \begin{matrix} Y(2i - Im_w, 2j - Im_H) - Y(2i+1 - Im_w, 2j - Im_H) - \\ Y(2i - Im_w, 2j+1 - Im_H) + Y(2i+1 - Im_w, 2j+1 - Im_H) \end{matrix} \right) \Big/ 4 & (Im_w/2 \le i < Im_w,\ Im_H/2 \le j < Im_H) \end{cases} \quad (13)$$

Figure 19:
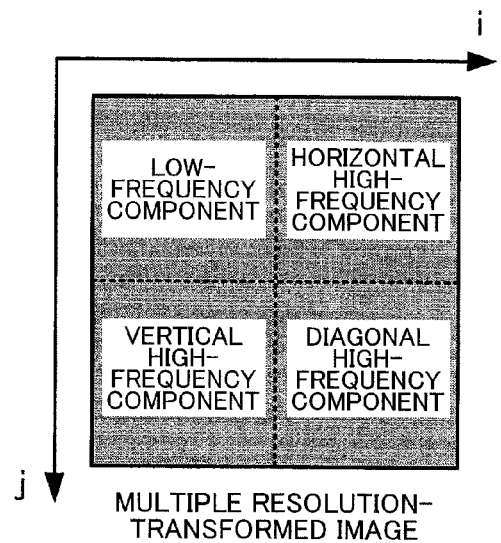
FIG. 19 is a view illustrating a multiple resolution-transformed image obtained by a wavelet transform.

FIG. 19 is a view illustrating the relationship between the multiple resolution-transformed image and the frequency component of the luminance signal of the normal light image. As illustrated in FIG. 19, the upper left area of the multiple resolution-transformed image corresponds to a low-frequency component of the luminance signal of the normal light image, the upper right area of the multiple resolution-transformed image corresponds to a horizontal high-frequency component of the luminance signal of the normal light image, the lower left area of the multiple resolution-transformed image corresponds to a vertical high-frequency component of the luminance signal of the normal light image, and the lower right area of the multiple resolution-transformed image corresponds to a diagonal high-frequency component of the luminance signal of the normal light image.

Figure 20:
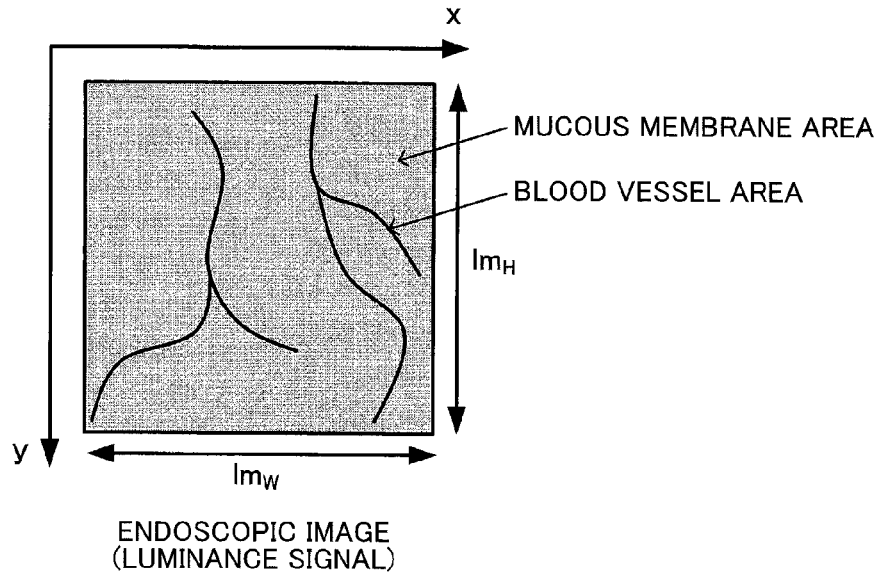
FIG. 20 is a view illustrating an endoscopic image.
Figure 21:
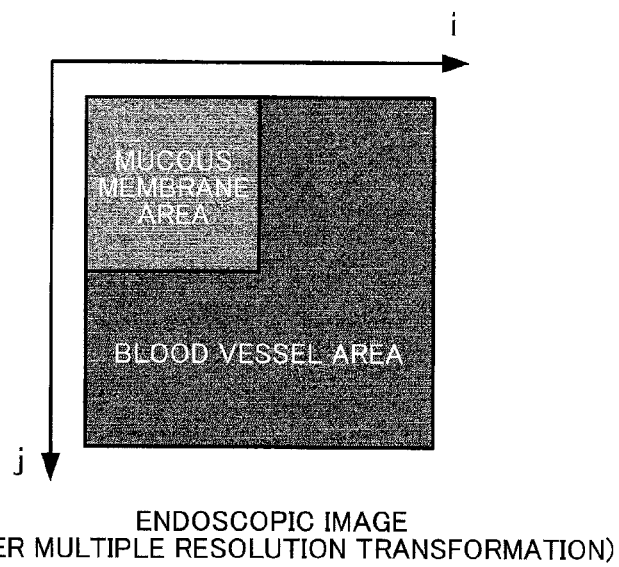
FIG. 21 is a view illustrating the relationship between a blood vessel and a mucous membrane in a multiple resolution-transformed image.

FIG. 20 illustrates an example of the luminance signals of an endoscopic image, and FIG. 21 is a view illustrating the results obtained when subjecting the luminance signals of the endoscopic image illustrated in FIG. 20 to the wavelet transform. An endoscopic image is characterized in that a blood vessel area includes a low-frequency component and a high-frequency component, while a mucous membrane area includes a large amount of a low-frequency component, but includes a small amount of a high-frequency component. Therefore, the multiple resolution-transformed image illustrated in FIG. 21 has a configuration in which a blood vessel area and a mucous membrane area are distributed in the low-frequency component area illustrated in FIG. 19, and a blood vessel area is mainly distributed in the horizontal high-frequency component area, the vertical high-frequency component area, and the diagonal high-frequency component area illustrated in FIG. 19.

The high-frequency component extraction section 3522 generates a high-frequency component image obtained by extracting only the high-frequency component from the multiple resolution-transformed image output from the multiple resolution transformation section 3521 using a method described below, and outputs the high-frequency component image to the high-frequency component addition section 353. Note that the high-frequency component image has the same size as that of the normal light image, and is fowled by an arbitrary combination of the horizontal high-frequency component, the vertical high-frequency component, and the diagonal high-frequency component of the multiple resolution-transformed image. The signal value H(x, y) of the high-frequency component image at the coordinates (x, y) is given by the following expression (14), for example. Note that Floor(a) in the expression (14) indicates a process that rounds the real number a off to the closest whole number, and abs_max(a, b, c) in the expression (14) indicates a process that selects a real number having the maximum absolute value from the real numbers a, b, and c.

$$H(x, y) = \text{abs\_max} \begin{Bmatrix} S(\text{floor}(x/2) + Im_W/2, \text{floor}(y/2)), \\ S(\text{floor}(x/2), \text{floor}(y/2) + Im_H/2), \\ S(\text{floor}(x/2) + Im_W/2, \text{floor}(y/2) + Im_H/2) \end{Bmatrix} \quad (14)$$

The high-frequency component addition section 353 performs the highlight process on the normal light image output from the YC separation section 351 corresponding to the flag information output from the area type determination section 340, and outputs the resulting normal light image to the YC synthesis section 354.

More specifically, the high-frequency component addition section 353 adds the high-frequency component image output from the high-frequency component calculation section 352 to the luminance signals of the normal light image when the flag information output from the area type determination section 340 is set to "1" (i.e., when an area that is likely to be a lesion is present), and outputs the resulting normal light image to the YC synthesis section 354. The high-frequency component addition section 353 directly outputs the normal light image output from the YC separation section 351 to the YC synthesis section 354 when the flag information output from the area type determination section 340 is set to "0" (i.e., when an area that is likely to be a lesion is not present).

Since a blood vessel area that is important for diagnosing a lesion is highlighted by performing the above process when an area that is likely to be a lesion area is displayed in the normal light image, it is possible to prevent a situation in which a lesion area is missed while reducing the burden on the doctor during a diagnosis that utilizes the normal light image and the narrow-band light image.

Although an example in which each section of the image processing section 300 is implemented by hardware has been described above, a CPU may perform the process of each section on an image acquired in advance in the same manner as in the first embodiment. Specifically, the process of each section may be implemented by software by causing the CPU to execute a program. Alternatively, the process of each section may partially be implemented by software.

A process performed on the normal light image and the narrow-band light image acquired in advance when implementing the process of the area type determination section 340 and the process of the highlight section 350 illustrated in FIG. 2 by software is described below. In this case, the process is performed in the same manner as in the first embodiment except for the area type determination step (Step 3) and the highlight step (Step 4) (see FIG. 13).

Figure 22:
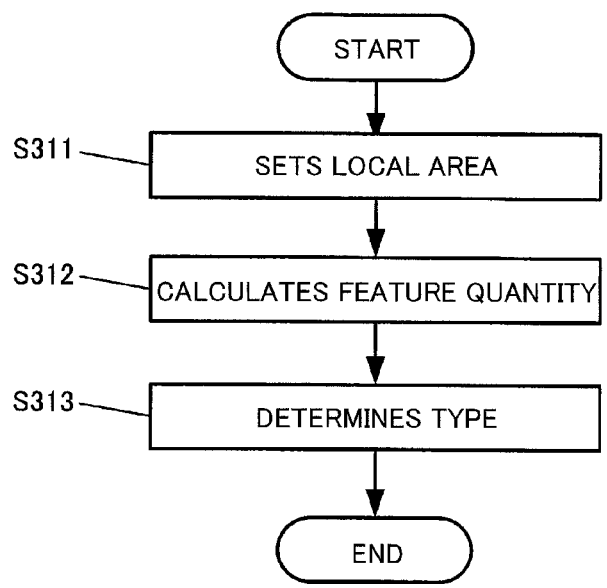
FIG. 22 is another flowchart, illustrating an area type determination process.

A specific process of the area type determination step (Step 3) (see FIG. 13) according to the second embodiment is described below using a flowchart illustrated in FIG. 22. In the local area setting step, a plurality of local areas are set within the narrow-band light image in the same manner as in the first embodiment (Step 311). In the feature quantity calculation step, the feature quantity of each local area is calculated in the same manner as in the first embodiment (Step 312). In the second embodiment, the hue H is used as an example of the feature quantity. In the type determination step, the type determination process is performed on each local area, and the flag information that indicates whether or not an area that is likely to be a lesion is present is output (Step 313). For example, the type determination process determines a local area having a hue H of 5 to 35 to be an area that is likely to be a lesion. The flag information "1" is output when the number of local areas that are likely to be a lesion is equal to or larger than a given threshold value, and the flag information "0" is output when the number of local areas that are likely to be a lesion is equal to or less than the threshold value.

Figure 23:
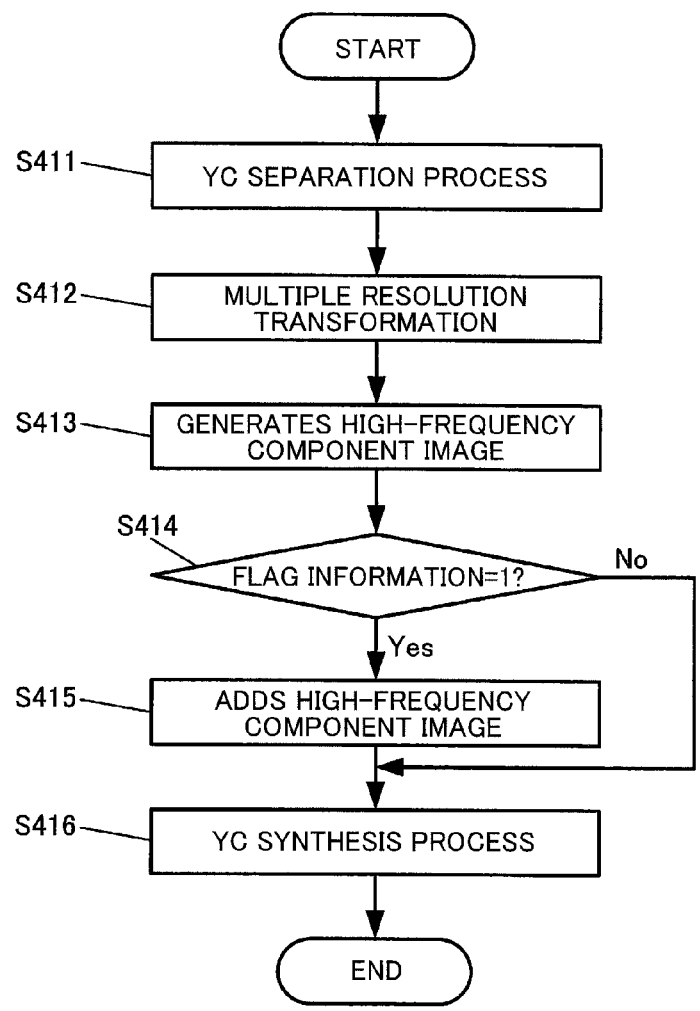
FIG. 23 is a flowchart illustrating a highlight process.

A specific process of the highlight step (Step 4) is described below using a flowchart illustrated in FIG. 23. In the YC separation step, the normal light image is converted into the luminance/color difference signals using the YC separation process shown by the expression (11) (Step 411). In the multiple resolution transformation step, the multiple resolution transformation process is performed on the luminance signals subjected to the YC separation process using the wavelet transform shown by the expression (13) (Step 412). In the high-frequency component image generation step, the high-frequency component image is generated from the image obtained by the multiple resolution transformation using the expression (14) (Step 413). In Step 414, a process of Step 415 is performed when the flag information output in Step 313 is "1", and a process of Step 416 is performed when the flag information output in Step 313 is "0". In Step 415, the high-frequency component image generated in Step 413 is added to the luminance signals of the normal light image. In Step 416, the normal light image is converted into RGB signals by performing the YC synthesis process shown by the expression (12), and the RGB signals (image) are output.

Since a blood vessel area that is important for diagnosing a lesion is highlighted by performing the above process when an area that is likely to be a lesion area is displayed in the normal light image, it is possible to prevent a situation in which a lesion area is missed while reducing the burden on the doctor during a diagnosis that utilizes the normal light image and the narrow-band light image.

According to the second embodiment, a plurality of types may be provided as the type of the second image. In this case, the method of performing the highlight process is determined corresponding to the type of the object image and the type of the second image. More specifically, when the second image is an NBI image, and the object image is a lesion, the highlight process is performed on the entire image (see FIG. 15).

This makes it possible to determine the method of performing the highlight process taking account of the type of the object image and the type of the second image. For example, the entire image may be highlighted when the object image is a lesion and the second image is an NBI image (see FIG. 15).

The highlight section 350 may enhance a specific frequency component of the spatial frequency of the first image over the entirety of the first image.

This makes it possible to enhance the specific frequency component from the multiple resolution-transformed image obtained by a wavelet transform or the like. For example, it is possible to highlight a blood vessel area that includes a large amount of high-frequency component by enhancing (adding) a high-frequency component.

3. Third Embodiment

Figure 24:
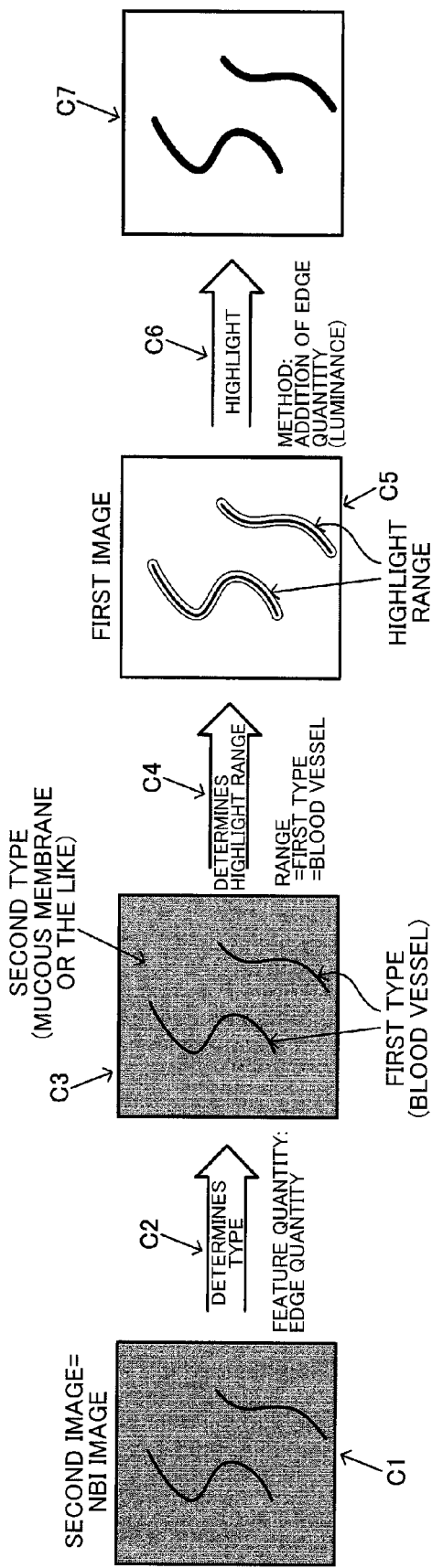
FIG. 24 is another view illustrating a type determination process and a highlight process.

An outline of a third embodiment of the invention is described below with reference to FIG. 24. An object of the third embodiment is to determine the type of an object image in the second image, and perform the highlight process on the first image corresponding to the type of object image in the same manner as in the first embodiment.

In the third embodiment, the second image is an NBI image (see C1). The type of an object image in the second image is determined (C2). In the example illustrated in FIG. 24, the edge quantity E is used as the feature quantity for determining the type of the object image. An object image having an edge quantity E equal to or larger than a given threshold value is determined to be a first type of object image, and an object image other than the first type of object image is determined to be a second type of object image. The first type of object image corresponds to a blood vessel, and the second type of object image corresponds to an area (e.g., mucous membrane) other than a blood vessel.

A highlight range is determined after determining the type of the object image. In the third embodiment, the highlight process is performed on an area of the first image that corresponds to the first type of object image (blood vessel) (C4). Therefore, a range indicated by C5 is highlighted in the first image.

The highlight process is performed on the highlight range using a given method. In the third embodiment, the highlight is implemented by adding the edge quantity E. More specifically, the edge quantity E is added to the luminance component of the first image (C6). The highlight process corresponding to the type of the object image can be performed by performing the highlight process on the first type of object image without performing the highlight process on the second type of object image. A normal light image in which the blood vessel is highlighted (see C7) can thus be acquired.

An endoscope system according to the third embodiment is described below. FIG. 2 illustrates the configuration of the endoscope system according to the third embodiment. The process other than the process of the area type determination section 340 and the process of the highlight section 350 is performed in the same manner as in the first embodiment.

A specific configuration of the area type determination section 340 according to the third embodiment is described below. The area type determination section 340 according to the third embodiment is basically configured in the same manner as the area type determination section 340 illustrated in FIG. 9. An element identical with that of the area type determination section 340 illustrated in FIG. 9 is indicated by an identical name and an identical reference number. The following description focuses on the differences from the area type determination section 340 illustrated in FIG. 9.

Figure 25:
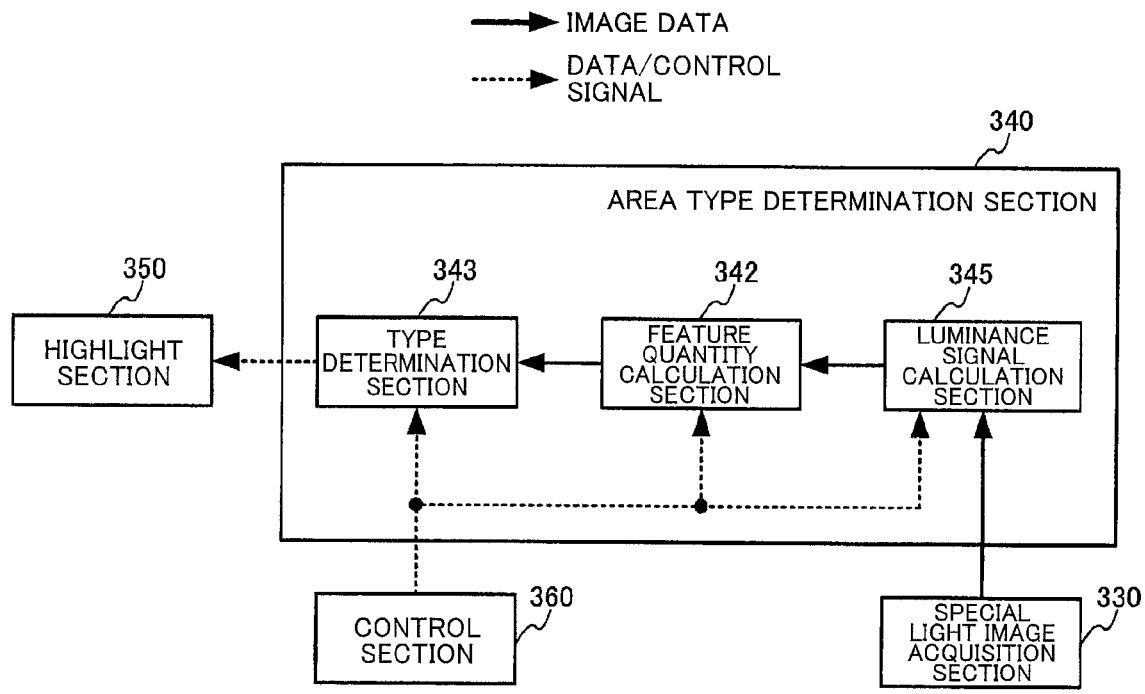
FIG. 25 illustrates another configuration example of an area type determination section.

FIG. 25 is a block diagram illustrating an example of the configuration of the area type determination section 340 according to the third embodiment. The area type determination section 340 includes a luminance signal calculation section 345, a feature quantity calculation section 342, and a type determination section 343. The image signal output from the special light image acquisition section 330 is input to the luminance signal calculation section 345. The luminance signal calculation section 345 is connected to the feature quantity calculation section 342, and the feature quantity calculation section 342 is connected to the type determination section 343. The type determination section 343 is connected to the highlight section 350. The control section 360 is connected to the luminance signal calculation section 345, the feature quantity calculation section 342, and the type determination section 343, and controls the luminance signal calculation section 345, the feature quantity calculation section 342, and the type determination section 343.

The luminance signal calculation section 345 calculates the luminance signal Y of each pixel from the narrow-band light image input from the special light image acquisition section 330, and outputs the luminance signal Y to the feature quantity calculation section 342. The luminance signal may be calculated using the expression (11), for example.

The feature quantity calculation section 342 calculates the edge quantity E of each pixel of the normal light image using the luminance signal output from the luminance signal calculation section 345, and outputs the edge quantity E to the type determination section 343. The edge quantity E(x, y) of the narrow-band light image at the coordinates (x, y) may be calculated using the following expression (15), for example.

$$E(x, y) = \left| \sum_{i=-1}^{1} \sum_{j=-1}^{1} C_{i,j} \times Y(x+i, y+j) \right| \quad \begin{array}{l} C_{i,j} = 8 \, (i = j = 0) \\ -1 \, \text{else} \end{array} \quad (15)$$

The type determination section 343 determines whether or not each pixel of the narrow-band light image is a blood vessel based on the edge quantity output from the feature quantity calculation section 342. Since an endoscopic image is characterized in that a blood vessel area has a large edge quantity and a mucous membrane area has a small edge quantity, a blood vessel area can be determined (discriminated) using the edge quantity. For example, the pixel at the coordinates (x, y) may be determined to be a blood vessel when the edge quantity E(x, y) is larger than a threshold value E_ave (see the following expression (16)). The threshold value E_ave may be the average value calculated from the edge quantity E(x, y) of each pixel of the narrow-band light image, for example. The type determination section 343 outputs information about the position and the edge quantity E(x, y) of each pixel that has been determined to be a blood vessel to the highlight section 350.

$$E(x, y) > E\_ave \qquad (16)$$

A specific configuration of the highlight section 350 is described below. The highlight section 350 is basically configured in the same manner as the highlight section 350 illustrated in FIG. 17. An element identical with that of the highlight section 350 illustrated in FIG. 17 is indicated by an identical name and an identical reference number. The following description focuses on the differences from the highlight section 350 illustrated in FIG. 17.

Figure 26:
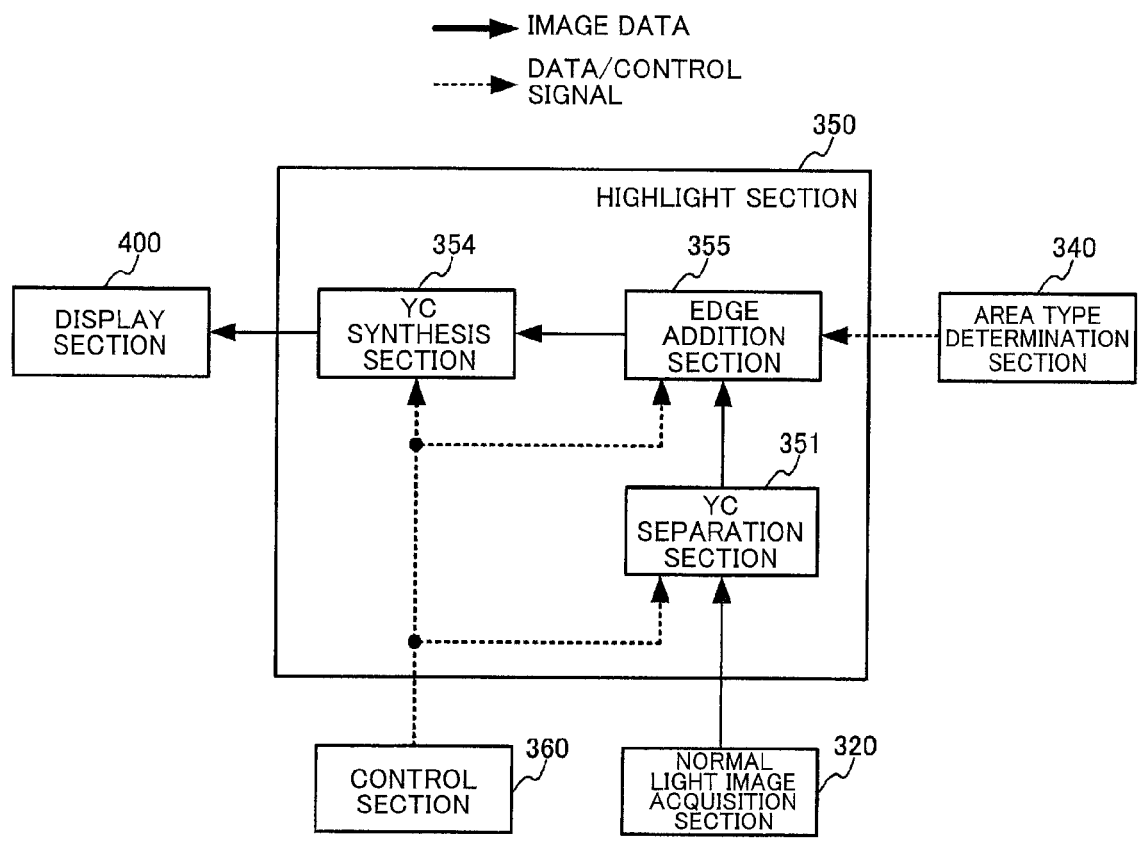
FIG. 26 illustrates another configuration example of a highlight section.

FIG. 26 is a block diagram illustrating an example of the configuration of the highlight section 350 according to the third embodiment. The highlight section 350 includes a YC separation section 351, an edge addition section 355, and a YC synthesis section 354. The YC separation section 351 is connected to the edge addition section 355, and the edge addition section 355 is connected to the YC synthesis section 354. The edge addition section 355 is connected to the area type determination section 340. The edge quantity E(x, y) is output to the edge addition section 355. The control section 360 is connected to the YC separation section 351, the edge addition section 355, and the YC synthesis section 354, and controls the YC separation section 351, the edge addition section 355, and the YC synthesis section 354. Note that the process of the YC separation section 351 and the process of the YC synthesis section 354 are the same as those described above in connection with the second embodiment.

The edge addition section 355 performs the highlight process on the normal light image using the position and the edge quantity E(x, y) of each pixel output from the area type determination section 340. More specifically, the edge addition section 355 adds the edge quantity E(x, y) to the luminance signal Y(x, y) of each pixel of the normal light image corresponding to the position output from the area type determination section 340. The normal light image obtained by the edge addition process is output to the YC synthesis section 354.

Although an example in which the luminance conversion process is performed on the normal light image based on the edge quantity E(x, y) has been described above, the invention is not limited thereto. For example, a color conversion process may be performed on the normal light image based on the edge quantity.

Since a blood vessel area is highlighted by performing the above process, the visibility of a blood vessel is improved. This makes it possible to prevent a situation in which a lesion area is missed while reducing the burden on the doctor during diagnosis using the normal light image and the narrow-band light image. An example in which only the edge quantity is used as the feature quantity when determining a blood vessel has been described above. When the object is tissue, an irregular area (e.g., folded area) also has a large edge quantity. Therefore, the hue H (refer to the first embodiment) may be used as the feature quantity in addition to the edge quantity when determining a blood vessel.

Although an example in which each section of the image processing section 300 is implemented by hardware has been described above, a CPU may perform the process of each section on an image acquired in advance in the same manner as in the first embodiment. Specifically, the process of each section may be implemented by software by causing the CPU to execute a program. Alternatively, the process of each section may partially be implemented by software.

A process performed on the normal light image and the narrow-band light image acquired in advance when implementing the process of the area type determination section 340 and the process of the highlight section 350 illustrated in FIG. 2 by software is described below. In this case, the process is performed in the same manner as in the first embodiment except for the area type determination step (Step 3) and the highlight step (Step 4) (see FIG. 13).

Figure 27:
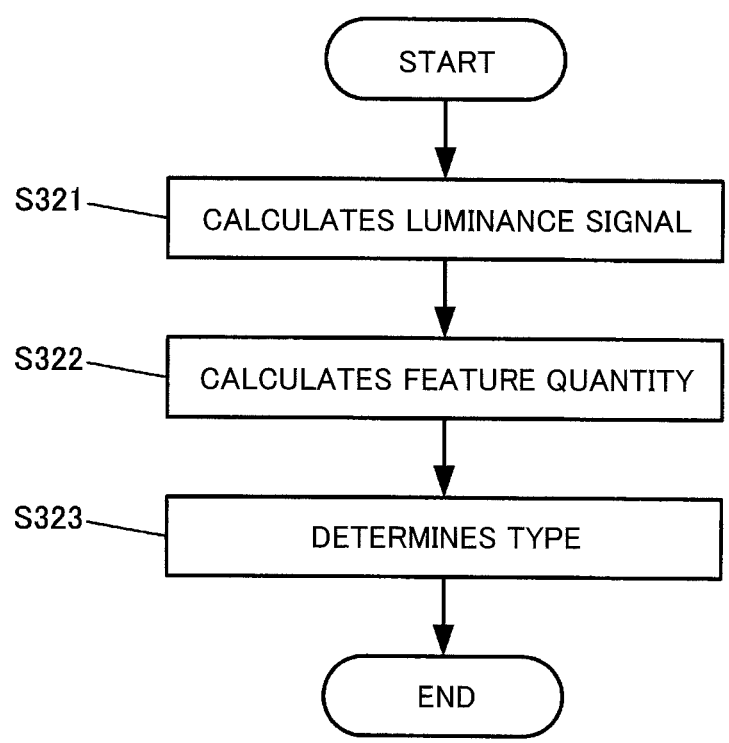
FIG. 27 is another flowchart illustrating an area type determination process.

A specific process of the area type determination step (Step 3) (see FIG. 13) according to the third embodiment is described below using a flowchart illustrated in FIG. 27. In the luminance signal calculation step, the luminance signal of each pixel of the narrow-band light image is calculated using the expression (11) (Step 321). In the feature quantity calculation step, the edge quantity E(x, y) is calculated using the expression (15) (Step 322). In the type determination step, the determination process shown by the expression (16) is performed on each pixel to determine whether or not each pixel is a blood vessel. The position and the edge quantity E(x, y) of each pixel that has been determined to be a blood vessel are output (Step 323).

In the highlight step, the edge quantity E(x, y) is added to the luminance signal Y(x, y) of each pixel of the normal light image corresponding to the position output in the area type determination step (Step 3) (Step 4).

Since a blood vessel area is highlighted by performing the above process, the visibility of a blood vessel is improved. This makes it possible to prevent a situation in which a lesion area is missed while reducing the burden on the doctor during diagnosis using the normal light image and the narrow-band light image.

According to the third embodiment, the highlight section 350 enhances the luminance component or the color component of the corresponding attention area in the first image based on the edge quantity calculated from the second image. The term "corresponding attention area" is the same as defined above.

This makes it possible to implement the type determination process and the highlight process using the edge quantity E as the feature quantity. More specifically, the edge quantity E may be added to the luminance component (Y component of YCrCb) and the color component (R, G, or B component) in an area in which the edge quantity E is larger than the average value. In the third embodiment, the edge quantity E is used as the feature quantity used for the type determination process that determines whether or not each pixel is a blood vessel, and is also used as the parameter used for the highlight process.

4. Fourth Embodiment

An endoscope system according to a fourth embodiment of the invention is described below with reference to FIG. 28. Although the first to third embodiments have been described above taking an example in which the normal light image and the special light image are acquired using two imaging elements, the normal light image and the special light image may be acquired by image processing using only a first imaging element that includes a Bayer color filter array, for example. The endoscope system according to the fourth embodiment includes a light source section 100, an imaging section 200, an image processing section 300, a display section 400, and an external I/F section 500. Note that description of the same elements as those described in connection with the first to third embodiments is appropriately omitted.

The light source section 100 includes a white light source 110 that emits white light, and a condenser lens 120.

The imaging section 200 is formed to be elongated and flexible (i.e., can be curved) so that the imaging section 200 can be inserted into a body cavity or the like. The imaging section 200 can be removed so that a different imaging section can be used depending on the organ to be observed. The imaging section 200 is normally referred to as a scope in the field of endoscopy. Specific examples of the scope include an upper gastrointestinal scope, a lower gastrointestinal scope, and the like.

The imaging section 200 includes a light guide fiber 210 that guides light focused by the light source section 100, an illumination lens 220 that diffuses light that has been guided by the light guide fiber 210, and illuminates an object, an objective lens 230 that focuses light reflected by the object, and a first imaging element 250 detects the reflected light. The first imaging element 250 includes a Bayer color filter array that is used to capture a normal light image, for example. The color filters of the first imaging element 250 have the spectral characteristics illustrated in FIG. 3, for example.

The imaging section 200 includes a memory 280. The memory 280 stores an identification number specific to each scope. The memory 280 is connected to a control section 360. The control section 360 can specify the scope referring to the identification number stored in the memory 280. The control section 360 can also specify the organ to be observed by specifying the scope.

The image processing section 300 includes an A/D conversion section 310, a normal light image acquisition section 320, a special light image acquisition section 330, an area type determination section 340, a highlight section 350, and the control section 360.

The control section 360 is connected to the area type determination section 340 and the highlight section 350, and controls the area type determination section 340 and the highlight section 350.

The external I/F section 500 is an interface that allows the user to perform an input operation on the image processing device, for example.

The A/D conversion section 310 converts an analog image signal output from the first imaging element into a digital image signal, and outputs the digital image signal.

The normal light image acquisition section 320 acquires a normal light image from the digital image signal output from the A/D conversion section 310. The special light image acquisition section 330 acquires a special light image from the digital image signal output from the A/D conversion section 310.

The special light image acquired by the special light image acquisition section 330 is output to the area type determination section 340. The normal light image acquired by the normal light image acquisition section 320 is output to the highlight section 350.

The details of the normal light image acquisition section 320 are described below with reference to FIG. 6. The normal light image acquisition section 320 includes a normal light image generation section 321 and a normal light image storage section 322.

Figure 29:
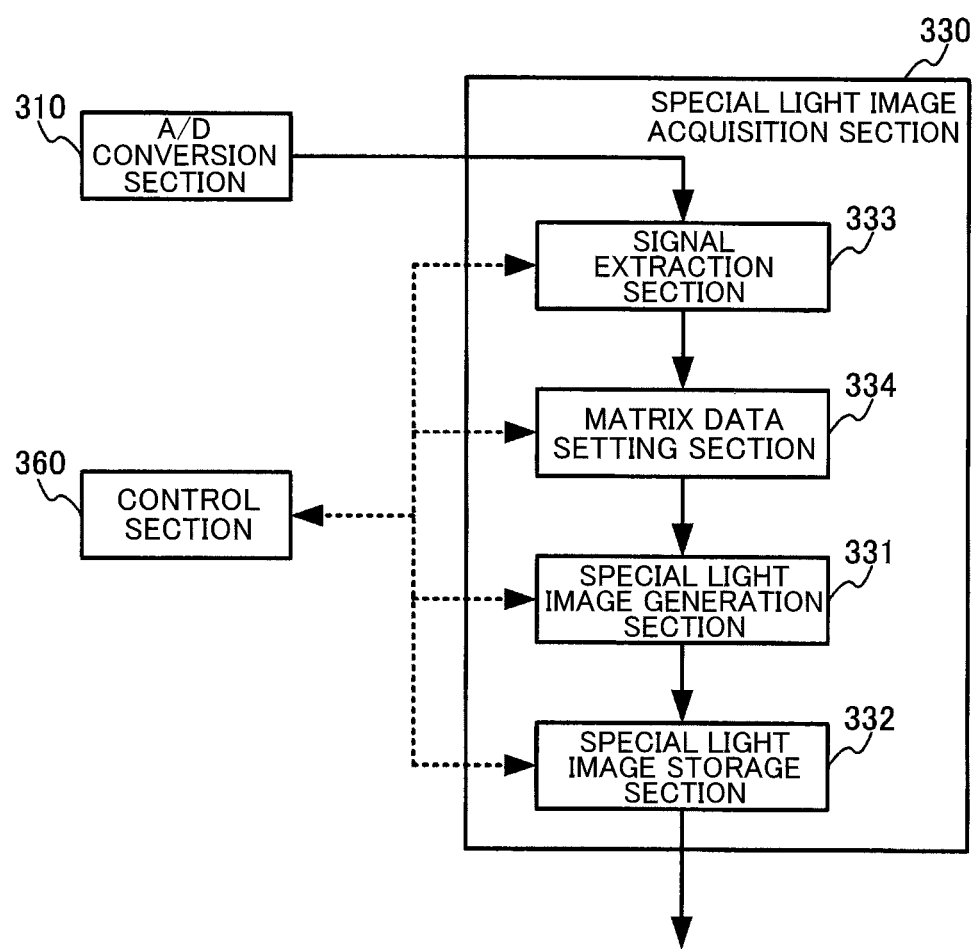
FIG. 29 illustrates another configuration example of a special light image acquisition section.

The details of the special light image acquisition section 330 are described below with reference to FIG. 29. The special light image acquisition section 330 includes a special light image generation section 331, a special light image storage section 332, a signal extraction section 333, and a matrix data setting section 334. The special light image generation section 331 performs image processing on the digital image signal input from the A/D conversion section 310 to generate a special light image. In the fourth embodiment, the special light image is a narrow-band light image. The digital image signal input to the special light image generation section 331 is the same as the digital image signal input to the normal light image generation section 321.

The narrow-band light image is generated as described below using the signal extraction section 333, the matrix data setting section 334, and the special light image generation section 331. Specifically, a known interpolation process is performed on the input digital image signal to generate a color image that includes R, G, and B channels. The color image is obtained by capturing the object using the first imaging element 250 in a state in which white light is applied to the object. The spectral reflectivity of the object at each pixel of the color image is estimated using a known spectrum estimation technique. The details of the spectrum estimation technique are disclosed in paragraphs [0054] to [0065] of JP-A-2000-115553, for example. Spectral image information in which each pixel has the spectrum reflectivity $O(\lambda)$ ($\lambda=380$ to 780) of the object in the range from 380 nm to 780 nm at intervals of 10 nm is thus acquired. The spectrum reflectivity at the coordinates (x, y) within the image is indicated by $O(\lambda)$x, y. The spectral emissivity of the white light source is indicated by $E(\lambda)$, the spectral transmittance of the optical system is indicated by $L(\lambda)$, the spectral sensitivity of the pixel corresponding to the color filter g2 of the second imaging element 260 (refer to the first embodiment) is indicated by $g2(\lambda)$, and the spectral sensitivity of the pixel corresponding to the color filter b2 of the second imaging element 260 is indicated by $b2(\lambda)$. The signal values G2'(x, y) and B2'(x, y) at the coordinates (x, y) of the G2' image and the B2' image corresponding to the G2 image and the B2 image (refer to the first embodiment) are calculated by the following expressions (17) and (18), respectively.

$$G2'(x, y)=\int E(\lambda)\cdot O(\lambda)\cdot L(\lambda)\cdot g2(\lambda)d\lambda \quad (17)$$

$$B2'(x, y)=\int E(\lambda)\cdot O(\lambda)\cdot L(\lambda)\cdot b2(\lambda)d\lambda \quad (18)$$

The G2' image and the B2' image can be acquired from the image signal obtained by the first imaging element 250 by performing the above calculations over the entire image.

A color image that includes R, G, and B channels is generated from the G2' image and the B2' image in the same manner as in the first embodiment. For example, a color image is generated by inputting the G2 image to the R channel, and inputting the B2 image to the G channel and the B channel. The special light image generation section 331 performs a white balance process, a grayscale transformation process, and the like on the generated color image, and outputs the resulting color image as a narrow-band light image. The special light image storage section 332 stores the special light image output from the special light image generation section 331.

The process performed after the images have been acquired by the normal light image acquisition section 320 and the special light image acquisition section 330 is the same as that described above in connection with the first to third embodiments.

According to the fourth embodiment, the second image acquisition section (special light image acquisition section 330 in a narrow sense) generates the second image based on the first image. More specifically, the second image acquisition section includes the signal extraction section 333 and the matrix data setting section 334. The signal extraction section 333 extracts a signal within the wavelength band of white light. The matrix data setting section 334 sets matrix data for calculating a signal within the specific wavelength band. The second image acquisition section calculates a signal within the specific wavelength band from the signal extracted by the signal extraction section 333 using the matrix data to generate the second image.

Figure 28:
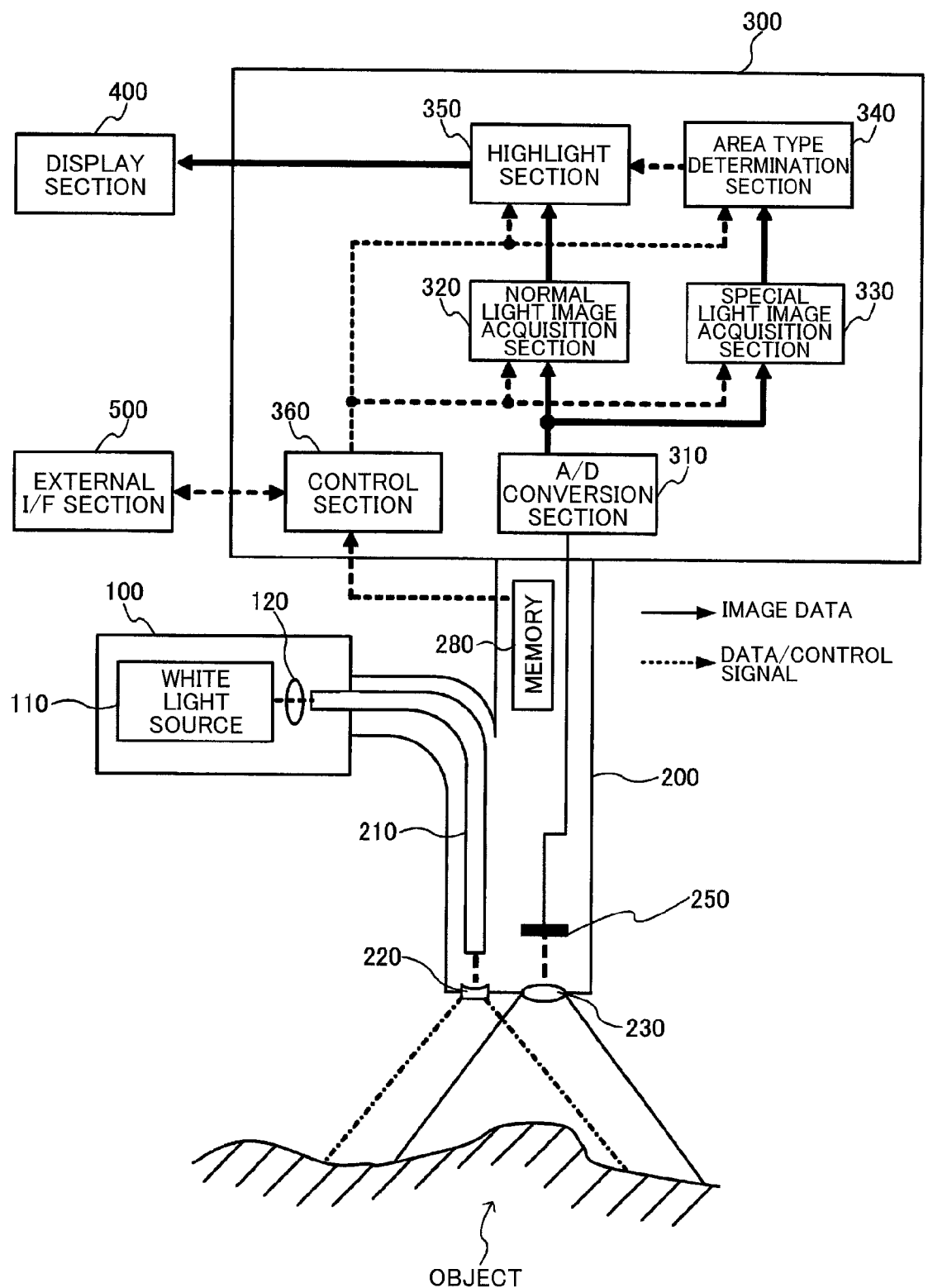
FIG. 28 illustrates another system configuration example according to one embodiment of the invention.

Since the second image can be generated based on the first image, an endoscope system can be implemented using only one imaging element, and the imaging section 200 can be reduced in size (see FIG. 28). Moreover, since the number of parts can be reduced, a reduction in cost can be achieved.

5. Fifth Embodiment

An outline of a fifth embodiment of the invention is described below with reference to FIG. 30. An object of the fifth embodiment is to determine the type of an object image in the second image, and perform the highlight process on the first image corresponding to the type of object image in the same manner as in the first embodiment.

In the fifth embodiment, the second image is a fluorescent image (see D1). The type of an object image in the second image is determined (D2). In the example illustrated in FIG. 30, a signal value (R, G, or B signal value) is used as the feature quantity for determining the type of the object image. An object image having a signal value equal to or larger than a given threshold value is determined to be a first type of object image, and an object image other than the first type of object image is determined to be a second type of object image. The first type of object image corresponds to a lesion area, and the second type of object image corresponds to an area (normal area) other than a lesion area. Specifically, since a fluorescent agent is concentrated in a specific lesion area, a lesion area has a specific color in the second image.

A highlight range is determined after determining the type of the object image. In the fifth embodiment, the highlight process is performed on an area of the first image that corresponds to the first type of object image (lesion area) (D4). Therefore, a range indicated by D5 is highlighted in the first image.

The highlight process is performed on the highlight range using a given method. In the fifth embodiment, the highlight process is implemented by adding and subtracting the signal value. More specifically, the value "feature quantity×gain" (gain is a given parameter) is subtracted from the R and G components of the first image, and the value "feature quantity×gain" is added to the B component of the first image (D6). The highlight process corresponding to the type of the object image can be performed by performing the highlight process on the first type of object image without performing the highlight process on the second type of object image. A normal light image in which the lesion area is highlighted (see D7) can thus be acquired.

Figure 31:
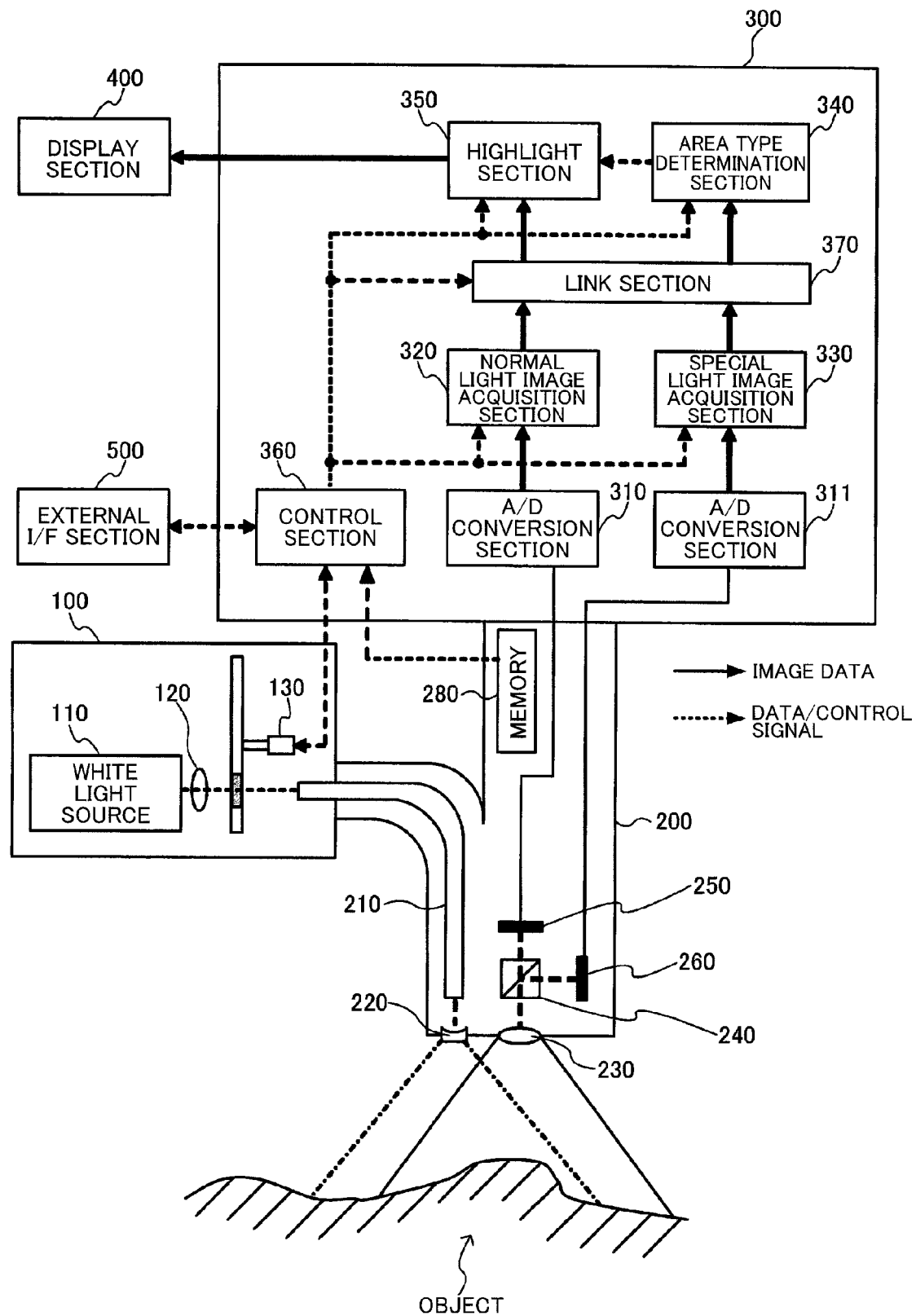
FIG. 31 illustrates another system configuration example according to one embodiment of the invention.

An endoscope system according to the fifth embodiment of the invention is described below with reference to FIG. 31. The endoscope system according to the fifth embodiment includes a light source section 100, an imaging section 200, an image processing section 300, a display section 400, and an external I/F section 500.

The light source section 100 includes a white light source 110 that emits white light, a condenser lens 120 that focuses light emitted from the light source on a light guide fiber 210, and a rotary filter 130 that extracts light within a specific wavelength band from white light.

Figure 32:
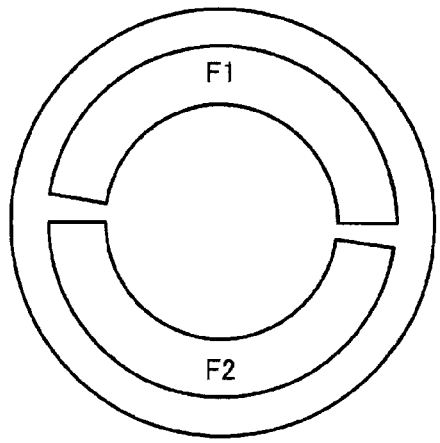
FIG. 32 illustrates a configuration example of a rotary filter.
Figure 33:
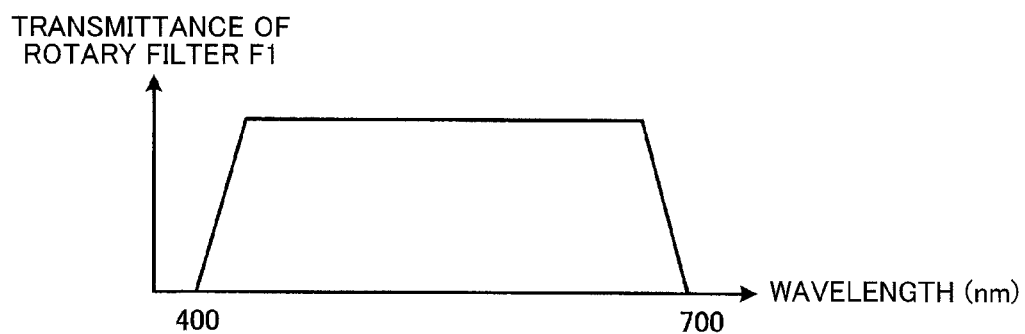
FIG. 33 illustrates the spectral characteristics of a filter F1.
Figure 34:
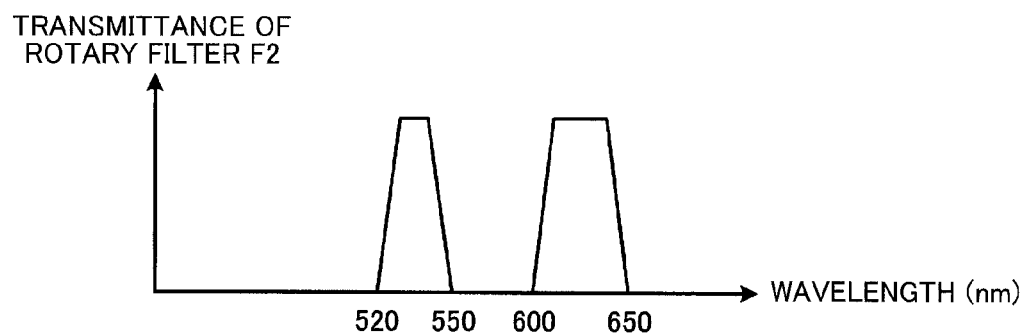
FIG. 34 illustrates the spectral characteristics of a filter F2.

As illustrated in FIG. 32, the rotary filter 130 includes filters F1 and F2 that differ in transmittance characteristics. The filter F1 allows light within a wavelength band of 400 to 700 nm to pass through (see FIG. 33). Specifically, the filter F1 allows white light to pass through. The filter F2 (comb filter) allows light within a wavelength band of 520 to 550 nm and light within a wavelength band of 600 to 650 nm to pass through (see FIG. 34). Light within a wavelength band of 520 to 550 nm extracted by the filter F2 excites a fluorescent agent (e.g., CY3) to produce fluorescence within a wavelength band of 560 to 600 nm. Light within a wavelength band of 600 to 650 nm extracted by the filter F2 excites a fluorescent agent (e.g., CY5) to produce fluorescence within a wavelength band of 670 to 710 nm. The fluorescent agent CY3 is specifically accumulated in a lesion area (e.g., epidermoid cancer) that may generally be observed in the gullet. The fluorescent agent CY5 is specifically accumulated in a lesion area (e.g., tumor) that may generally be observed in the large intestine.

The imaging section 200 is formed to be elongated and flexible (i.e., can be curved) so that the imaging section 200 can be inserted into a body cavity or the like. The imaging section 200 can be removed so that a different imaging section can be used depending on the organ to be observed. The imaging section 200 is normally referred to as a scope in the field of endoscopy. Specific examples of the scope include an upper gastrointestinal scope, a lower gastrointestinal scope, and the like.

The imaging section 200 includes the light guide fiber 210 that guides light focused by the light source section 100, an illumination lens 220 that diffuses light that has been guided by the light guide fiber 210, and illuminates an object, an objective lens 230 that focuses reflected light from the object, a dichroic mirror 240 that divides the focused reflected light and fluorescence into different optical paths, and a first imaging element 250 and a second imaging element 260 that detect the reflected light divided by the dichroic mirror 240.

Figure 3:
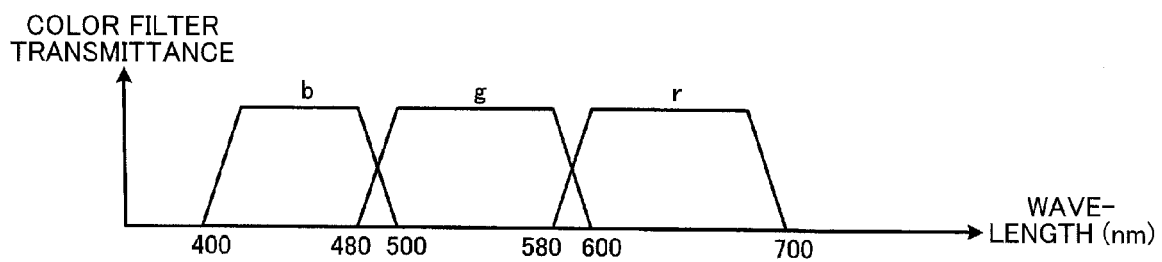
FIG. 3 illustrates the spectral characteristics of color filters r, g, and b.
Figure 35:
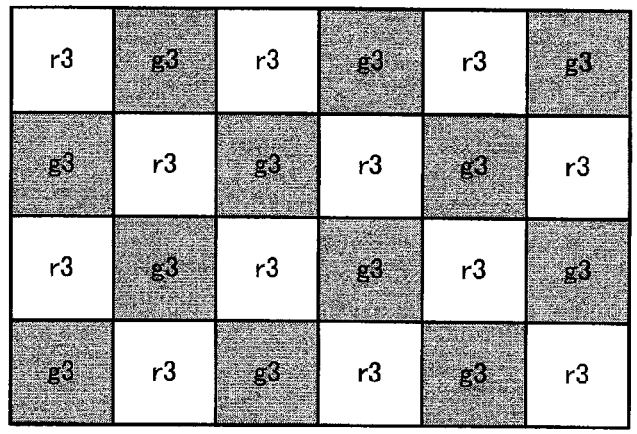
FIG. 35 is a view illustrating color filters g3 and r3.
Figure 36:
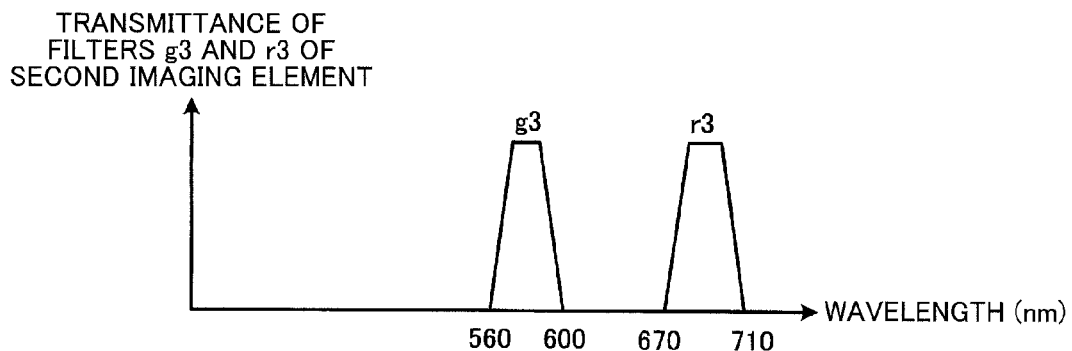
FIG. 36 illustrates the spectral characteristics of color filters g3 and r3.

The first imaging element 250 is a Bayer color imaging element having the R, and B spectral characteristics illustrated in FIG. 3, for example. The second imaging element 260 has a configuration in which color filters g3 and r3 are disposed in a staggered arrangement (see FIG. 35), for example. As illustrated in FIG. 36, the color filter g3 has transmittance characteristics that allow light within a wavelength of 560 to 600 nm to pass through, and the color filter r3 has transmittance characteristics that allow light within a wavelength of 670 to 710 nm to pass through, for example. These wavelength bands respectively correspond to the fluorescence wavelength of the fluorescent agent CY3 and the fluorescence wavelength of the fluorescent agent CY5.

The imaging section 200 includes a memory 280. The memory 280 stores an identification number specific to each scope. The memory 280 is connected to a control section 360. The control section 360 can specify the scope referring to the identification number stored in the memory 280. The control section 360 can also specify the organ to be observed by specifying the scope.

The image processing section 300 includes AD conversion sections 310 and 311, a normal light image acquisition section 320, a special light image acquisition section 330, an area type determination section 340, a highlight section 350, the control section 360, and a link section 370. The control section 360 is connected to the normal light image acquisition section 320, the special light image acquisition section 330, the area type determination section 340, the highlight section 350, and the link section 370, and controls the normal light image acquisition section 320, the special light image acquisition section 330, the area type determination section 340, the highlight section 350, and the link section 370.

The control section 360 is also connected to the rotary filter 130. The rotary filter 130 causes illumination light to be applied to the object (i.e., tissue in a body cavity) while sequentially switching the filters F1 and F2 by rotating a motor corresponding to a signal input from the control section 360. The control section 360 outputs information about the filter F1 or F2 disposed in the optical path to the normal light image acquisition section 320, the special light image acquisition section 330, and the link section 370 as a trigger signal.

The external I/F section 500 is an interface that allows the user to perform an input operation on the image processing device, for example.

The AD conversion section 310 converts an analog image signal output from the first imaging element 250 into a digital image signal, and outputs the digital image signal. The AD conversion section 311 converts an analog image signal output from the second imaging element 260 into a digital image signal, and outputs the digital image signal.

The normal light image acquisition section 320 acquires a normal light image from the digital image signal output from the AD conversion section 310. The special light image acquisition section 330 acquires a special light image from the digital image signal output from the AD conversion section 311.

The normal light image acquired by the normal light image acquisition section 320 and the special light image acquired by the special light image acquisition section 330 are output to the link section 370. In the fifth embodiment, since the normal light image and the special light image are alternately acquired by the normal light image acquisition section 320 and the special light image acquisition section 330, the link section 370 links the normal light image and the special light image. The details of the link section 370 are described later.

The normal light image linked by the link section 370 is output to the highlight section 350. The special light image linked by the link section 370 is output to the area type determination section 340. The area type determination section 340 determines the type of an object in the special light image, and outputs the determination result to the highlight section 350. The highlight section 350 performs a highlight process on the normal light image corresponding to the determination result output from the area type determination section 340, and outputs the resulting normal light image to the display section 400. The details of the area type determination section 340 and the highlight section 350 are described later.

The details of the normal light image acquisition section 320 will now be described with reference to FIG. 6. The normal light image acquisition section 320 includes a normal light image generation section 321 and a normal light image storage section 322. The normal light image generation section 321 specifies a period in which the filter F1 is positioned in the optical path based on the trigger signal transmitted from the control section 360, and performs image processing on the digital image signal converted from the analog image signal transmitted from the first imaging element in a period in which the filter F1 is positioned in the optical path to generate a normal light image. More specifically, the normal light image generation section 321 performs an interpolation process, a white balance process, a color conversion process, a grayscale transformation process, and the like on the digital image signal to generate a normal light image, and outputs the normal light image. The normal light image is an RGB image. The normal light image storage section 322 stores the normal light image output from the normal light image generation section 321 in a memory.

The details of the special light image acquisition section 330 will now be described with reference to FIG. 7. The special light image acquisition section 330 includes a special light image generation section 331 and a special light image storage section 332. The special light image generation section 331 specifies a period in which the filter F2 is positioned in the optical path based on the trigger signal transmitted from the control section 360, and performs image processing on the digital image signal converted from the analog image signal transmitted from the second imaging element in a period in which the filter F2 is positioned in the optical path to generate a special light image. In the fifth embodiment, the special light image is a fluorescent image. The fluorescent image is an RGB image.

Figure 37:
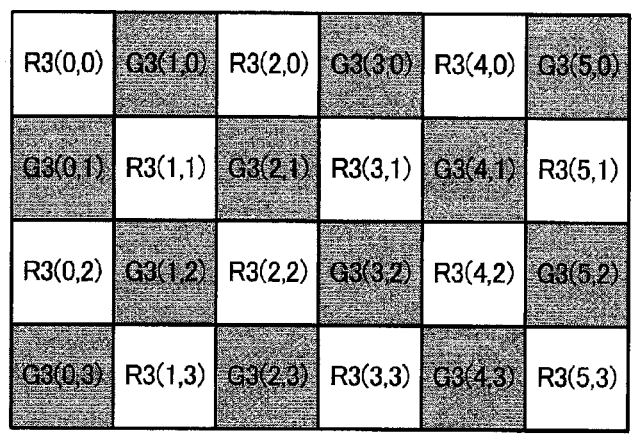
FIG. 37 is a view illustrating color filters g3 and r3.

The special light image generation section 331 generates the fluorescent image as described below. The second imaging element 260 has a configuration in which the color filters g3 and r3 are disposed in a staggered arrangement (see FIG. 37). Therefore, digital image signals illustrated in FIG. 37 are input to the special light image generation section 331. Note that G3(x, y) indicates the signal value of the g3 filter, and R3(x, y) indicates the signal value of the r3 filter. x and y are image coordinate values. The special light image generation section 331 performs an interpolation process on the image signal to generate a G3 image in which each pixel has the signal value of the filter g3, and an R3 image in which each pixel has the signal value of the filter r3. The interpolation process may be performed as shown by the expressions (1) and (2), for example.

A color image having R, G, and B signal values is generated from the G3 image and the R3 image in the same manner as the normal light image. For example, the color image is generated by inputting the signal value R3(x, y) to the R signal at the coordinates (x, y), and inputting the signal value G3(x, y) to the G and B signals at the coordinates (x, y). The special light image generation section 331 performs a white balance process, a grayscale transformation process, and the like on the generated color image, and outputs the resulting color image as a fluorescent image. The special light image storage section 332 stores the fluorescent image output from the special light image generation section 331 in a memory.

Figure 38:
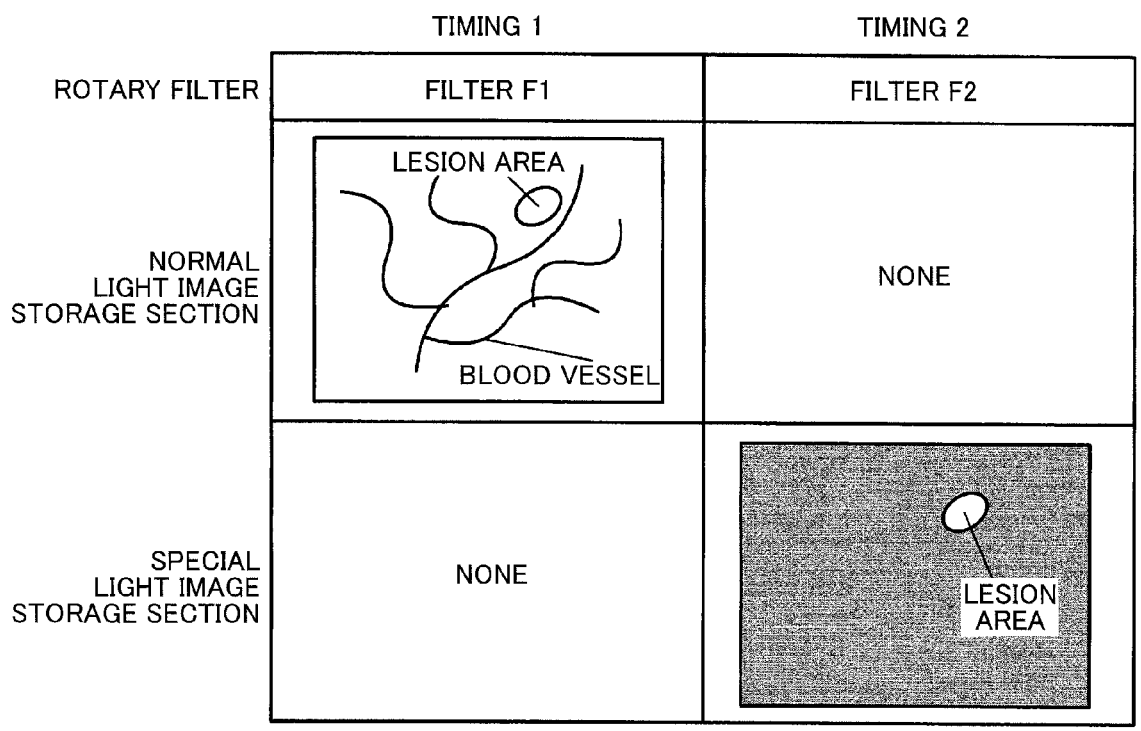
FIG. 38 illustrates an example of the combination of a filter and the resulting image at each timing.

FIG. 38 is a view illustrating the type of filter positioned in the optical path, and images stored in the normal light image storage section 322 and the special light image storage section 332. As illustrated in FIG. 38, the filter F1 is inserted into the optical path at a timing 1. In this case, white light is emitted as the illumination light. The normal light image is stored in the normal light image storage section 322, and an image is not stored in the special light image storage section 332. The filter F2 is inserted into the optical path at a timing 2. In this case, excitation light is emitted as the illumination light. Fluorescence produced from a lesion area where the fluorescent agent is accumulated is stored in the special light image storage section 332 as a pseudo-color image, and an image is not stored in the normal light image storage section 322. The normal light image storage section 322 and the special light image storage section 332 can store a plurality of images.

The details of the link section 370 will now be described. In the fifth embodiment, since the normal light image and the special light image are alternately acquired by the normal light image acquisition section 320 and the special light image acquisition section 330, the link section 370 links the normal light image and the special light image. The process of the link section 344 according to the fifth embodiment is described in detail below.

Figure 39:
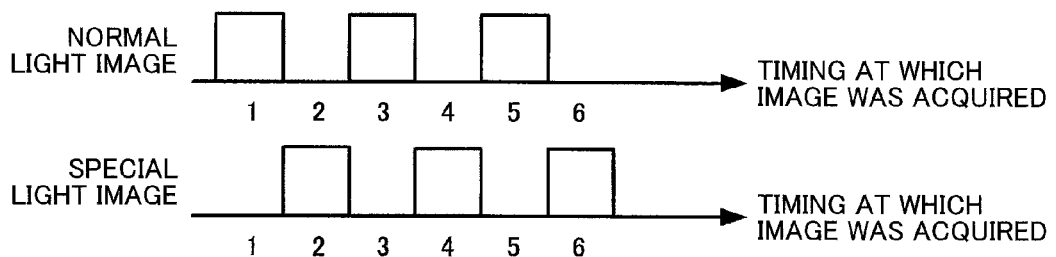
FIG. 39 illustrates an example of acquisition timings of a normal light image and a special light image.

FIG. 39 is a view illustrating a timing at which the image stored in the normal light image storage section 322 was acquired, and a timing at which the image stored in the special light image storage section 332 was acquired. The link section 370 sequentially reads the normal light image and the fluorescent image that are linked so that the difference in image acquisition timing becomes a minimum from the normal light image storage section 322 and the special light image storage section 332 according to a control signal input from the control section 360. Specifically, the link section 370 reads the normal light image acquired at the timing 1 and the fluorescent image acquired at the timing 2, and then reads the normal light image acquired at the timing 2 and the fluorescent image acquired at the timing 3. The link section 370 thus acquires the normal light image and the fluorescent image at the same interval as the image acquisition interval.

The details of the area type determination section 340 will now be described. The area type determination section 340 is configured in the same manner as in the first embodiment (see FIG. 9). The area type determination section 340 performs the process in the same manner as in the first embodiment.

The feature quantity calculation section 342 calculates the feature quantity corresponding to the organ to be observed. The fluorescent agent CY3 used in connection with the fifth embodiment is specifically accumulated in a lesion area (e.g., epidermoid cancer) that may generally be observed in the gullet, and the fluorescent agent CY5 used in connection with the fifth embodiment is specifically accumulated in a lesion area (e.g., tumor) that may generally be observed in the large intestine. Therefore, the G or B signal to which the fluorescence signal of the fluorescent agent CY3 is input may be used as the feature quantity when observing the gullet, and the R signal to which the fluorescence signal of the fluorescent agent CY5 is input may be used as the feature quantity when observing the large intestine. The control section 360 may specify the organ to be observed referring to the identification number specific to each scope stored in the memory 280, or the user may designate the organ to be observed via the external I/F section 500.

An example in which the large intestine is observed (diagnosed) is described below. When observing the large intestine, the feature quantity calculation section 342 calculates the average value of the R signal of each pixel of each local area set by the local area setting section 341. The feature quantity calculation section 342 outputs the calculated average value of the R signals to the type determination section 343 as the feature quantity. Note that the feature quantity of the local area a(m, n) is indicated by f(m, n).

The type determination section 343 determines the type of object in each local area based on the feature quantity f(m, n) of each local area calculated by the feature quantity calculation section 342.

Since the fluorescent agent CY5 used in connection with the fifth embodiment is specifically accumulated in a lesion area (e.g., tumor), a local area in which a lesion area (e.g., tumor) is present tends to have a feature quantity f(m, n) larger than that of a local area in which a lesion area is not present. Therefore, a local area having a feature quantity f(m, n) larger than a threshold value F_th may be determined to be a lesion area (e.g., tumor). The threshold value F_th may be the average feature quantity f(m, n) of each local area (see the following expression (19)), for example.

$$F\_th = \frac{1}{(M+1)(N+1)} \sum_{m=0}^{M} \sum_{n=0}^{N} f(m, n) \quad (19)$$

The type determination section 343 outputs the coordinates and the feature quantity f(m, n) of each local area that has been determined to be a lesion area (e.g., tumor), and tag information that indicates the determination result to the area selection section 344. The tag information about an area that has been determined to be a lesion area (e.g., tumor) may be set to "1", for example.

The area selection section 344 calculates the position of each pixel of each local area a(m, n) that has been determined to be a lesion area (e.g., tumor) by the type determination section 343 from the coordinates of each local area and information about each pixel included in each local area, and outputs the position of each pixel thus calculated, the tag information, and the feature quantity f(x, y) to the highlight section 350. Note that the feature quantity f(x, y) at the position of each pixel may be the feature quantity f(m, n) of the local area a(m, n) to which each pixel belongs.

The details of the highlight section 350 are described below. The highlight section 350 performs the highlight process on each pixel of the normal light image that corresponds to the position of each pixel output from the area type determination section 340. The normal light image subjected to the highlight process is output to the display section 400.

The highlight process performed on a pixel that has been determined to be a lesion area (e.g., tumor) (i.e., tag value="1") may be implemented by a color conversion process shown by the following expression (20), for example.

$$R\_out(x, y) = R(x, y) - \text{gain} * f(x, y)$$

$$G\_out(x, y) = G(x, y) - \text{gain} * f(x, y)$$

$$B\_out(x, y) = B(x, y) + \text{gain} * f(x, y) \quad (20)$$

where, R(x, y), G(x, y), and B(x, y) are the R, G, and B signal values of the normal light image at the coordinates (x, y) before the color conversion process is performed, and R_out(x, y), G_out(x, y), and B_out(x, y) are the R, G, and B signal values of the normal light image at the coordinates (x, y) after the color conversion process has been performed.

gain is an arbitrary coefficient in the range of 0 to 1. The coefficient gain may be set by the user via the external IN section 500, or may be set in advance corresponding to the organ to be observed. The control section 360 may specify the organ to be observed referring to the identification number specific to each scope stored in the memory 280, or the user may designate the organ to be observed via the external I/F section 500.

Since a lesion area (e.g., tumor) is drawn as a blue area differing from a normal area by performing the above process, it is possible to prevent a situation in which a lesion area is missed while reducing the burden on the doctor during diagnosis using the normal light image and the fluorescent image.

Although an example in which the color conversion process is performed on the normal light image based on the feature quantity has been described above, the invention is not limited thereto. For example, an arbitrary color conversion process or a luminance conversion process may be performed based on the feature quantity.

Although the fifth embodiment utilizes the fluorescent agent, intrinsic fluorescence produced by collagen in tissue may be observed (e.g., autofluorescence imaging (AFI)), for example. In this case, light within a wavelength band of 390 to 470 nm may be used as excitation light, and the transmission characteristics of the color filter of the second imaging element may be changed to 490 to 625 nm (i.e., the wavelength band of intrinsic fluorescence).

Light within a wavelength band of 790 to 820 nm (infrared light) and light within a wavelength band of 905 to 970 nm (infrared light) may be used as illumination light after intravenously injecting indocyanine green (ICG), and a pseudo-color image may be generated from reflected light images, and used as the special light image (e.g., infrared imaging (IRI)).

Note that each section of the image processing section 300 need not necessarily be implemented by hardware. For example, a CPU may perform the process of each section on an image acquired in advance in the same manner as in the first embodiment. Specifically, the process of each section may be implemented by software by causing the CPU to execute a program. Alternatively, the process of each section may partially be implemented by software.

Figure 40:
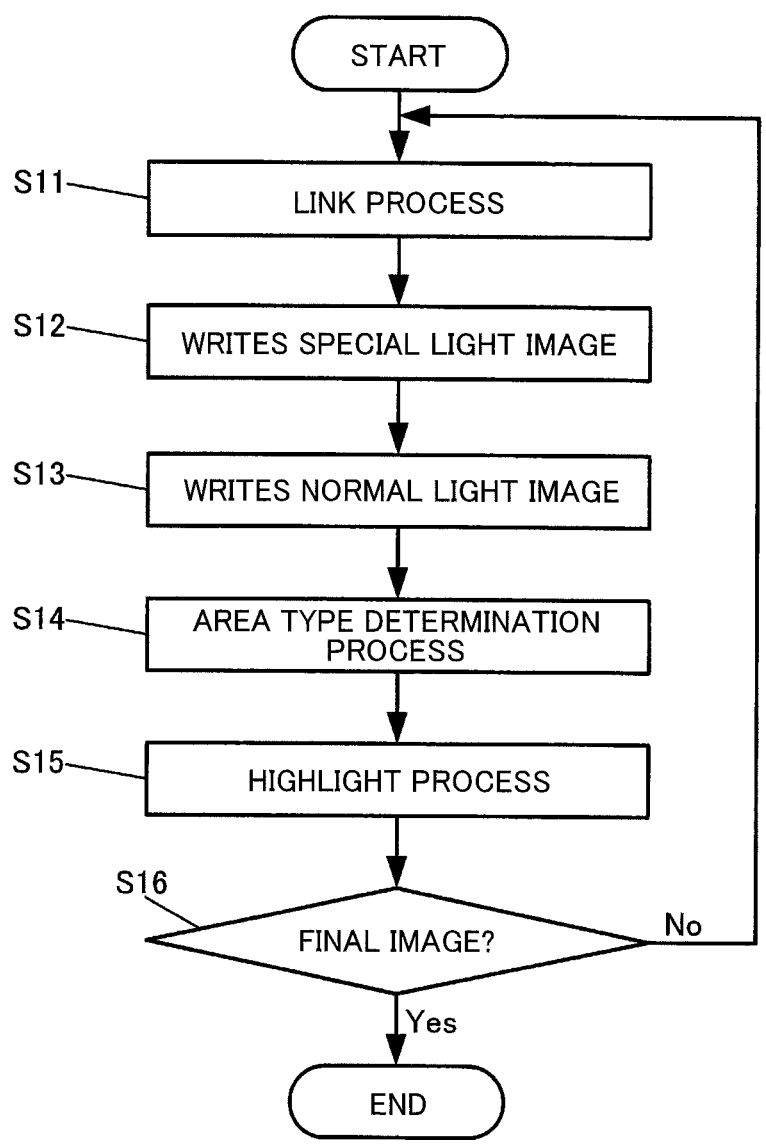
FIG. 40 is another flowchart illustrating a process according to one embodiment of the invention.

A process performed on the normal light image and the fluorescent image acquired in advance when implementing the process of the area type determination section 340, the process of the highlight section 350, and the process of the link section 370 illustrated in FIG. 31 by software is described below using a flowchart illustrated in FIG. 40.

In Step 11, the normal light image and the fluorescent image that have been alternately acquired are linked based on image acquisition timing information. The fluorescent image is written into the memory (Step 12), and the normal light image linked to the fluorescent image is then written into the memory (Step 13).

Figure 41:
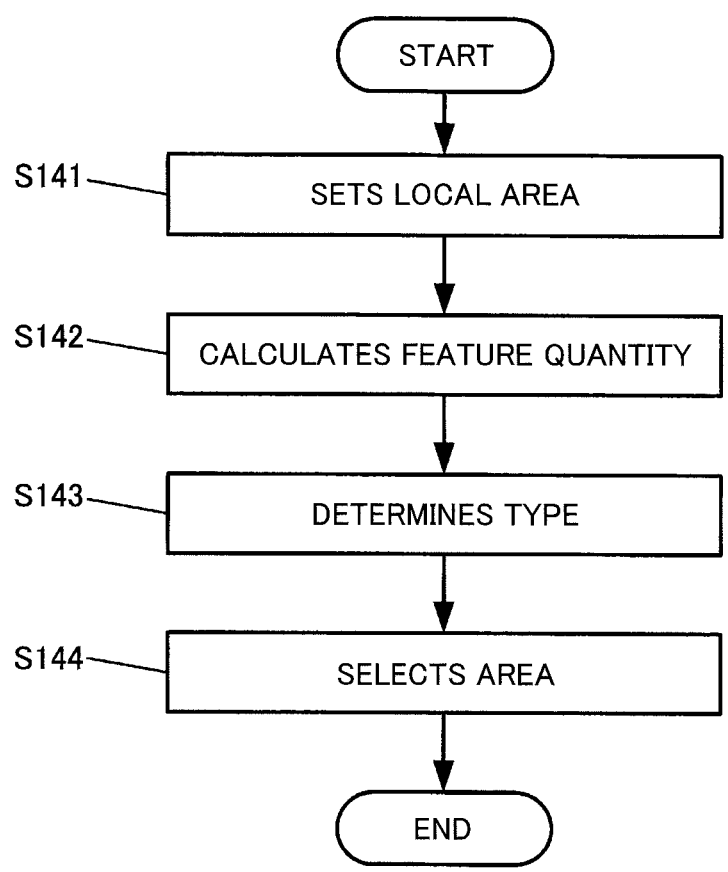
FIG. 41 is another flowchart illustrating an area type determination process.

FIG. 41 illustrates the details of the area type determination step (Step 14). In the local area setting step, a plurality of local areas are set within the fluorescent image in the same manner as in the first embodiment (Step 141). In the feature quantity calculation step, the feature quantity of each local area is calculated corresponding to the organ to be observed in the same manner as described above (Step 142). In the type determination step, whether or not each local area is a lesion area (e.g., tumor) is determined by the threshold process (Step 143). In the area election step, the position of each pixel included in each local area that has been determined to be a lesion area is calculated from the coordinates of each local area information about each pixel included in each local area (Step 144).

In the highlight step (Step 15), the highlight process is performed on the normal light image using the method shown by the expression (19). The process ends when all of the images have been processed. The process is repeated until all of the images have been processed (Step 16).

According to the fifth embodiment, the type determination section 343 changes the feature quantity calculation process corresponding to the organ to which the object image belongs.

This makes it possible to change the feature quantity used to determine the type of object image corresponding to the organ to be observed. Specifically, the fluorescence signal G3 of the fluorescent agent CY3 is input to the G and B channels, and the fluorescence signal R3 of the fluorescent agent CY5 is input to the R channel during observation using the fluorescent agents CY3 and CY5. The fluorescent agent CY3 tends to be specifically accumulated in a lesion area (e.g., epidermoid cancer) that may generally be observed in the gullet, and the fluorescent agent CY5 tends to be specifically accumulated in a lesion area (e.g., tumor) that may generally be observed in the large intestine. Therefore, the G or B signal to which the fluorescence signal G3 of the fluorescent agent CY3 is input may be used as the feature quantity when observing the gullet, and the R signal to which the fluorescence signal R3 of the fluorescent agent CY5 is input may be used as the feature quantity when observing the large intestine.

The highlight section 350 may perform the highlight process that enhances the luminance component or the color component of the corresponding attention area in the first image based on the color feature quantity calculated from the second image.

This makes it possible to add the color feature quantity (i.e., the G or B signal when observing the gullet, and the R signal when observing the large intestine) to the luminance component (Y component) or the color component (R, G, or B component) of the corresponding attention area.

6. Sixth Embodiment

Figure 42:
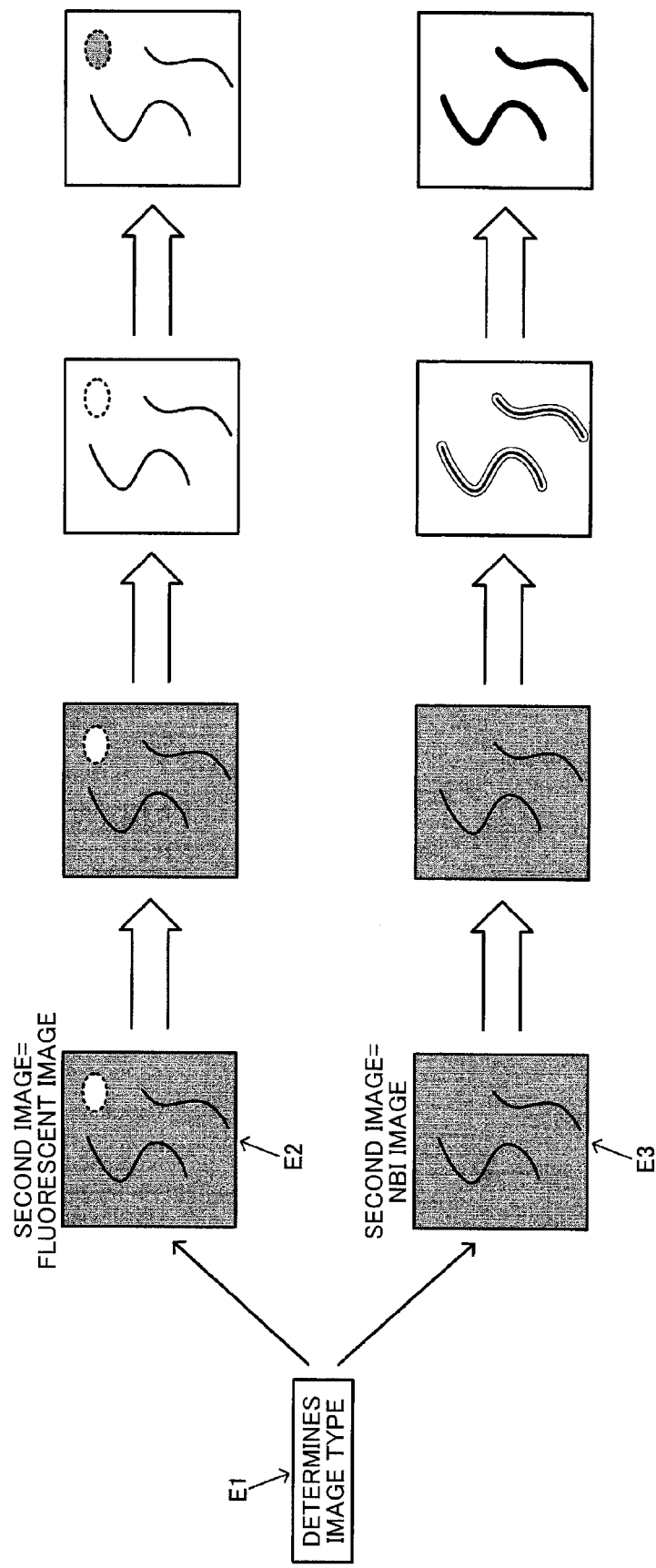
FIG. 42 is another view illustrating a type determination process and a highlight process.

An outline of a sixth embodiment of the invention is described below with reference to FIG. 42. An object of the sixth embodiment is to determine the type of an object image in the second image, and perform the highlight process on the first image corresponding to the type of object image in the same manner as in the first embodiment. Since an endoscope system according to the sixth embodiment is configured so that a plurality of second images can be acquired, it is necessary to take account of the type of object image and the type of second image.

The type of second image is determined (E1). The second image may be a fluorescent image (E2) or an NBI image (E3). The subsequent process differs depending on whether the second image is a fluorescent image or an NBI image. This makes it possible to perform the highlight process on the first image corresponding to the type of the second image.

Figure 30:
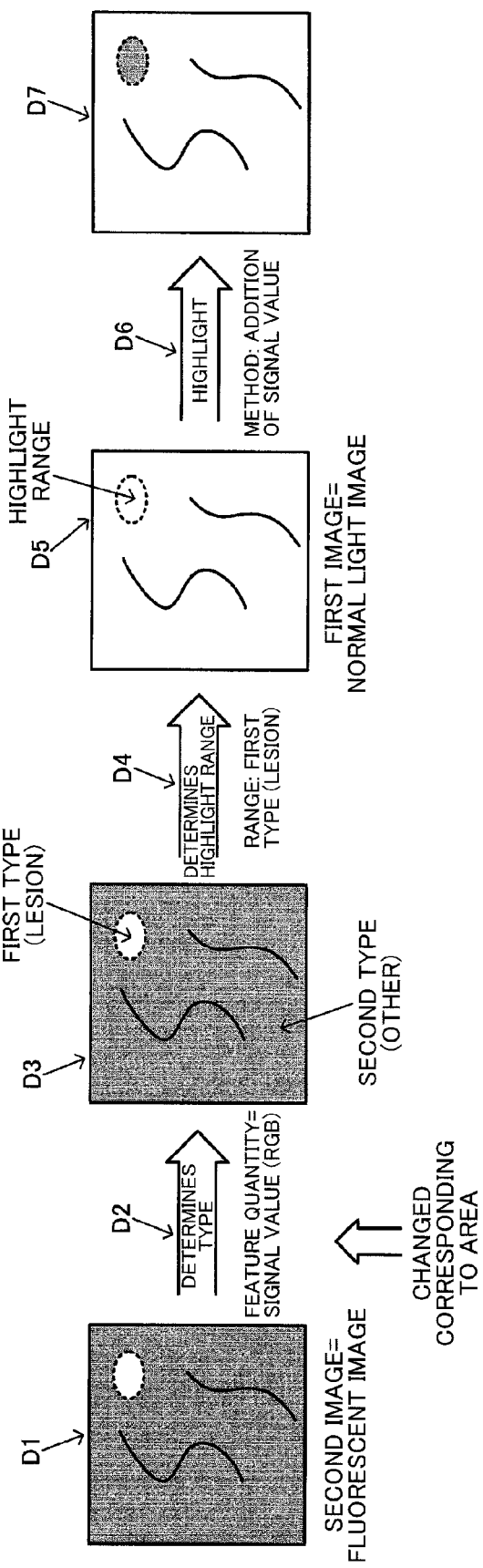
FIG. 30 is another view illustrating a type determination process and a highlight process.

When the second image is a fluorescent image, the subsequent process is performed in the same manner as illustrated in FIG. 30 (fifth embodiment). When the second image is an NBI image, the subsequent process is performed in the same manner as illustrated in FIG. 24 (third embodiment).

Figure 43:
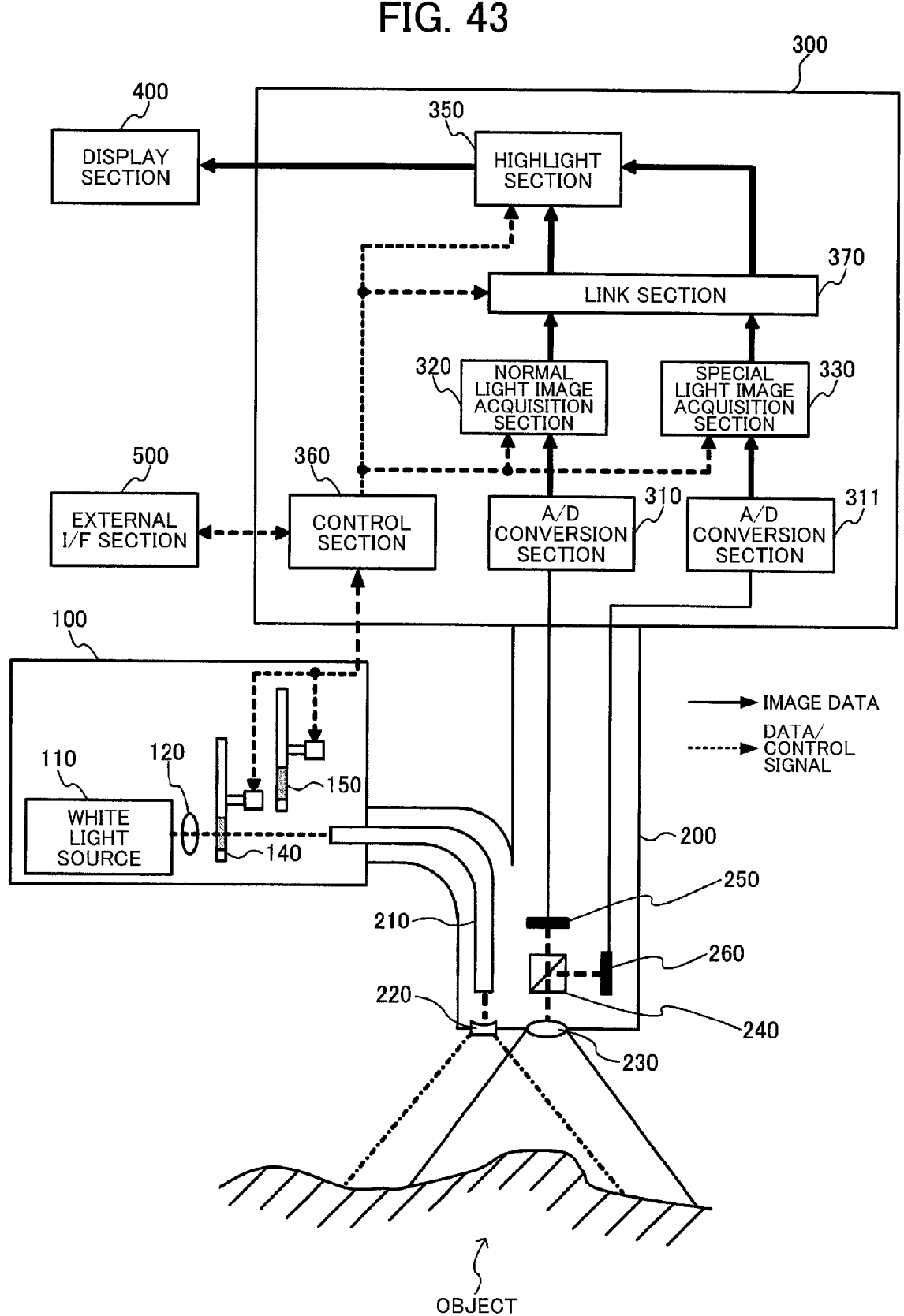
FIG. 43 illustrates yet another system configuration example according to one embodiment of the invention.

The endoscope system according to the sixth embodiment is now described with reference to FIG. 43. The endoscope system according to the sixth embodiment includes a light source section 100, an imaging section 200, an image processing section 300, a display section 400, and an external I/F section 500.

The light source section 100 includes a white light source 110 that emits white light, a condenser lens 120 that focuses light emitted from the light source on a light guide fiber 210, and a first rotary filter 140 and a second rotary filter 150 that extract light within a specific wavelength band from white light.

Note that the first rotary filter 140 and the second rotary filter 150 are controlled exclusively. Specifically, when the first rotary filter 140 is inserted into the optical path of light emitted from the white light source 110, the second rotary filter 150 is not inserted into the optical path of light emitted from the white light source 110. When the second rotary filter 150 is inserted into the optical path of light emitted from the white light source 110, the first rotary filter 140 is not inserted into the optical path of light emitted from the white light source 110. The user may designate the rotary filter via the external PF section 500, and a control section 360 may exclusively control the first rotary filter 140 and the second rotary filter 150 according to instructions from the user, for example.

Figure 44:
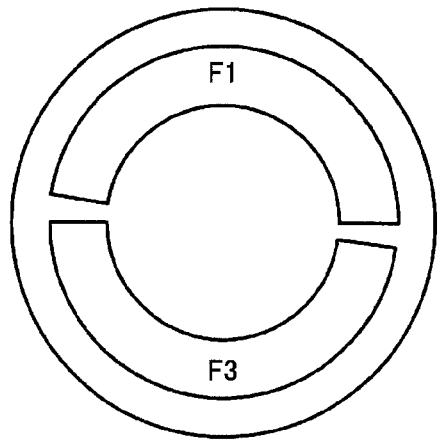
FIG. 44 illustrates a configuration example of a rotary filter.
Figure 46:
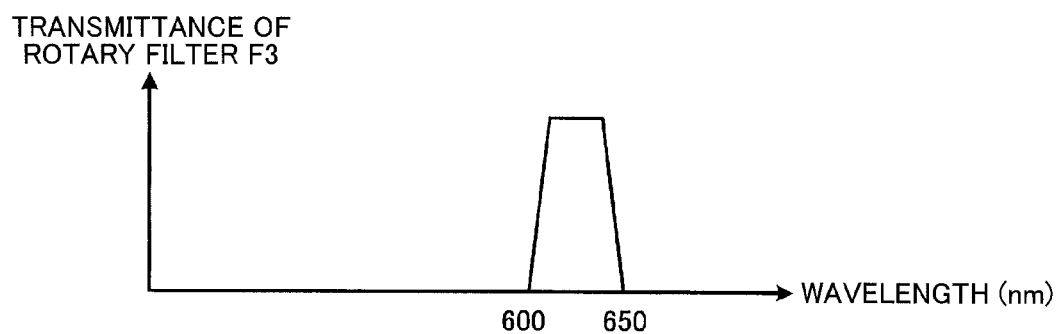
FIG. 46 illustrates the spectral characteristics of a filter F3.

As illustrated in FIG. 44, the first rotary filter 140 includes filters F1 and F3 that differ in transmittance characteristics. The filter F1 allows light within a wavelength band of 400 to 700 nm to pass through (see FIG. 33). The filter F3 allows light within a wavelength band of 600 to 650 nm to pass through (see FIG. 46). Light within a wavelength band of 600 to 650 nm extracted by the filter F3 excites a fluorescent agent (e.g., CY5) to produce fluorescence within a wavelength band of 670 to 710 nm. The fluorescent agent CY5 is specifically accumulated in a lesion area (e.g., tumor).

Figure 45:
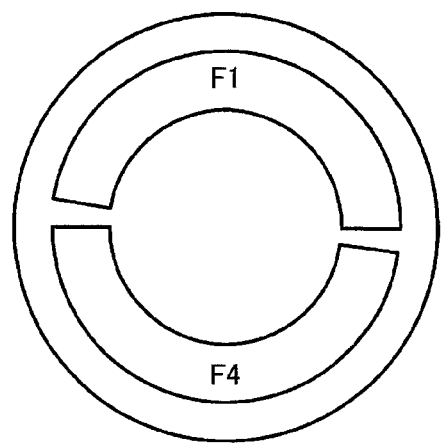
FIG. 45 illustrates a configuration example of a rotary filter.
Figure 47:
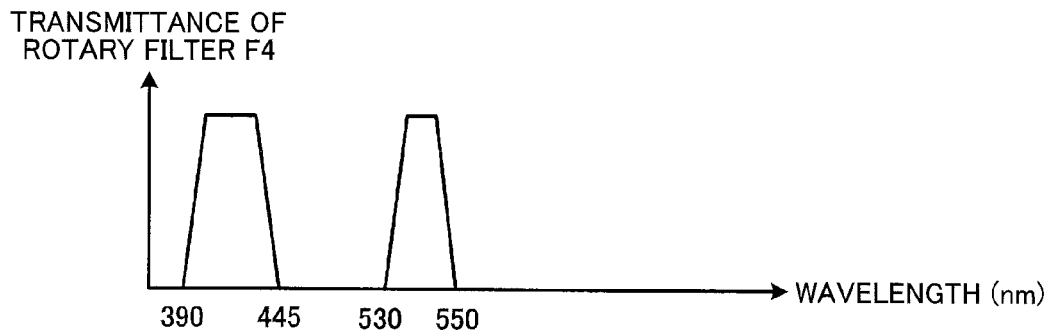
FIG. 47 illustrates the spectral characteristics of a filter F4.

As illustrated in FIG. 45, the second rotary filter 150 includes filters F1 and F4 that differ in transmittance characteristics. The filter F4 (comb filter) allows light within a wavelength band of 390 to 445 nm and light within a wavelength band of 530 to 550 nm to pass through (see FIG. 47). The characteristics of the filter F1 included in the second rotary filter 150 are identical with the characteristics of the filter F1 included in the first rotary filter 140.

The imaging section 200 is formed to be elongated and flexible (i.e., can be curved) so that the imaging section 200 can be inserted into a body cavity or the like. The imaging section 200 includes the light guide fiber 210 that guides light focused by the light source section 100, an illumination lens 220 that diffuses light that has been guided by the light guide fiber 210, and illuminates an object, an objective lens 230 that focuses reflected light from the object, a dichroic mirror 240 that divides the focused reflected light into different optical paths, and a first imaging element 250 and a second imaging element 260 that detect the reflected light divided by the dichroic mirror 240.

Figure 48:
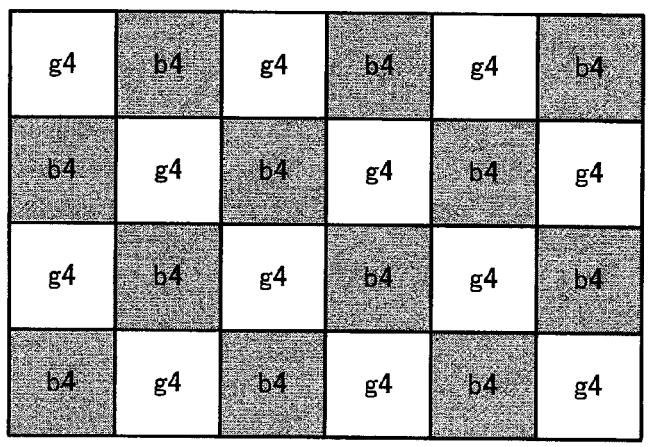
FIG. 48 is a view illustrating color filters g4 and b4.
Figure 49:
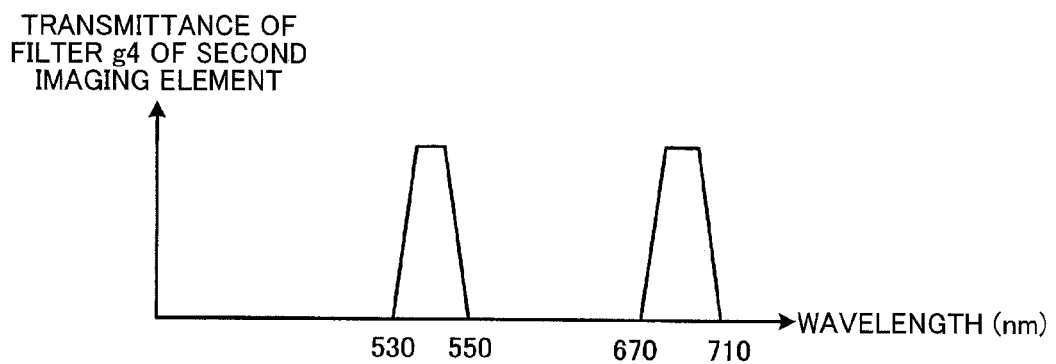
FIG. 49 illustrates the spectral characteristics of a color filter g4.
Figure 50:
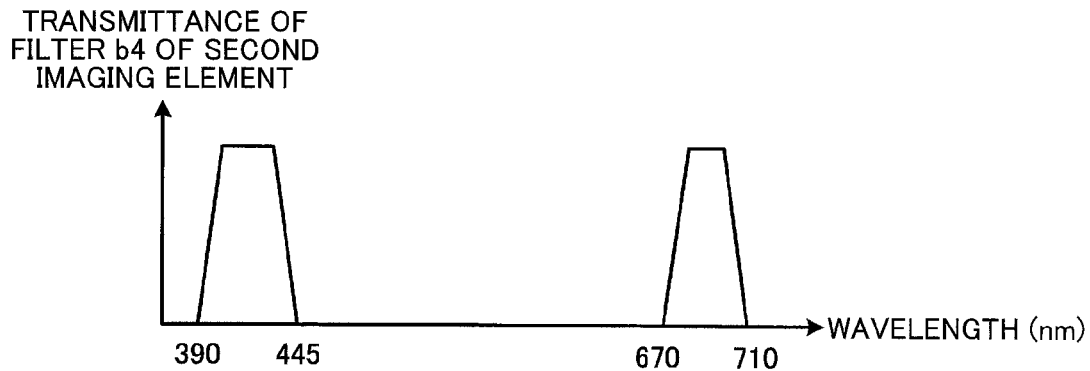
FIG. 50 illustrates the spectral characteristics of a color filter b4.

The first imaging element 250 is a Bayer color imaging element having the R, and B spectral characteristics illustrated in FIG. 3, for example. The second imaging element 260 has a configuration in which color filters g4 and b4 are disposed in a staggered arrangement (see FIG. 48), for example. As illustrated in FIG. 49, the color filter g4 (comb filter) allows light within a wavelength band of 530 to 550 nm and light within a wavelength band of 670 to 710 nm to pass through, for example. As illustrated in FIG. 50, the color filter b4 (comb filter) allows light within a wavelength band of 390 to 445 nm and light within a wavelength band of 670 to 710 nm to pass through, for example. The wavelength band of 670 to 710 nm common to the color filters g4 and b4 corresponds to the fluorescence wavelength of the fluorescent agent CY5.

The image processing section 300 includes AD conversion sections 310 and 311, a normal light image acquisition section 320, a special light image acquisition section 330, a highlight section 350, the control section 360, and a link section 370. The control section 360 is connected to the normal light image acquisition section 320, the special light image acquisition section 330, the highlight section 350, and the link section 370, and controls the normal light image acquisition section 320, the special light image acquisition section 330, the highlight section 350, and the link section 370.

The control section 360 is also connected to the first rotary filter 140 and the second rotary filter 150. The first rotary filter 140 and the second rotary filter 150 cause illumination light to be applied to the object (i.e., tissue in a body cavity) while sequentially switching the filters F1 and F3 or the filters F1 and F4 by rotating a motor according to a signal output from the control section 360. The control section 360 outputs information about the rotary filter inserted into the optical path and information about the filter F1, F3, or F4 disposed in the optical path to the normal light image acquisition section 320, the special light image acquisition section 330, the highlight section 350, and the link section 370. The information output from the control section 360 is a flag signal and a trigger signal. The flag signal indicates whether the first rotary filter 140 or the second rotary filter 150 is inserted into the optical path. The trigger signal indicates the filter F1, F3, or F4 that is disposed in the optical path.

The external I/F section 500 is an interface that allows the user to perform an input operation on the image processing device, for example.

The AD conversion section 310 converts an analog image signal output from the first imaging element 250 into a digital image signal, and outputs the digital image signal. The AD conversion section 311 converts an analog image signal output from the second imaging element 260 into a digital image signal, and outputs the digital image signal.

The normal light image acquisition section 320 acquires a normal light image from the digital image signal output from the AD conversion section 310. The special light image acquisition section 330 acquires a special light image from the digital image signal output from the AD conversion section 311.

The normal light image acquired by the normal light image acquisition section 320 and the special light image acquired by the special light image acquisition section 330 are output to the link section 370. In the sixth embodiment, since the normal light image and the special light image are alternately acquired by the normal light image acquisition section 320 and the special light image acquisition section 330, the link section 370 links the normal light image and the special light image. The process of the link section 370 is the same as that described above in connection with the fifth embodiment.

The normal light image and the special light image linked by the link section 370 are output to the highlight section 350. The highlight section 350 performs the highlight process on the normal light image corresponding to the type of the special light image, and outputs the resulting normal light image to the display section 400. The details of the highlight section 350 are described later.

The details of the normal light image acquisition section 320 are described below with reference to FIG. 6. The normal light image acquisition section 320 includes a normal light image generation section 321 and a normal light image storage section 322. The normal light image generation section 321 specifies a period in which the filter F1 is positioned in the optical path based on the trigger signal transmitted from the control section 360, and performs image processing on the digital image signal converted from the analog image signal transmitted from the first imaging element in a period in which the filter F1 is positioned in the optical path to generate a normal light image. More specifically, the normal light image generation section 321 performs an interpolation process, a white balance process, a color conversion process, a grayscale transformation process, and the like on the digital image signal to generate a normal light image, and outputs the normal light image. The normal light image is an RGB image. The normal light image storage section 322 stores the normal light image output from the normal light image generation section 321 in a memory. The normal light image storage section 322 can store a plurality of images.

The details of the special light image acquisition section 330 are described below with reference to FIG. 7. The special light image acquisition section 330 includes a special light image generation section 331 and a special light image storage section 332. The special light image generation section 331 specifies whether the first rotary filter 140 or the second rotary filter 150 is inserted into the optical path based on the flag signal transmitted from the control section 360, and generates the special light image corresponding to the determination result as to whether the first rotary filter 140 or the second rotary filter 150 is inserted into the optical path. The special light image generation method differs between the case where the first rotary filter 140 is inserted into the optical path and the case where the second rotary filter 150 is inserted into the optical path as described below.

When the first rotary filter 140 is inserted into the optical path, the special light image acquisition section 330 specifies a period in which the filter F3 is positioned in the optical path based on the trigger signal, and performs image processing on the digital image signal output from the AD conversion section 311 in a period in which the filter F3 is positioned in the optical path to generate a special light image. The filter F3 allows light within a wavelength band that excites the fluorescent agent CY5 to produce fluorescence to pass through. The fluorescence wavelength band of the fluorescent agent CY5 is 670 to 710 nm The color filters g4 and b4 used for the second imaging element 260 allow light within the above fluorescence wavelength band to pass through. Therefore, a fluorescence signal of the fluorescent agent CY5 is output from the second imaging element 260. Accordingly, the special light image acquired when the first rotary filter 140 is inserted into the optical path is a fluorescence image. The special light image generation section 331 performs a grayscale transformation process on the digital image signal output from the AD conversion section 311 to generate a fluorescent image, and outputs the generated fluorescent image to the special light image storage section 332. The fluorescent image is a monochromatic image. The special light image storage section 332 stores the fluorescent image output from the special light image generation section 331 in a memory.

When the second rotary filter 150 is inserted into the optical path, the special light image acquisition section 330 specifies a period in which the filter F4 is positioned in the optical path based on the trigger signal, and performs image processing on the digital image signal output from the AD conversion section 311 in a period in which the filter F4 is positioned in the optical path to generate a special light image. The filter F4 allows narrow-band light within a wavelength band of 390 to 445 nm and narrow-band light within a wavelength band of 530 to 550 nm to pass through. The second imaging element 260 has a configuration in which the color filters g4 and b4 are disposed in a staggered arrangement (see FIG. 37), as described above. The color filter g4 allows light within a wavelength band of 530 to 550 nm to pass through, and the color filter b4 allows light within a wavelength band of 390 to 445 nm to pass through. Therefore, the digital image signal input to the special light image generation section 331 when the second rotary filter 150 is inserted into the optical path is the same as the digital image signal input to the special light image generation section 331 in the first embodiment. Therefore, the special light image generation section 331 generates a narrow-band light image in the same manner as in the first embodiment, and outputs the generated narrow-band light image to the special light image storage section 332. The narrow-band light image is an RGB image. The special light image storage section 332 stores the narrow-band light output from the special light image generation section 331 in a memory. The special light image storage section 332 can store a plurality of images.

Figure 51:
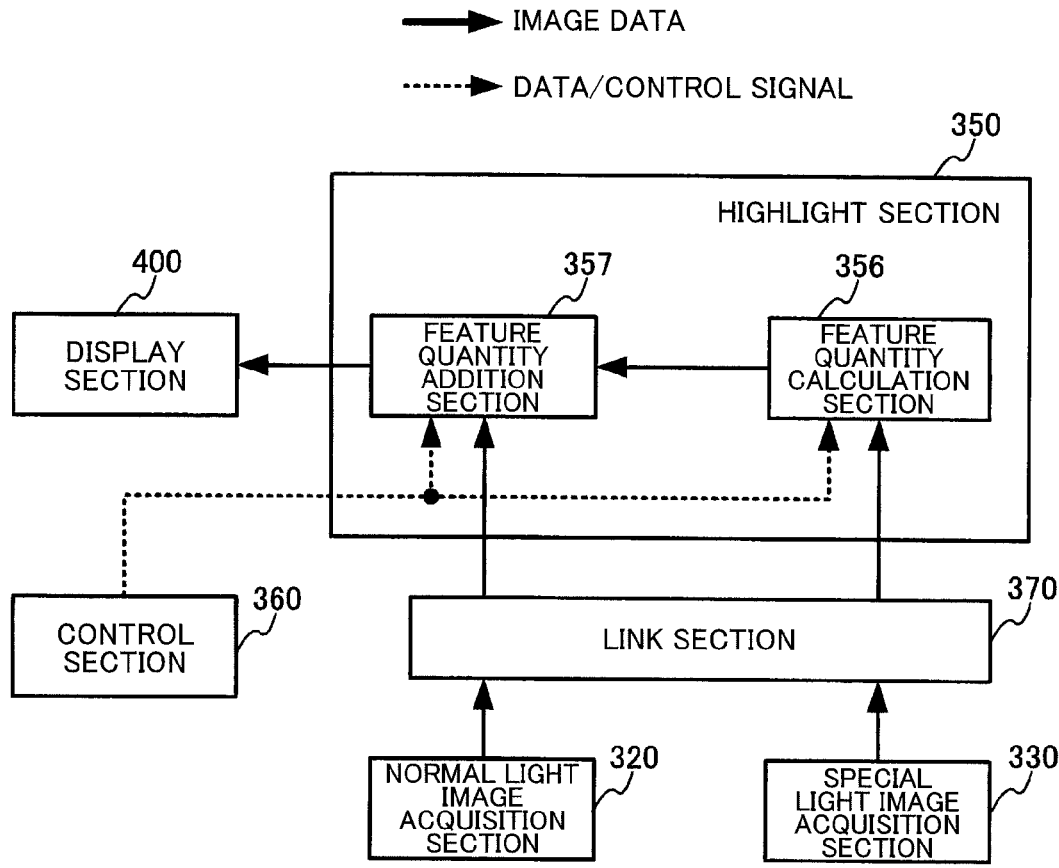
FIG. 51 illustrates another configuration example of a highlight section.

The details of the highlight section 350 are described below. As illustrated in FIG. 51, the highlight section 350 includes a feature quantity calculation section 356 and a feature quantity addition section 357. The special light image that has been linked to the normal light image by the link section 370 is output to the feature quantity calculation section 356. The normal light image that has been linked to the special light image by the link section 370 is output to the feature quantity addition section 357. The control section 360 is connected to the feature quantity calculation section 356 and the feature quantity addition section 357, and controls the feature quantity calculation section 356 and the feature quantity addition section 357.

The feature quantity calculation section 356 calculates the feature quantity corresponding to the type of the special light image. More specifically, the feature quantity calculation section 356 specifies whether the first rotary filter 140 or the second rotary filter 150 included in the light source section 100 is inserted into the optical path based on the flag signal transmitted from the control section 360, and calculates the feature quantity corresponding to the determination result as to whether the first rotary filter 140 or the second rotary filter 150 is inserted into the optical path.

The special light image output from the link section 370 when the first rotary filter 140 is inserted into the optical path is a monochromatic fluorescent image. In this case, the feature quantity calculation section 356 outputs the signal value at the position of each pixel of the input fluorescent image (x, y) to the feature quantity addition section 357 as the feature quantity. Note that the feature quantity at the pixel position (x, y) is indicated by f'(x, y).

The special light image output from the link section 370 when the second rotary filter 150 is inserted into the optical path is a narrow-band light image. In this case, the feature quantity calculation section 356 calculates the edge quantity $E(x, y)$ of each pixel of the special light image from the luminance signals of the input narrow-band light image using the expression (15), and outputs the calculated edge quantity $E(x, y)$ to the feature quantity addition section 357 as the feature quantity f'(x, y).

The feature quantity addition section 357 performs the highlight process on the normal light image corresponding to the type of the special light image. The type of the special light image may be determined referring to the flag signal transmitted from the control section 360.

When the first rotary filter 140 is inserted into the optical path, the feature quantity addition section 357 performs the color conversion process on the normal light image using the expression (20). Although an example in which the color conversion process is performed on the normal light image based on the feature quantity calculated by the feature quantity calculation section 356 has been described above, the invention is not limited thereto. For example, an arbitrary color conversion process or a luminance conversion process may be performed based on the feature quantity.

When the second rotary filter 150 is inserted into the optical path, the feature quantity addition section 357 adds the feature quantity f'(x, y) output from the feature quantity calculation section 356 to the luminance signal Y(x, y) of the normal light image. Although an example in which the luminance conversion process is performed on the normal light image based on the feature quantity calculated by the feature quantity calculation section 356 has been described above, the invention is not limited thereto. For example, an arbitrary color conversion process or an arbitrary luminance conversion process may be performed based on the feature quantity.

When a fluorescent image is acquired as the special light image by performing the above process, a lesion area (e.g., tumor) is drawn in a color differing from that of a normal area. When a narrow-band light image is acquired as the special light image by performing the above process, a blood vessel area that is important for diagnosing a lesion is highlighted.

The above configuration makes it possible to perform the highlight process on the normal light image corresponding to the type of the special light image. This makes it possible to prevent a situation in which a lesion area is missed while reducing the burden on the doctor during diagnosis using the normal light image and the special light image.

Although an example in which the type of the special light image is determined using the information about the rotary filter that is inserted into the optical path as the flag signal has been described above, the invention is not limited thereto. For example, the type of the special light image may be determined based on the signal output from the second imaging element 260.

A method that determines the type of the special light image based on the signal output from the second imaging element 260 is described below. As illustrated in FIG. 48, the second imaging element 260 has a configuration in which the color filters g4 and b4 are disposed in a staggered arrangement. When the first rotary filter 140 is inserted into the optical path, the fluorescence signal of the fluorescent agent CY5 is output from the second imaging element 260. Therefore, the average value G4_ave of the signal output from each pixel that corresponds to the color filter g4 is almost equal to the average value B4_ave of the signal output from each pixel that corresponds to the color filter b4.

When the second rotary filter 150 is inserted into the optical path, a narrow-band signal that corresponds to a wavelength band of 530 to 550 nm (color filter g4) and a narrow-band signal that corresponds to a wavelength band of 390 to 445 nm (color filter b4) are output from the second imaging element 260 (i.e., signals that differ in wavelength band are output depending on the color filter). Therefore, the average values G4_ave and B4_ave differ from each other. Accordingly, the type of the special light image can be determined by comparing the average values G4_ave and B4_ave.

Note that each section of the image processing section 300 need not necessarily be implemented by hardware. For example, a CPU may perform the process of each section on an image acquired in advance in the same manner as in the first embodiment. Specifically, the process of each section may be implemented by software by causing the CPU to execute a program. Alternatively, the process of each section may partially be implemented by software.

Figure 52:
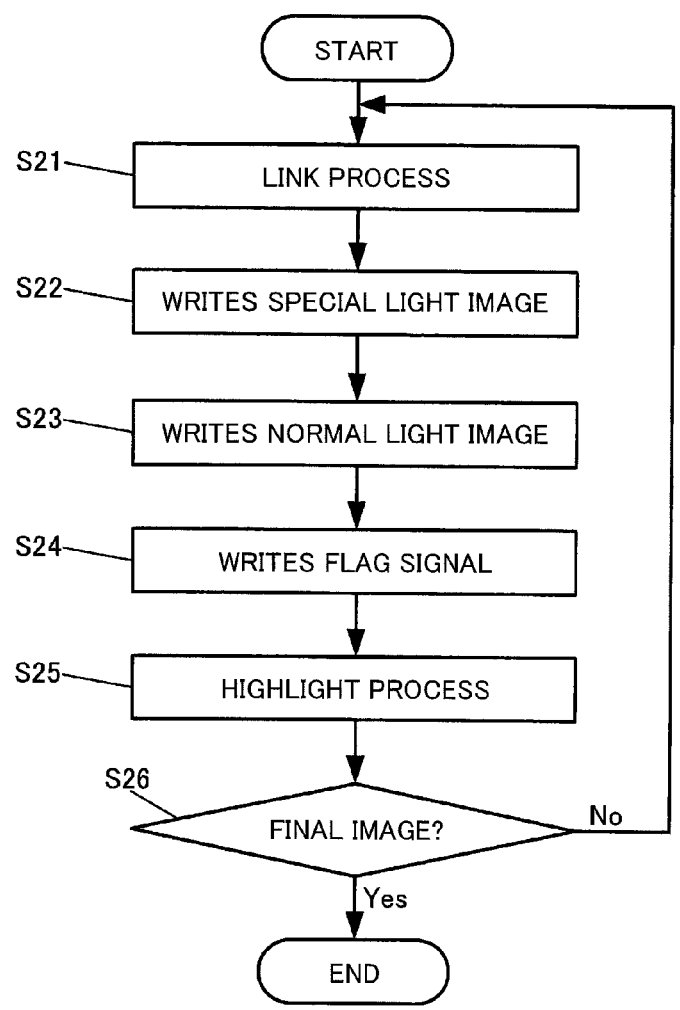
FIG. 52 is another flowchart illustrating a process according to one embodiment of the invention.

A process performed on the normal light image and the special light image acquired in advance when implementing the process of the highlight section 350 and the process of the link section 370 illustrated in FIG. 43 by software is described below using a flowchart illustrated in FIG. 52.

In Step 21, the normal light image and the special light image that have been alternately acquired are linked based on the image acquisition timing information in the same manner as in the fifth embodiment. The special light image is written into the memory (Step 22), and the normal light image linked to the special light image is then written into the memory (Step 23). The flag signal that specifies the type of the special light image is then written into the memory (Step 24).

Figure 53:
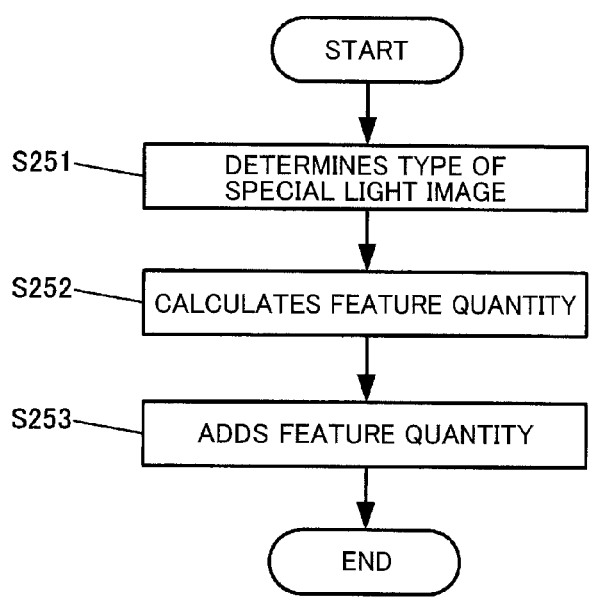
FIG. 53 is another flowchart illustrating a highlight process.

FIG. 53 illustrates the details of the highlight step (Step 25). In the special light image determination step, the type of the special light image is determined referring to the flag signal (Step 251). In the feature quantity calculation step, the feature quantity is calculated corresponding to the type of the special light image (Step 252). More specifically, when the special light image is a fluorescent image, the signal value of the fluorescent image is used as the feature quantity f'(x, y). When the special light image is a narrow-band light image, the edge quantity is calculated from the luminance signal of the narrow-band light image using the expression (15), and used as the feature quantity f'(x, y). In the feature quantity addition step, the highlight process is performed on the normal light image corresponding to the type of the special light image (Step 253). More specifically, when the special light image is a fluorescent image, the color conversion process is performed on the normal light image using the feature quantity calculated in Step 252 and the expression (20). When the special light image is a narrow-band light image, the feature quantity calculated in Step 252 is added to the luminance signal of the normal light image.

The process ends when all of the images have been processed. The process is repeated until all of the images have been processed (Step 26).

According to the sixth embodiment, the first image acquisition section (normal light image acquisition section 320 in a narrow sense) acquires the first image (normal light image in a narrow sense) that corresponds to the wavelength band of white light, and the second image acquisition section (special light image acquisition section 330 in a narrow sense) acquires the second image (special light image (e.g., narrow-band image or fluorescent image) in a narrow sense) that corresponds to the specific wavelength band (the wavelength band of narrow-band light or fluorescence in a narrow sense). The highlight section 350 performs the highlight process on the first image based on the type of the second image.

The second image may be an NBI image or an AFI image. The highlight section 350 may change the method of performing the highlight process depending on whether the second image is an NBI image or an AFI image.

This makes it possible to acquire the normal light image (white light image) and the special light image (e.g., NBI image or fluorescent image), and change the method of performing the highlight process on the normal light image corresponding to the type of the special light image. Therefore, it is possible to perform the process in the same manner as in the third embodiment when the special light image is an NBI image, and perform the process in the same manner as in the fifth embodiment when the special light image is a fluorescent image.

The first to sixth embodiments according to the invention and the modifications thereof have been described above. Note that the invention is not limited to the first to sixth embodiments and the modifications thereof. Various modifications and variations may be made without departing from the scope of the invention. A plurality of elements described in connection with the first to sixth embodiments and the modifications thereof may be appropriately combined to achieve various configurations. For example, some elements may be omitted from the elements described in connection with the first to sixth embodiments and the modifications thereof. Some of the elements described in connection with different embodiments or modifications thereof may be appropriately combined. Specifically, various modifications and applications are possible without materially departing from the novel teachings and advantages of the invention.

Any term (e.g., normal light image or special light image) cited with a different term (e.g., first image or second image) having a broader meaning or the same meaning at least once in the specification and the drawings may be replaced by the different term in any place in the specification and the drawings.

What is claimed is:

1. An image processing device comprising:
   a first image acquisition section that acquires a first image that includes an object image including information within a wavelength band of white light;
   a second image acquisition section that acquires a second image that includes an object image including information within a specific wavelength band;
   a type determination section that determines a type of the object image in the second image based on a feature quantity of pixels included in the second image; and
   a highlight section that performs a highlight process on the first image based on the type of the object image in the second image determined by the type determination section;
   wherein, when a plurality of object images are present in the second image as the object image:

the type determination section determines one type among first to Nth (N is an integer equal to or larger than 2) types to which each of the plurality of object images in the second image belongs, and the highlight section changes a method of performing the highlight process among the determined types to which the plurality of object images in the second image belongs.

2. The image processing device as defined in claim 1, the type determination section changing a feature quantity calculation process corresponding to an organ to which the object image in the second image belongs.

3. The image processing device as defined in claim 1, the highlight section changing a method of performing the highlight process corresponding to an organ to which the object image in the second image belongs.

4. The image processing device as defined in claim 2, at least one of the first image and the second image having been captured by an imaging device provided outside the image processing device, and the highlight section determining the organ to which the object image in the second image belongs based on information about the imaging device that has captured the at least one of the first image and the second image.

5. The image processing device as defined in claim 3, at least one of the first image and the second image having been captured by an imaging device provided outside the image processing device, and the highlight section determining the organ to which the object image in the second image belongs based on information about the imaging device that has captured the at least one of the first image and the second image.

6. The image processing device as defined in claim 1, a priority corresponding to each type being set to each of the first to Nth types, and the highlight section determining the method of performing the highlight process based on the priority that is set corresponding to the type of the respective object image in the second image.

7. The image processing device as defined in claim 6, the highlight section setting the priority to the type of the respective object image in the second image corresponding to an organ to which the respective object image in the second image belongs.

8. The image processing device as defined in claim 6, the highlight section performing the highlight process on one of a plurality of object images in the first image that belongs to a type with a highest priority using a highlight method that corresponds to the type of the object image in the second image.

9. The image processing device as defined in claim 1, the highlight section performing the highlight process on one of a plurality of object images in the first image that belongs to an ith ($1 \leq i \leq N$) type among the first to Nth types using a highlight method that corresponds to the ith type, and performing the highlight process on the object image in the first image that belongs to a jth $j(1 \leq j \leq N, j \neq i)$ type among the first to Nth types using a highlight method that corresponds to the jth type.

10. The image processing device as defined in claim 1, the second image being classified into a plurality of types, and the highlight section determining a method of performing the highlight process corresponding to the type of the respective object image in the second image and the type of the second image.

11. The image processing device as defined in claim 10, further comprising:

an area selection section that selects a corresponding attention area from the first image, the corresponding attention area corresponding to an attention area within the second image that includes the object image, the highlight section determining the corresponding attention area that is an area corresponding to a blood vessel to be a range subjected to the highlight process when the object image of the second image is a blood vessel and the second image is a Narrow Band Imaging image.

12. The image processing device as defined in claim 10, the highlight section determining entirety of the first image to be a range subjected to the highlight process when the object image of the second image is a lesion and the second image is a Narrow Band Imaging image.

13. The image processing device as defined in claim 1, the highlight section performing the highlight process that highlights a specific frequency component of a spatial frequency of the first image over entirety of the first image.

14. The image processing device as defined in claim 1, further comprising:

an area selection section that selects a corresponding attention area from the first image, the corresponding attention area corresponding to an attention area within the second image that includes the object image, the highlight section performing the highlight process that enhances a luminance component or a color component of a signal included in the corresponding attention area within the first image based on an edge quantity calculated from the second image.

15. The image processing device as defined in claim 1, further comprising:

an area selection section that selects a corresponding attention area from the first image, the corresponding attention area corresponding to an attention area within the second image that includes the object image, the highlight section performing the highlight process that enhances a luminance component or a color component of a signal included in the corresponding attention area within the first image based on a color feature quantity calculated from the second image.

16. The image processing device as defined in claim 1, the feature quantity being a quantity that indicates an edge, hue, or intensity.

17. The image processing device as defined in claim 1, the type of the object image in the second image including at least one type among a type of lesion and a type of blood vessel.

18. The image processing device as defined in claim 1, the specific wavelength band being narrower than the wavelength band of the white light.

19. The image processing device as defined in claim 1, each of the first image and the second image being an in vivo image, and the specific wavelength band included in each in vivo image being a wavelength band of light that is easily absorbed by hemoglobin in blood.

20. The image processing device as defined in claim 19, the specific wavelength band being 390 to 445 nm or 530 to 550 nm.

21. The image processing device as defined in claim 1, each of the first image and the second image being an in vivo image, and the specific wavelength band included in each in vivo image being a wavelength band of fluorescence produced by a fluorescent substance.

22. The image processing device as defined in claim 21, the specific wavelength band being 490 to 625 nm.

23. The image processing device as defined in claim 1, each of the first image and the second image being an in vivo image, and
the specific wavelength band included in each in vivo image being a wavelength band of infrared light.

24. The image processing device as defined in claim 23, the specific wavelength band being 790 to 820 nm or 905 to 970 nm.

25. The image processing device as defined in claim 1, the second image acquisition section generating the second image based on the first image acquired by the first image acquisition section.

26. The image processing device as defined in claim 25, the second image acquisition section including a signal extraction section that extracts a signal within the wavelength band of the white light from the first image acquired by the first image acquisition section, and
the second image acquisition section generating the second image that includes a signal within the specific wavelength band based on the signal extracted by the signal extraction section.

27. The image processing device as defined in claim 26, the second image acquisition section including a matrix data setting section that sets matrix data for calculating the signal within the specific wavelength band from the signal within the wavelength band of the white light, and
the second image acquisition section calculating the signal within the specific wavelength band from the signal within the wavelength band of the white light using the matrix data set by the matrix data setting section to generate the second image.

28. An electronic apparatus comprising the image processing device as defined in claim 1.

29. The image processing device as defined in claim 1, a type of the second image including a Narrow Band Imaging image and an Auto Fluorescent Imaging image.

30. The image processing device as defined in claim 29, the highlight section changing a method of performing the highlight process corresponding to whether the second image is a Narrow Band Imaging image or an Auto Fluorescent Imaging image.

31. An information storage device storing a program that causes a computer to function as:
a first image acquisition section that acquires a first image that includes an object image including information within a wavelength band of white light;
a second image acquisition section that acquires a second image that includes an object image including information within a specific wavelength band;
a type determination section that determines a type of the object image in the second image based on a feature quantity of pixels included in the second image; and
a highlight section that performs a highlight process on the first image based on the type of the object image in the second image determined by the type determination section;
wherein, when a plurality of object images are present in the second image as the object image:
the type determination section determines one type among first to Nth (N is an integer equal to or larger than 2) types to which each of the plurality of object images in the second image belongs, and
the highlight section changes a method of performing the highlight process among the determined types to which the plurality of object images in the second image belongs.

32. An image processing method comprising:
acquiring a first image that includes an object image including information within a wavelength band of white light;
acquiring a second image that includes an object image including information within a specific wavelength band;
determining a type of the object image in the second image based on a feature quantity of pixels included in the second image; and
performing a highlight process on the first image based on the determined type of the object image in the second image;
wherein, when a plurality of object images are present in the second image as the object image:
the type determination determines one type among first to Nth (N is an integer equal to or larger than 2) types to which each of the plurality of object images in the second image belongs, and
the highlight process changes a method of performing the highlight process among the determined types to which the plurality of object images in the second image belongs.

* * * * *